(12) United States Patent
Kamal et al.

(10) Patent No.: US 8,759,339 B2
(45) Date of Patent: Jun. 24, 2014

(54) PYRROLO[2,1-C][1,4]NAPHTHODIAZEPINE LINKED PIPERAZINE COMPOUNDS AND A PROCESS FOR THE PREPARATION THEREOF

(75) Inventors: Ahmed Kamal, Hyderabad (IN); Jayanti Naga Srirama Chandra Murty, Hyderabad (IN); Arutla Viswanath, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/985,510

(22) PCT Filed: Jan. 10, 2012

(86) PCT No.: PCT/IN2012/000026
§ 371 (c)(1),
(2), (4) Date: Aug. 14, 2013

(87) PCT Pub. No.: WO2012/111020
PCT Pub. Date: Aug. 23, 2012

(65) Prior Publication Data
US 2013/0317211 A1    Nov. 28, 2013

(30) Foreign Application Priority Data

Feb. 14, 2011   (IN) .............................. 368/DEL/2011

(51) Int. Cl.
*C07D 487/04*    (2006.01)
*A61K 31/55*    (2006.01)

(52) U.S. Cl.
USPC ........................................ 514/219; 540/494

(58) Field of Classification Search
USPC ........................................ 540/494; 514/219
See application file for complete search history.

(56) References Cited

PUBLICATIONS

Gregson et al., "Design, Synthesis, and Evaluation of a Novel Pyrrolobenzodiazepine DNA-Interactive Agent with Highly Efficient Cross-Linking Ability and Potent Cytotoxicity", *J. Med. Chem.*, 44:737-748, 2001.
Hurley et al., "Pyrrolo(1,4)Benzodiazepine Antitumor Antibiotics: In vitro Interaction of Anthramycin, Sibiromycin and Tomaymycin with DNA Using Specifically Radiolabelled Molecules", *Biochimica et Biophysica Acta*, 475:521-535, 1977.
Hurley, "Pyrrolo(1,4)Benzodiazepine Antitumor Antibiotics. Comparative Aspects of Anthramycin, Tomaymycin and Sibiromycin", *The Journal of Antibiotics*, 30(5):349-370, 1977.
International Preliminary Report on Patentability issued in PCT Application No. PCT/IN2012/000026, dated Aug. 21, 2013.
International Search Report issued in PCT Application No. PCT/IN2012/000026, mailed Apr. 2, 2012.
Kamal and Rao, "A new route for the synthesis of pyrrolo[2,1-c][1,4]benzodiazepine antibiotics via oxidation of cyclic secondary amine", *Chem. Commun.*, pp. 385-386, 1996.
Kamal et al., "Design, Synthesis, and Evaluation of New Noncross-Linking Pyrrolobenzodiazepine Dimers with Efficient DNA Binding Ability and Potent Antitumor Activity", *J. Med. Chem.*, 45:4679-4688, 2002.
Kamal et al., "Synthesis of Pyrrolo[2,1-c][1,4]benzodiazepine Antibiotics via Azido Reductive Cyclization with HMDST", *Tetrahedron Letters*, 37(37):6803-6806, 1996.
Kaplan and Hurley, "Anthramycin Binding to Deoxyribonucleic Acid-Mitomycin C Complexes. Evidence for Drug-Induced Deoxyribonucleic Acid Conformational Change and Cooperativity in Mitomycin C Binding", *Biochemistry*, 20:7572-7580, 1981.
Kohn and Spears, "Reaction of Anthramycin with Deoxyribonucleic Acid", *J. Mol. Biol.*, 51:551-572, 1970.
Kunimoto et al., "Mazethramycin, A New Member of Anthramycin Group Antibiotics", *The Journal of Antibiotics*, 33(6):665-667, 1980.
Lown and Joshua, "Molecular Mechanism of Binding of Pyrrol(1,4)Benzodiazepine Antitumour Agents to Deoxyribonucleic Acid: Anthramycin and Tomaymycin", *Biochemica Pharmacology*, 28:2017-2026, 1979.
Molina et al., "Synthesis of Pyrrolo[2,1-c][1,4]benzodiazepines via an Intramolecular Aza-Wittig Reaction. Synthesis of the Antibiotic DC-81", *Tetrahedron*, 51(19):5617-5630, 1995.
Shimizu et al., "Prothracarcin, a Novel Antitumor Antibiotic", *The Journal of Antibiotics*, 35(8):972-978, 1982.
Thurston and Bose, "Synthesis of DNA-Interactive Pyrrolo[2,1-c][1,4]benzodiazepines", *Chem. Rev.*, 94:433-465, 1994.
Thurston et al., "Effect of A-Ring Modifications on the DNA-Binding Behavior and Cytotoxicity of Pyrrolo[2,1-c][1,4]benzodiazepines", *Journal of Medicinal Chemistry*, 42(3):1951-1964, 1999.

*Primary Examiner* — Bruck Kifle
(74) *Attorney, Agent, or Firm* — Fulbright & Jaworski LLP

(57) ABSTRACT

The present invention provides a compound of general formula A, useful as potential antitumour agents against five human cancer cell lines. The present invention further provides a process for the preparation of pyrrolo[2,1-c][1,4] naphthodiazepine linked substituted piperazine conjugates attached through different alkane spacers of general formula A. (Formula I) General formula A. Where R=R'=(Formula II). n=1-9 and R"=methyl, ethyl, acetyl, benzyl, piperinoyl, 4-fluorophenyl, 4-chlorophenyl, 4-methoxyphenyl, pyridyl, pyrimidyl.

General formula A

17 Claims, 3 Drawing Sheets

Scheme 1

Scheme 2

PYRROLO[2,1-C][1,4]NAPHTHODIAZEPINE LINKED PIPERAZINE COMPOUNDS AND A PROCESS FOR THE PREPARATION THEREOF

This application is a national phase application under 35 U.S.C. §371 of International Application No. PCT/IN2012/000026 filed 10 Jan. 2012, which claims priority to Indian Patent Application No. 368/DEL/2011 filed 14 Feb. 2011. The entire text of each of the above-referenced disclosures is specifically incorporated herein by reference without disclaimer.

FIELD OF THE INVENTION

The present invention relates to Pyrrolo[2,1-c][1,4]naphthodiazepine linked substituted piperazine compounds of general formula A as potential antitumour agents and process for the preparation thereof. The Present invention further relates to Pyrrolo[2,1-c][1,4]naphthodiazepine linked substituted piperazine compounds are attached through different alkane spacers of general formula A.

General formula A

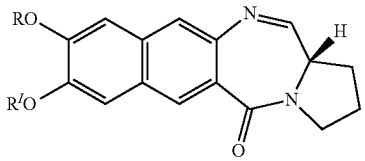

Where $R=R=CH_3$,

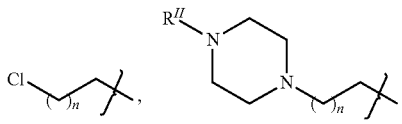

n=1-9 and $R^{II}$=methyl, ethyl, acetyl, benzyl, piperinoyl, 4-fluorophenyl, 4-chlorophenyl, 4-methoxyphenyl, pyridyl, pyrimidyl

BACKGROUND OF THE INVENTION

Pyrrolo[2,1-c][1,4]benzodiazepines (PBDs), a group of potent naturally occurring antitumour antibiotics from various *Streptomyces* species, are of considerable interest because of their ability to recognize and subsequently form covalent bonds to specific base sequence of double strand DNA (Dervan, P. B. *Science* 1989, 232, 464; Hurley, L. H. *J. Med. Chem.* 1989, 32, 2027; Thurston, D. E.; Thompson, A. S. *Chem. Br.* 1990, 26, 767). Well-known members of this group include anthramycin, DC-81, sibiromycin, tomamycin, chicamycin and neothramycin of A and B (Hurley, L. H. *J. Antibiot.* 1977, 30, 349; Schimizu, K.; Kawamoto, I.; Tomita, F.; Morimoto, M.; FuJimoto, K. *J. Antibiot.* 1982, 35, 992.; Lown, J. W.; Joshua, A. V. *Biochem. Pharmacol.* 1979, 28, 2017; Thurston, D. E.; Bose, D. S. *Chem. Rev.* 1994, 94, 433.; Molina, P.; Diaz, I.; Tarraga, A. *Tetrahedron* 1995, 51, 5617.; Kamal, A.; Rao, N. V. *Chem. Commun.* 1996, 385; Kamal, A.; Reddy, B. S. P.; Reddy, B. S, N. *Tetrahedron Lett* 1996, 37, 6803). The cytotoxicity and antitumour activity of these agents are attributed to their property of sequence selective covalent binding to the N2 of guanine in the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.*, 1980, 33, 665.; Kohn, K. W. and Speous, C. L. *J. Mol. Biol.,* 1970, 51, 551.; Hurley, L. H.; Gairpla, C. and ZmiJewski, M. *Biochem. Biophys. Acta.*, 1977, 475, 521.; Kaplan, D. J. and Hurley, L. H. *Biochemistry,* 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. j.; Jenkins, T. C.; Neidle, S, and Hurley, L. H. *J. Org. Chem.* 1996, 61, 8141).

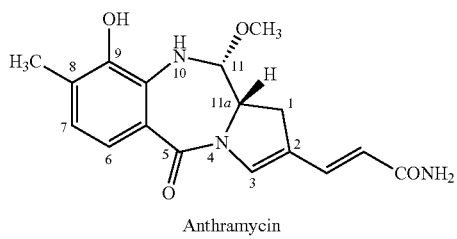

Anthramycin

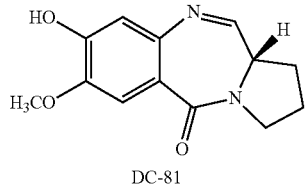

DC-81

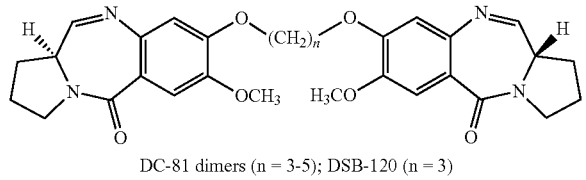

DC-81 dimers (n = 3-5); DSB-120 (n = 3)

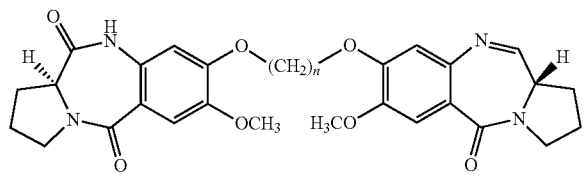

Imine-amide PBD dimers; n = 3-5

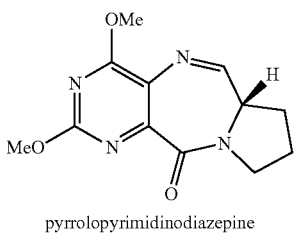

pyrrolopyrimidinodiazepine

-continued

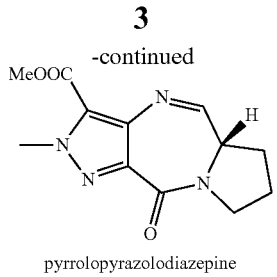

pyrrolopyrazolodiazepine

Recently, PBD dimers have been developed that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). A non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679). However, the clinical efficacy for these antibiotics is hindered by several limitations, such as poor water solubility, cardio toxicity, development of drug resistance and metabolic inactivation. Due to the excellent activity of these molecules, there is needed to develop novel derivatives which are devoid of above limitations.

Several A-ring-modified analogues of the DNA-binding antitumor agent DC-81 have been synthesized in order to study structure-reactivity/cytotoxicity relationships. A-ring replaced with pyridine, diazine, pyrimidine, pyrazole and indole rings to give the novel pyrrolo[2,1-c][1,4]pyridodiazepine, pyrrolo[2,1-c][1,4]pyrazolodiazepine, pyrrolo[2,1-c][1,4]diazinodiazepine, pyrrolo[2,1-c][1,4]pyrimidinodiazepine and pyrrolo[2,1-c][1,4]indolodiazepine systems, respectively. Replacement of a benzene ring with naphthalene ring dramatically increases both the DNA binding affinity and cytotoxicity of pyrrolo naphtho diazepine monomers (PND), as can be seen from the $\Delta T_m$ and $IC_{50}$ values. On the basis of the increased cytotoxicity of the compound, it would appear that the best position for joining fused ring systems of a PBD is furthest from the bridge carbons.

OBJECTIVES OF THE INVENTION

The main objective of the present invention is to provide Pyrrolo[2,1-c][1,4]naphthodiazepine linked substituted piperazine compounds of formula A.

Another objective of the present invention is to provide Pyrrolo[2,1-c][1,4]naphthodiazepine linked substituted piperazine compounds of formula 1a-i to 24a-i.

Another objective of the present invention is to provide Pyrrolo[2,1-c][1,4]naphthodiazepine linked substituted piperazine compounds of formula 1a-i to 24a-i, useful as anticancer agents.

Yet another objective of the present invention is to provide a process for the preparation of Pyrrolo[2,1-c][1,4]naphthodiazepine linked substituted piperazine compounds of formula 1a-i to 24a-i.

SUMMARY OF THE INVENTION

Accordingly, the present invention provides Pyrrolo[2,1-c][1,4]naphthodiazepine linked substituted piperazine compounds of general formula A.

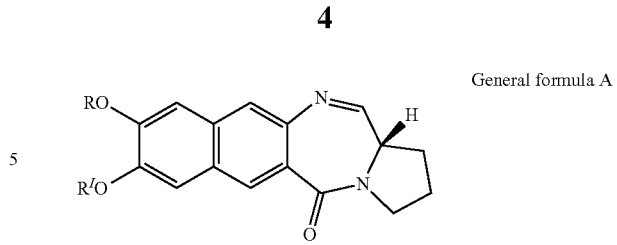

General formula A

Where $R=R^I=CH_3$,

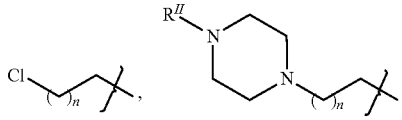

n=1-9 and $R^{II}$=methyl, ethyl, acetyl, benzyl, piperinoyl, 4-fluorophenyl, 4-chlorophenyl, 4-methoxyphenyl, pyridyl, pyrimidyl In one embodiment of the present invention, pyrrolo[2,1-c][1,4]naphthodiazepine linked substituted piperazine compounds of general formula A as claimed in claim 1, wherein chemical formula of the representative compounds of formula 1a- to 24a-i are:

8-Methoxy-9-(2-chloroethoxy)-(13aS)-1,2,3,13a-tetrahydro-5H-pyrrolo[2,1-c][1,4]naphthodiazepine-5-one (1a)

8-Methoxy-9-(3-chloropropoxy)-(13aS)-1,2,3,13a-tetrahydro-5H-pyrrolo[2,1-c][1,4]naphthodiazepine-5-one (1b)

8-Methoxy-9-(4-chlorobutoxy)-(13aS)-1,2,3,13a-tetrahydro-5H-pyrrolo[2,1-c][1,4]naphthodiazepine-5-one (1c)

8-Methoxy-9-[(S-chloropentyl)oxy]-(3aS)-1,2,3,13a-tetrahydro-5H-pyrrolo[2,1-c][1,4]naphthodiazepine-5-one (1d)

8-Methoxy-9-[(6-chlorohexyl)oxy]-(13aS)-1,2,3,13a-tetrahydro-5H-pyrrolo[2,1-c][1,4]naphthodiazepine-5-one (1e)

8-Methoxy-9-[(7-chloroheptyl)oxy]-(13aS)-1,2,3,13a-tetrahydro-5H-pyrrolo[2,1-c][1,4]naphthodiazepine-5-one (1f)

8-Methoxy-9-[(8-chloro octyl)oxy]-(13aS)-1,2,3,13a-tetrahydro-5H-pyrrolo[2,1-c][1,4]naphthodiazepine-5-one (1g)

8-Methoxy-9-[(9-chlorononyl)oxy]-(13aS)-1,2,3,13a-tetrahydro-5H-pyrrolo[2,1-c][1,4]naphthodiazepine-5-one (1h)

8-Methoxy-9-[(10-chlorodecyl)oxy]-(13aS)-1,2,3,13a-tetrahydro-5H-pyrrolo[2,1-c][1,4]naphthodiazepine-5-one (1i)

9-Methoxy-8-(2-chloroethoxy)-(13aS)-1,2,3,13a-tetrahydro-5H-pyrrolo[2,1-c][1,4]naphthodiazepine-5-one (2a)

9-Methoxy-8-(3-chloropropoxy)-(13aS)-1,2,3,13a-tetrahydro-5H-pyrrolo[2,1-c][1,4]naphthodiazepine-5-one (2b)

9-Methoxy-8-(4-chlorobutoxy)-(13aS)-1,2,3,13a-tetrahydro-5H-pyrrolo[2,1-c][1,4]naphthodiazepine-5-one (2c)

9-Methoxy-8-[(S-chloropentyl)oxy]-(13aS)-1,2,3,13a-tetrahydro-5H-pyrrolo[2,1-c][1,4]naphthodiazepine-5-one (2d)

9-Methoxy-8-[(6-chlorohexyl)oxy]-(13aS)-1,2,3,13a-tetrahydro-5H-pyrrolo[2,1-c][1,4]naphthodiazepine-5-one (2e)

9-Methoxy-8-[(7-chloroheptyl)oxy]-(13aS)-1,2,3,13a-tetrahydro-5H-pyrrolo[2,1-c][1,4]naphthodiazepine-5-one (2f)

9-Methoxy-8-[(8-chloro octyl)oxy]-(13aS)-1,2,3,13a-tetrahydro-5H-pyrrolo[2,1-c][1,4]naphthodiazepine-5-one (2g)

9-Methoxy-8-[(9-chlorononyl)oxy]-(13aS)-1,2,3,13a-tetrahydro-5H-pyrrolo[2,1-c][1,4]naphthodiazepine-5-one (2h)

9-Methoxy-8-[(10-chlorodecyl)oxy]-(13aS)-1,2,3,13a-tetrahydro-5H-pyrrolo[2,1-c][1,4]naphthodiazepine-5-one (2i)

8-Methoxy-9-[2-(4-methylpiperazino)ethoxy]-(13aS)-1,2,3,13a-tetrahydro-5H-pyrrolo[2,1-c][1,4]naphthodiazepin-5-one (3a)

8-Methoxy-9-[3-(4-methylpiperazino)propoxy]-(13aS)-1,2,3,13a-tetrahydro-5H-pyrrolo[2,1-c][1,4]naphthodiazepin-5-one (3b)

8-Methoxy-9-[4-(4-methylpiperazino)butoxy]-(13aS)-1,2,3,13a-tetrahydro-5H-pyrrolo[2,1-c][1,4]naphthodiazepin-5-one (3c)

8-Methoxy-9-[5-(4-methylpiperazino)pentyloxy]-(13aS)-1,2,3,13a-tetrahydro-5H-pyrrolo[2,1-c][1,4]naphthodiazepin-5-one (3d)

8-Methoxy-9-[6-(4-methylpiperazino)hexyloxy]-(13aS)-1,2,3,13a-tetrahydro-5H-pyrrolo[2,1-c][1,4]naphthodiazepin-5-one (3e)

8-Methoxy-9-[7-(4-methylpiperazino)heptyloxy]-(13aS)-1,2,3,13a-tetrahydro-5H-pyrrolo[2,1-c][1,4]naphthodiazepin-5-one (3f)

8-Methoxy-9-[8-(4-methylpiperazino)octyloxy]-(13aS)-1,2,3,13a-tetrahydro-5H-pyrrolo[2,1-c][1,4]naphthodiazepin-5-one (3g)

8-Methoxy-9-[9-(4-methylpiperazino)nonyloxy]-(13aS)-1,2,3,13a-tetrahydro-5H-pyrrolo[2,1-c][1,4]naphthodiazepin-5-one (3h)

8-Methoxy-9-[10-(4-methylpiperazino)decyloxy]-(13aS)-1,2,3,13a-tetrahydro-5H-pyrrolo[2,1-c][1,4]naphthodiazepin-5-one (3i)

8-Methoxy-9-[2-(4-ethylpiperazino)ethoxy]-(13aS)-1,2,3,13a-tetrahydro-5H-pyrrolo[2,1-c][1,4]naphthodiazepin-5-one (4a)

8-Methoxy-9-[3-(4-ethylpiperazino)propoxy]-(13aS)-1,2,3,13a-tetrahydro-5H-pyrrolo[2,1-c][1,4]naphthodiazepin-5-one (4b)

8-Methoxy-9-[4-(4-ethylpiperazino)butoxy]-(13aS)-1,2,3,13a-tetrahydro-5H-pyrrolo[2,1-c][1,4]naphthodiazepin-5-one (4c)

8-Methoxy-9-[5-(4-ethylpiperazino)pentyloxy]-(13aS)-1,2,3,13a-tetrahydro-5H-pyrrolo[2,1-c][1,4]naphthodiazepin-5-one (4d)

8-Methoxy-9-[6-(4-ethylpiperazino)hexyloxy]-(13aS)-1,2,3,13a-tetrahydro-5H-pyrrolo[2,1-c][1,4]naphthodiazepin-5-one (4e)

8-Methoxy-9-[7-(4-ethylpiperazino)heptyloxy]-(13aS)-1,2,3,13a-tetrahydro-5H-pyrrolo[2,1-c][1,4]naphthodiazepin-5-one (4f)

8-Methoxy-9-[8-(4-ethylpiperazino)octyloxy]-(13aS)-1,2,3,13a-tetrahydro-5H-pyrrolo[2,1-c][1,4]naphthodiazepin-5-one (4g)

8-Methoxy-9-[9-(4-ethylpiperazino)nonyloxy]-(13aS)-1,2,3,13a-tetrahydro-5H-pyrrolo[2,1-c][1,4]naphthodiazepin-5-one (4h)

8-Methoxy-9-[10-(4-ethylpiperazino)decyloxy]-(13aS)-1,2,3,13a-tetrahydro-5H-pyrrolo[2,1-c][1,4]naphthodiazepin-5-one (4i)

8-Methoxy-9-[2-(4-acetylpiperazino)ethoxy]-(13aS)-1,2,3,13a-tetrahydro-5H-pyrrolo[2,1-c][1,4]naphthodiazepin-5-one (5a)

8-Methoxy-9-[3-(4-acetylpiperazino)propoxy]-(13aS)-1,2,3,13a-tetrahydro-5H-pyrrolo[2,1-c][1,4]naphthodiazepin-5-one (5b)

8-Methoxy-9-[4-(4-acetylpiperazino)butoxy]-(13aS)-1,2,3,13a-tetrahydro-5H-pyrrolo[2,1-c][1,4]naphthodiazepin-5-one (5c)

8-Methoxy-9-[5-(4-acetylpiperazino)pentyloxy]-(13aS)-1,2,3,13a-tetrahydro-5H-pyrrolo[2,1-c][1,4]naphthodiazepin-5-one (5d)

8-Methoxy-9-[6-(4-acetylpiperazino)hexyloxy]-(13aS)-1,2,3,13a-tetrahydro-5H-pyrrolo[2,1-c][1,4]naphthodiazepin-5-one (5e)

8-Methoxy-9-[7-(4-acetylpiperazino)heptyloxy]-(3aS)-1,2,3,13a-tetrahydro-5H-pyrrolo[2,1-c][1,4]naphthodiazepin-5-one (5f)

8-Methoxy-9-[8-(4-acetylpiperazino)octyloxy]-(13aS)-1,2,3,13a-tetrahydro-5H-pyrrolo[2,1-c][1,4]naphthodiazepin-5-one (5g)

8-Methoxy-9-[9-(4-acetylpiperazino)nonyloxy]-(13aS)-1,2,3,13a-tetrahydro-5H-pyrrolo[2,1-c][1,4]naphthodiazepin-5-one (5h)

8-Methoxy-9-[10-(4-acetylpiperazino)decyloxy]-(13aS)-1,2,3,13a-tetrahydro-5H-pyrrolo[2,1-c][1,4]naphthodiazepin-5-one (5i)

8-Methoxy-9-[2-(4-benzylpiperazino)ethoxy]-(13aS)-1,2,3,13a-tetrahydro-5H-pyrrolo[2,1-c][1,4]naphthodiazepin-5-one (6a)

8-Methoxy-9-[3-(4-benzylpiperazino)propoxy]-(13aS)-1,2,3,13a-tetrahydro-5H-pyrrolo[2,1-c][1,4]naphthodiazepin-5-one (6b)

8-Methoxy-9-[4-(4-benzylpiperazino)butoxy]-(13aS)-1,2,3,13a-tetrahydro-5H-pyrrolo[2,1-c][1,4]naphthodiazepin-5-one (6c)

8-Methoxy-9-[5-(4-benzylpiperazino)pentyloxy]-(13aS)-1,2,3,13a-tetrahydro-5H-pyrrolo[2,1-c][1,4]naphthodiazepin-5-one (6d)

8-Methoxy-9-[6-(4-benzylpiperazino)hexyloxy]-(13aS)-1,2,3,13a-tetrahydro-5H-pyrrolo[2,1-c][1,4]naphthodiazepin-5-one (6e)

8-Methoxy-9-[7-(4-benzylpiperazino)heptyloxy]-(13aS)-1,2,3,13a-tetrahydro-5H-pyrrolo[2,1-c][1,4]naphthodiazepin-5-one (6f)

8-Methoxy-9-[8-(4-benzylpiperazino)octyloxy]-(13aS)-1,2,3,13a-tetrahydro-5H-pyrrolo[2,1-c][1,4]naphthodiazepin-5-one (6g)

8-Methoxy-9-[9-(4-benzylpiperazino)nonyloxy]-(13aS)-1,2,3,13a-tetrahydro-5H-pyrrolo[2,1-c][1,4]naphthodiazepin-5-one (6h)

8-Methoxy-9-[10-(4-benzylpiperazino)decyloxy]-(13aS)-1,2,3,13a-tetrahydro-5H-pyrrolo[2,1-c][1,4]naphthodiazepin-5-one (6i)

8-Methoxy-9-(2-[4-(1,3-benzodioxol-5-ylmethyl)piperazino]ethoxyl)(13aS)-1,2,3,13a-tetrahydro-5H-pyrrolo[2,1-c][1,4]naphthodiazepin-5-one (7a)

8-Methoxy-9-(3-[4-(1,3-benzodioxol-5-ylmethyl)piperazino]propoxy)(13aS)-1,2,3,13a-tetrahydro-5H-pyrrolo[2,1-c][1,4]naphthodiazepin-5-one (7b)

8-Methoxy-9-(4-[4-(1,3-benzodioxol-5-ylmethyl)piperazino]butoxyl)(13aS)-1,2,3,13a-tetrahydro-5H-pyrrolo[2,1-c][1,4]naphthodiazepin-5-one (7c)

8-Methoxy-9-(5-[4-(1,3-benzodioxol-5-ylmethyl)piperazino]pentyloxy)(13aS)-1,2,3,13a-tetrahydro-5H-pyrrolo[2,1-c][1,4]naphthodiazepin-5-one (7d)

8-Methoxy-9-(6-[4-(1,3-benzodioxol-5-ylmethyl)piperazino]hexyloxy)(13aS)-1,2,3,13a-tetrahydro-5H-pyrrolo[2,1-c][1,4]naphthodiazepin-5-one (7e)

8-Methoxy-9-(7-[4-(1,3-benzodioxol-5-ylmethyl)piperazino]heptyloxy)(13aS)-1,2,3,13a-tetrahydro-5H-pyrrolo[2,1-c][1,4]naphthodiazepin-5-one (7f)

8-Methoxy-9-(8-[4-(1,3-benzodioxol-5-ylmethyl)piperazino]octyloxy)(13aS)-1,2,3,13a-tetrahydro-5H-pyrrolo[2,1-c][1,4]naphthodiazepin-5-one (7g)

8-Methoxy-9-(9-[4-(1,3-benzodioxol-5-ylmethyl)piperazino]nonyloxy)(13aS)-1,2,3,13a-tetrahydro-5H-pyrrolo[2,1-c][1,4]naphthodiazepin-5-one (7h)

8-Methoxy-9-(10-[4-(1,3-benzodioxol-5-ylmethyl)piperazino]decyloxy)(13aS)-1,2,3,13a-tetrahydro-5H-pyrrolo[2,1-c][1,4]naphthodiazepin-5-one (7i)

8-Methoxy-9-[2-(4-phenylpiperazino)ethoxy]-(13aS)-1,2,3,13a-tetrahydro-5H-pyrrolo[2,1-c][1,4]naphthodiazepin-5-one (8a)

8-Methoxy-9-[3-(4-phenylpiperazino)propoxy]-(13aS)-1,2,3,13a-tetrahydro-5H-pyrrolo[2,1-c][1,4]naphthodiazepin-5-one (5b)

8-Methoxy-9-[4-(4-phenylpiperazino)butoxy]-(13aS)-1,2,3,13a-tetrahydro-5H-pyrrolo[2,1-c][1,4]naphthodiazepin-5-one (8c)

8-Methoxy-9-[5-(4-phenylpiperazino)pentyloxy]-(13aS)-1,2,3,13a-tetrahydro-5H-pyrrolo[2,1-c][1,4]naphthodiazepin-5-one (8d)

8-Methoxy-9-[6-(4-phenylpiperazino)hexyloxy]-(13aS)-1,2,3,13a-tetrahydro-5H-pyrrolo[2,1-c][1,4]naphthodiazepin-5-one (8e)

8-Methoxy-9-[7-(4-phenylpiperazino)heptyloxy]-(13aS)-1,2,3,13a-tetrahydro-5H-pyrrolo[2,1-c][1,4]naphthodiazepin-5-one (8f)

8-Methoxy-9-[8-(4-phenylpiperazino)octyloxy]-(13aS)-1,2,3,13a-tetrahydro-5H-pyrrolo[2,1-c][1,4]naphthodiazepin-5-one (8g)

8-Methoxy-9-[9-(4-phenylpiperazino)nonyloxy]-(13aS)-1,2,3,13a-tetrahydro-5H-pyrrolo[2,1-c][1,4]naphthodiazepin-5-one (8h)

8-Methoxy-9-[10-(4-phenylpiperazino)decyloxy]-(13aS)-1,2,3,13a-tetrahydro-5H-pyrrolo[2,1-c][1,4]naphthodiazepin-5-one (8i)

8-Methoxy-9-(2-[4-(4-fluorophenyl)piperazino]ethoxy)-(13aS)-1,2,3,13a-tetrahydro-5H-pyrrolo[2,1-c][1,4]naphthodiazepin-5-one (9a)

8-Methoxy-9-(3-[4-(4-fluorophenyl)piperazino]propoxy)-(13aS)-1,2,3,13a-tetrahydro-5H-pyrrolo[2,1-c][1,4]naphthodiazepin-5-one (9b)

8-Methoxy-9-(4-[4-(4-fluorophenyl)piperazino]butoxy)-(13aS)-1,2,3,13a-tetrahydro-5H-pyrrolo[2,1-c][1,4]naphthodiazepin-5-one (9c)

8-Methoxy-9-(5-[4-(4-fluorophenyl)piperazino]pentyloxy)-(13aS)-1,2,3,13a-tetrahydro-5H-pyrrolo[2,1-c][1,4]naphthodiazepin-5-one (9d)

8-Methoxy-9-(6-[4-(4-fluorophenyl)piperazino]hexyloxy)-(13aS)-1,2,3,13a-tetrahydro-5H-pyrrolo[2,1-c][1,4]naphthodiazepin-5-one (9e)

8-Methoxy-9-(7-[4-(4-fluorophenyl)piperazino]heptyloxy)-(13aS)-1,2,3,13a-tetrahydro-5H-pyrrolo[2,1-c][1,4]naphthodiazepin-5-one (9f)

8-Methoxy-9-(8-[4-(4-fluorophenyl)piperazino]octyloxy)-(13aS)-1,2,3,13a-tetrahydro-5H-pyrrolo[2,1-c][1,4]naphthodiazepin-5-one (9g)

8-Methoxy-9-(9-[4-(4-fluorophenyl)piperazino]nonyloxy)-(13aS)-1,2,3,13a-tetrahydro-5H-pyrrolo[2,1-c][1,4]naphthodiazepin-5-one (9h)

8-Methoxy-9-(10-[4-(4-fluorophenyl)piperazino]decyloxy)-(13aS)-1,2,3,13a-tetrahydro-5H-pyrrolo[2,1-c][1,4]naphthodiazepin-5-one (9i)

8-Methoxy-9-(2-[4-(4-chlorophenyl)piperazino]ethoxy)-(13aS)-1,2,3,13a-tetrahydro-5H-pyrrolo[2,1-c][1,4]naphthodiazepin-5-one (10a)

8-Methoxy-9-(3-[4-(4-chlorophenyl)piperazino]propoxy)-(13aS)-1,2,3,13a-tetrahydro-5H-pyrrolo[2,1-c][1,4]naphthodiazepin-5-one (10b)

8-Methoxy-9-(4-[4-(4-chlorophenyl)piperazino]butoxy)-(13aS)-1,2,3,13a-tetrahydro-5H-pyrrolo[2,1-c][1,4]naphthodiazepin-5-one (10c)

8-Methoxy-9-(5-[4-(4-chlorophenyl)piperazino]pentyloxy)-(13aS)-1,2,3,13a-tetrahydro-5H-pyrrolo[2,1-c][1,4]naphthodiazepin-5-one (10d)

8-Methoxy-9-(6-[4-(4-chlorophenyl)piperazino]hexyloxy)-(13aS)-1,2,3,13a-tetrahydro-5H-pyrrolo[2,1-c][1,4]naphthodiazepin-5-one (10e)

8-Methoxy-9-(7-[4-(4-chlorophenyl)piperazino]heptyloxy)-(13aS)-1,2,3,13a-tetrahydro-5H-pyrrolo[2,1-c][1,4]naphthodiazepin-5-one (10f)

8-Methoxy-9-(8-[4-chlorophenyl)piperazino]octyloxy)-(3aS)-1,2,3,13a-tetrahydro-5H-pyrrolo[2,1-c][1,4]naphthodiazepin-5-one (10g)

8-Methoxy-9-(9-[4-(4-chlorophenyl)piperazino]nonyloxy)-(13aS)-1,2,3,13a-tetrahydro-5H-pyrrolo[2,1-c][1,4]naphthodiazepin-5-one (10h)

8-Methoxy-9-(10-[4-(4-chlorophenyl)piperazino]decyloxy)-(13aS)-1,2,3,13a-tetrahydro-5H-pyrrolo[2,1-c][1,4]naphthodiazepin-5-one (10i)

8-Methoxy-9-(2-[4-(4-metoxyphenyl)piperazino]ethoxy)-(13aS)-1,2,3,13a-tetrahydro-5H-pyrrolo[2,1-c][1,4]naphthodiazepin-5-one (11a)

8-Methoxy-9-(3-[4-(4-metoxyphenyl)piperazino]propoxy)-(13aS)-1,2,3,13a-tetrahydro-5H-pyrrolo[2,1-c][1,4]naphthodiazepin-5-one (11b)

8-Methoxy-9-(4-[4-(4-metoxyphenyl)piperazino]butoxy)-(13aS)-1,2,3,13a-tetrahydro-5H-pyrrolo[2,1-c][1,4]naphthodiazepin-5-one (11c)

8-Methoxy-9-(5-[4-(4-metoxyphenyl)piperazino]pentyloxy)-(13aS)-1,2,3,13a-tetrahydro-5H-pyrrolo[2,1-c][1,4]naphthodiazepin-5-one (11d)

8-Methoxy-9-(6-[4-(4-metoxyphenyl)piperazino]hexyloxy)-(13aS)-1,2,3,13a-tetrahydro-5H-pyrrolo[2,1-c][1,4]naphthodiazepin-5-one (11e)

8-Methoxy-9-(7-[4-(4-metoxyphenyl)piperazino]heptyloxy)-(13aS)-1,2,3,13a-tetrahydro-5H-pyrrolo[2,1-c][1,4]naphthodiazepin-5-one (11f)

8-Methoxy-9-(8-[4-(4-metoxyphenyl)piperazino]octyloxy)-(13aS)-1,2,3,13a-tetrahydro-5H-pyrrolo[2,1-c][1,4]naphthodiazepin-5-one (11g)

8-Methoxy-9-(9-[4-(4-metoxyphenyl)piperazino]nonyloxy)-(13aS)-1,2,3,13a-tetrahydro-5H-pyrrolo[2,1-c][1,4]naphthodiazepin-5-one (11h)

8-Methoxy-9-(10-[4-(4-metoxyphenyl)piperazino]decyloxy)-(13aS)-1,2,3,13a-tetrahydro-5H-pyrrolo[2,1-c][1,4]naphthodiazepin-5-one (11i)

8-Methoxy-9-(2-[4-(2-pyridyl)piperazino]ethoxy)-(13aS)-1,2,3,13a-tetrahydro-5H-pyrrolo[2,1-c][1,4]naphthodiazepin-5-one (12a)

8-Methoxy-9-(3-[4-(2-pyridyl)piperazino]propoxy)-(13aS)-1,2,3,13a-tetrahydro-5H-pyrrolo[2,1-c][1,4]naphthodiazepin-5-one (12b)

8-Methoxy-9-(4-[4-(2-pyridyl)piperazino]butoxy)-(13aS)-1,2,3,13a-tetrahydro-5H-pyrrolo[2,1-c][1,4]naphthodiazepin-5-one (12c)

8-Methoxy-9-(5-[4-(2-pyridyl)piperazino]pentyloxy)-(13aS)-1,2,3,13a-tetrahydro-5H-pyrrolo[2,1-c][1,4]naphthodiazepin-5-one (12d)

8-Methoxy-9-(6-[4-(2-pyridyl)piperazino]hexyloxy)-(13aS)-1,2,3,13a-tetrahydro-5H pyrrolo[2,1-c][1,4]naphthodiazepin-5-one (12e)

8-Methoxy-9-(7-[4-(2-pyridyl)piperazino]heptyloxy)-(13aS)-1,2,3,13a-tetrahydro-5H-pyrrolo[2,1-c][1,4]naphthodiazepin-5-one (12f)

8-Methoxy-9-(8-[4-(2-pyridyl)piperazino]octyloxy)-(13aS)-1,2,3,13a-tetrahydro-5H-pyrrolo[2,1-c][1,4]naphthodiazepin-5-one (12g)

8-Methoxy-9-(9-[4-(2-pyridyl)piperazino]nonyloxy)-(13aS)-1,2,3,13a-tetrahydro-5H-pyrrolo[2,1-c][1,4]naphthodiazepin-5-one (12h)

8-Methoxy-9-(10-[4-(2-pyridyl)piperazino]decyloxy)-(13aS)-1,2,3,13a-tetrahydro-5H-pyrrolo[2,1-c][1,4]naphthodiazepin-5-one (12i)

8-Methoxy-9-(2-[4-(2-pyrimidinyl)piperazino]ethoxy)-(13aS)-1,2,3,13a-tetrahydro-5H-pyrrolo[2,1-c][1,4]naphthodiazepin-5-one (13a)

8-Methoxy-9-(3-[4-(2-pyrimidinyl)piperazino]propoxy)-(13aS)-1,2,3,13a-tetrahydro-5H-pyrrolo[2,1-c][1,4]naphthodiazepin-5-one (13b)

8-Methoxy-9-(4-[4-(2-pyrimidinyl)piperazino]butoxy)-(13aS)-1,2,3,13a-tetrahydro-5H-pyrrolo[2,1-c][1,4]naphthodiazepin-5-one (13c)

8-Methoxy-9-(5-[4-(2-pyrimidinyl)piperazino]pentyloxy)-(13aS)-1,2,3,13a-tetrahydro-5H-pyrrolo[2,1-c][1,4]naphthodiazepin-5-one (13d)

8-Methoxy-9-(6-[4-(2-pyrimidinyl)piperazino]hexyloxy)-(13aS)-1,2,3,13a-tetrahydro-5H-pyrrolo[2,1-c][1,4]naphthodiazepin-5-one (12e)

8-Methoxy-9-(7-[4-(2-pyrimidinyl)piperazino]heptyloxy)-(13aS)-1,2,3,13a-tetrahydro-5H-pyrrolo[2,1-c][1,4]naphthodiazepin-5-one (13f)

8-Methoxy-9-(8-[4-(2-pyrimidinyl)piperazino]octyloxy)-(13aS)-1,2,3,13a-tetrahydro-5H-pyrrolo[2,1-c][1,4]naphthodiazepin-5-one (13g)

8-Methoxy-9-(9-[4-(2-pyrimidinyl)piperazino]nonyloxy)-(13aS)-1,2,3,13a-tetrahydro-5H-pyrrolo[2,1-c][1,4]naphthodiazepin-5-one (13h)

8-Methoxy-9-(10-[4-(2-pyrimidinyl)piperazino]decyloxy)-(13aS)-1,2,3,13a-tetrahydro-5H-pyrrolo[2,1-c][1,4]naphthodiazepin-5-one (13i)

9-Methoxy-8-[2-(4-methylpiperazino)ethoxy]-(13aS)-1,2,3,13a-tetrahydro-5H-pyrrolo[2,1-c][1,4]naphthodiazepin-5-one (14a)

9-Methoxy-8-[3-(4-methylpiperazino)propoxy]-(13aS)-1,2,3,13a-tetrahydro-5H-pyrrolo[2,1-c][1,4]naphthodiazepin-5-one (14b)

9-Methoxy-8-[4-(4-methylpiperazino)butoxy]-(13aS)-1,2,3,13a-tetrahydro-5H-pyrrolo[2,1-c][1,4]naphthodiazepin-5-one (14c)

9-Methoxy-8-[5-(4-methylpiperazino)pentyloxy]-(13aS)-1,2,3,13a-tetrahydro-5H-pyrrolo[2,1-c][1,4]naphthodiazepin-5-one (14d)

9-Methoxy-8-[6-(4-methylpiperazino)hexyloxy]-(13aS)-1,2,3,13a-tetrahydro-5H-pyrrolo[2,1-c][1,4]naphthodiazepin-5-one (14e)

9-Methoxy-8-[7-(4-methylpiperazino)heptyloxy]-(13aS)-1,2,3,13a-tetrahydro-5H-pyrrolo[2,1-c][1,4]naphthodiazepin-5-one (14f)

9-Methoxy-8-[8-(4-methylpiperazino)octyloxy]-(3aS)-1,2,3,13a-tetrahydro-5H-pyrrolo[2,1-c][1,4]naphthodiazepin-5-one (14g)

9-Methoxy-8-[9-(4-methylpiperazino)nonyloxy]-(13aS)-1,2,3,13a-tetrahydro-5H-pyrrolo[2,1-c][1,4]naphthodiazepin-5-one (14h)

9-Methoxy-8-[10-(4-methylpiperazino)decyloxy]-(13aS)-1,2,3,13a-tetrahydro-5H-pyrrolo[2,1-c][1,4]naphthodiazepin-5-one (14i)

9-Methoxy-8-[2-(4-ethylpiperazino)ethoxy]-(13aS)-1,2,3,13a-tetrahydro-5H-pyrrolo[2,1-c][1,4]naphthodiazepin-5-one (15a)

9-Methoxy-8-[3-(4-ethylpiperazino)propoxy]-(13aS)-1,2,3,13a-tetrahydro-5H-pyrrolo[2,1-c][1,4]naphthodiazepin-5-one (15b)

9-Methoxy-8-[4-(4-ethylpiperazino)butoxy]-(13aS)-1,2,3,13a-tetrahydro-5H-pyrrolo[2,1-c][1,4]naphthodiazepin-5-one (15c)

9-Methoxy-8-[5-(4-ethylpiperazino)pentyloxy]-(13aS)-1,2,3,13a-tetrahydro-5H-pyrrolo[2,1-c][1,4]naphthodiazepin-5-one (15d)

9-Methoxy-8-[6-(4-ethylpiperazino)hexyloxy]-(13aS)-1,2,3,13a-tetrahydro-5H-pyrrolo[2,1-c][1,4]naphthodiazepin-5-one (15e)

9-Methoxy-8-[7-(4-ethylpiperazino)heptyloxy]-(13aS)-1,2,3,13a-tetrahydro-5H-pyrrolo[2,1-c][1,4]naphthodiazepin-5-one (15f)

9-Methoxy-8-[8-(4-ethylpiperazino)octyloxy]-(13aS)-1,2,3,13a-tetrahydro-5H-pyrrolo[2,1-c][1,4]naphthodiazepin-5-one (15g)

9-Methoxy-8-[9-(4-ethylpiperazino)nonyloxy]-(13aS)-1,2,3,13a-tetrahydro-5H-pyrrolo[2,1-c][1,4]naphthodiazepin-5-one (15h)

9-Methoxy-8-[10-(4-ethylpiperazino)decyloxy]-(13aS)-1,2,3,13a-tetrahydro-5H-pyrrolo[2,1-c][1,4]naphthodiazepin-5-one (15i)

9-Methoxy-8-[2-(4-aceylpiperazino)ethoxy]-(13aS)-1,2,3,13a-tetrahydro-5H-pyrrolo[2,1-c][1,4]naphthodiazepin-5-one (16a)

9-Methoxy-8-[3-(4-acetylpiperazino)propoxy]-(13aS)-1,2,3,13a-tetrahydro-5H-pyrrolo[2,1-c][1,4]naphthodiazepin-5-one (16b)

9-Methoxy-8-[4-(4-acetylpiperazino)butoxy]-(13aS)-1,2,3,13a-tetrahydro-5H-pyrrolo[2,1-c][1,4]naphthodiazepin-5-one (16c)

9-Methoxy-8-[5-(4-acetylpiperazino)pentyloxy]-(13aS)-1,2,3,13a-tetrahydro-5H-pyrrolo[2,1-c][1,4]naphthodiazepin-5-one (16d)

9-Methoxy-8-[6-(4-acetylpiperazino)hexyloxy]-(13aS)-1,2,3,13a-tetrahydro-5H-pyrrolo[2,1-c][1,4]naphthodiazepin-5-one (16e)

9-Methoxy-8-[7-(4-acetylpiperazino)heptyloxy]-(13aS)-1,2,3,13a-tetrahydro-5H-pyrrolo[2,1-c][1,4]naphthodiazepin-5-one (16f)

9-Methoxy-8-[8-(4-acetylpiperazino)octyloxy]-(13aS)-1,2,3,13a-tetrahydro-5H-pyrrolo[2,1-c][1,4]naphthodiazepin-5-one (16g)

9-Methoxy-8-[9-(4-acetylpiperazino)nonyloxy]-(13aS)-1,2,3,13a-tetrahydro-5H-pyrrolo[2,1-c][1,4]naphthodiazepin-5-one (16h)

9-Methoxy-8-[10-(4-acetylpiperazino)decyloxy]-(13aS)-1,2,3,13a-tetrahydro-5H-pyrrolo[2,1-c][1,4]naphthodiazepin-5-one (16i)

9-Methoxy-8-[2-(4-benzylpiperazino)ethoxy]-(13aS)-1,2,3,13a-tetrahydro-5H-pyrrolo[2,1-c][1,4]naphthodiazepin-5-one (17a)

9-Methoxy-8-[3-(4-benzylpiperazino)propoxy]-(13aS)-1,2,3,13a-tetrahydro-5H-pyrrolo[2,1-c][1,4]naphthodiazepin-5-one (17b)

9-Methoxy-8-[4-(4-benzylpiperazino)butoxy]-(13aS)-1,2,3,13a-tetrahydro-5H-pyrrolo[2,1-c][1,4]naphthodiazepin-5-one (17c)

9-Methoxy-8-[5-(4-benzylpiperazino)pentyloxy]-(13aS)-1,2,3,13a-tetrahydro-5H-pyrrolo[2,1-c][1,4]naphthodiazepin-5-one (17d)

9-Methoxy-8-[6-(4-benzylpiperazino)hexyloxy]-(13aS)-1,2,3,13a-tetrahydro-5H-pyrrolo[2,1-c][1,4]naphthodiazepin-5-one (17e)

9-Methoxy-8-[7-(4-benzylpiperazino)heptyloxy]-(13aS)-1,2,3,13a-tetrahydro-5H-pyrrolo[2,1-c][1,4]naphthodiazepin-5-one (17f)

9-Methoxy-8-[8-(4-benzylpiperazino)octyloxy]-(13aS)-1,2,3,13a-tetrahydro-5H-pyrrolo[2,1-c][1,4]naphthodiazepin-5-one (17g)

9-Methoxy-8-[9-(4-benzylpiperazino)nonyloxy]-(13aS)-1,2,3,13a-tetrahydro-5H-pyrrolo[2,1-c][1,4]naphthodiazepin-5-one (17h)

9-Methoxy-8-[10-(4-benzylpiperazino)decyloxy]-(13aS)-1,2,3,13a-tetrahydro-5H-pyrrolo[2,1-c][1,4]naphthodiazepin-5-one (17i)

9-Methoxy-8-(2-[4-(1,3-benzodioxol-5-ylmethyl)piperazino]ethoxy)(13aS)-1,2,3,13a-tetrahydro-5H-pyrrolo[2,1-c][1,4]naphthodiazepin-5-one (18a)

9-Methoxy-8-(3-[4-(1,3-benzodioxol-5-ylmethyl)piperazino]propoxy)(13aS)-1,2,3,13a-tetrahydro-5H-pyrrolo[2,1-c][1,4]naphthodiazepin-5-one (18b)

9-Methoxy-8-(4-[4-(1,3-benzodioxol-5-ylmethyl)piperazino]butoxy)(13aS)-1,2,3,13a-tetrahydro-5H-pyrrolo[2,1-c][1,4]naphthodiazepin-5-one (18c)

9-Methoxy-8-(5-[4-(1,3-benzodioxol-5-ylmethyl)piperazino]pentyloxy)(13aS)-1,2,3,13a-tetrahydro-5H-pyrrolo[2,1-c][1,4]naphthodiazepin-5-one (18d)

9-Methoxy-8-(6-[4-(1,3-benzodioxol-5-ylmethyl)piperazino]hexyloxy)(13aS)-1,2,3,13a-tetrahydro-5H-pyrrolo[2,1-c][1,4]naphthodiazepin-5-one (18e)

9-Methoxy-8-(7-[4-(1,3-benzodioxol-5-ylmethyl)piperazino]heptyloxy)(13aS)-1,2,3,13a-tetrahydro-5H-pyrrolo[2,1-c][1,4]naphthodiazepin-5-one (18i)

9-Methoxy-8-(8-[4-(1,3-benzodioxol-5-ylmethyl)piperazino]octyloxy)(13aS)-1,2,3,13a-tetrahydro-5H-pyrrolo[2,1-c][1,4]naphthodiazepin-5-one (18g)

9-Methoxy-8-(9-[4-(1,3-benzodioxol-5-ylmethyl)piperazino]nonyloxy)(13aS)-1,2,3,13a-tetrahydro-5H-pyrrolo[2,1-c][1,4]naphthodiazepin-5-one (18h)

9-Methoxy-8-(10-[4-(1,3-benzodioxol-5-ylmethyl)piperazino]decyloxy)(13aS)-1,2,3,13a-tetrahydro-5H-pyrrolo[2,1-c][1,4]naphthodiazepin-5-one (18i)

9-Methoxy-8-[2-(4-phenylpiperazino)ethoxy]-(3aS)-1,2,3,13a-tetrahydro-5H-pyrrolo[2,1-c][1,4]naphthodiazepin-5-one (19a)

9-Methoxy-8-[3-(4-phenylpiperazino)propoxy]-(13aS)-1,2,3,13a-tetrahydro-5H-pyrrolo[2,1-c][1,4]naphthodiazepin-5-one (19b)

9-Methoxy-8-[4-(4-phenylpiperazino)butoxy]-(13aS)-1,2,3,13a-tetrahydro-5H-pyrrolo[2,1-c][1,4]naphthodiazepin-5-one (19c)

9-Methoxy-8-[5-(4-phenylpiperazino)pentyloxy]-(13aS)-1,2,3,13a-tetrahydro-5H-pyrrolo[2,1-c][1,4]naphthodiazepin-5-one (19d)

9-Methoxy-8-[6-(4-phenylpiperazino)hexyloxy]-(13aS)-1,2,3,13a-tetrahydro-5H-pyrrolo[2,1-c][1,4]naphthodiazepin-5-one (19e)

9-Methoxy-8-[7-(4-phenylpiperazino)heptyloxy]-(13aS)-1,2,3,13a-tetrahydro-5H-pyrrolo[2,1-c][1,4]naphthodiazepin-5-one (19f)

9-Methoxy-8-[8-(4-phenylpiperazino)octyloxy]-(13aS)-1,2,3,13a-tetrahydro-5H-pyrrolo[2,1-c][1,4]naphthodiazepin-5-one (19g)

9-Methoxy-8-[9-(4-phenylpiperazino)nonyloxy]-(13aS)-1,2,3,13a-tetrahydro-5H-pyrrolo[2,1-c][1,4]naphthodiazepin-5-one (19h)

9-Methoxy-8-[10-(4-phenylpiperazino)decyloxy]-(13aS)-1,2,3,13a-tetrahydro-5H-pyrrolo[2,1-c][1,4]naphthodiazepin-5-one (19i)

9-Methoxy-8-(2-[4-(4-fluorophenyl)piperazino]ethoxy)-(13aS)-1,2,3,13a-tetrahydro-5H-pyrrolo[2,1-c][1,4]naphthodiazepin-5-one (20a)

9-Methoxy-8-(3-[4-(4-fluorophenyl)piperazino]propoxy)-(13aS)-1,2,3,13a-tetrahydro-5H-pyrrolo[2,1-c][1,4]naphthodiazepin-5-one (20b)

9-Methoxy-8-(4-[4-(4-fluorophenyl)piperazino]butoxy)-(13aS)-1,2,3,13a-tetrahydro-5H-pyrrolo[2,1-c][1,4]naphthodiazepin-5-one (20c)

9-Methoxy-8-(5-[4-(4-fluorophenyl)piperazino]pentyloxy)-(13aS)-1,2,3,13a-tetrahydro-5H-pyrrolo[2,1-c][1,4]naphthodiazepin-5-one (20d)

9-Methoxy-8-(6-[4-(4-fluorophenyl)piperazino]hexyloxy)-(13aS)-1,2,3,13a-tetrahydro-5H-pyrrolo[2,1-c][1,4]naphthodiazepin-5-one (20e)

9-Methoxy-8-(7-[4-(4-fluorophenyl)piperazino]heptyloxy)-(13aS)-1,2,3,13a-tetrahydro-5H-pyrrolo[2,1-c][1,4]naphthodiazepin-5-one (20f)

9-Methoxy-8-(8-[4-(4-fluorophenyl)piperazino]octyloxy)-(13aS)-1,2,3,13a-tetrahydro-5H-pyrrolo[2,1-c][1,4]naphthodiazepin-5-one (20g)

9-Methoxy-8-(9-[4-(4-fluorophenyl)piperazino]nonyloxy)-(13aS)-1,2,3,13a-tetrahydro-5H-pyrrolo[2,1-c][1,4]naphthodiazepin-5-one (20h)

9-Methoxy-8-(10-[4-(4-fluorophenyl)piperazino]decyloxy)-(13aS)-1,2,3,13a-tetrahydro-5H-pyrrolo[2,1-c][1,4]naphthodiazepin-5-one (20i)

9-Methoxy-8-(2-[4-(4-chlorophenyl)piperazino]ethoxy)-(13aS)-1,2,3,13a-tetrahydro-5H-pyrrolo[2,1-c][1,4]naphthodiazepin-5-one (21a)

9-Methoxy-8-(3-[4-(4-chlorophenyl)piperazino]propoxy)-(13aS)-1,2,3,13a-tetrahydro-5H-pyrrolo[2,1-c][1,4]naphthodiazepin-5-one (21b)

9-Methoxy-8-(4-[4-(4-chlorophenyl)piperazino]butoxy)-(13aS)-1,2,3,13a-tetrahydro-5H-pyrrolo[2,1-c][1,4]naphthodiazepin-5-one (21c)

9-Methoxy-8-(5-[4-(4-chlorophenyl)piperazino]pentyloxy)-(13aS)-1,2,3,13a-tetrahydro-5H-pyrrolo[2,1-c][1,4]naphthodiazepin-5-one (21d)

9-Methoxy-8-(6-[4-(4-chlorophenyl)piperazino]hexyloxy)-(13aS)-1,2,3,13a-tetrahydro-5H-pyrrolo[2,1-c][1,4]naphthodiazepin-5-one (21e)

9-Methoxy-8-(7-[4-(4-chlorophenyl)piperazino]heptyloxy)-(13aS)-1,2,3,13a-tetrahydro-5H-pyrrolo[2,1-c][1,4]naphthodiazepin-5-one (21f)

9-Methoxy-8-(8-[4-(4-chlorophenyl)piperazino]octyloxy)-(13aS)-1,2,3,13a-tetrahydro-5H-pyrrolo[2,1-c][1,4]naphthodiazepin-5-one (21g)

9-Methoxy-8-(9-[4-(4-chlorophenyl)piperazino]nonyloxy)-(13aS)-1,2,3,13a-tetrahydro-5H-pyrrolo[2,1-c][1,4]naphthodiazepin-5-one (21h)

9-Methoxy-8-(10-[4-(4-chlorophenyl)piperazino]decyloxy)-(13aS)-1,2,3,13a-tetrahydro-5H-pyrrolo[2,1-c][1,4]naphthodiazepin-5-one (21i)

9-Methoxy-8-(2-[4-(4-metoxyphenyl)piperazino]ethoxy)-(13aS)-1,2,3,13a-tetrahydro-5H-pyrrolo[2,1-c][1,4]naphthodiazepin-5-one (22a)

9-Methoxy-8-(3-[4-(4-metoxyphenyl)piperazino]propoxy)-(13aS)-1,2,3,13a-tetrahydro-5H-pyrrolo[2,1-c][1,4]naphthodiazepin-5-one (22b)

9-Methoxy-8-(4-[4-(4-metoxyphenyl)piperazino]butoxy)-(13aS)-1,2,3,13a-tetrahydro-5H-pyrrolo[2,1-c][1,4]naphthodiazepin-5-one (22c)

9-Methoxy-8-(5-[4-(4-metoxyphenyl)piperazino]pentyloxy)-(13aS)-1,2,3,13a-tetrahydro-5H-pyrrolo[2,1-c][1,4]naphthodiazepin-5-one (22d)

9-Methoxy-8-(6-[4-(4-metoxyphenyl)piperazino]hexyloxy)-(13aS)-1,2,3,13a-tetrahydro-5H-pyrrolo[2,1-c][1,4]naphthodiazepin-5-one (22e)

9-Methoxy-8-(7-[4-(4-metoxyphenyl)piperazino]heptyloxy)-(13aS)-1,2,3,13a-tetrahydro-5H-pyrrolo[2,1-c][1,4]naphthodiazepin-5-one (22f)

9-Methoxy-8-(8-[4-(4-metoxyphenyl)piperazino]octyloxy)-(13aS)-1,2,3,13a-tetrahydro-5H-pyrrolo[2,1-c][1,4]naphthodiazepin-5-one (22g)

9-Methoxy-8-(9-[4-(4-metoxyphenyl)piperazino]nonyloxy)-(13aS)-1,2,3,13a-tetrahydro-5H-pyrrolo[2,1-c][1,4]naphthodiazepin-5-one (22h)

9-Methoxy-8-(10-[4-(4-metoxyphenyl)piperazino]decyloxy)-(13aS)-1,2,3,13a-tetrahydro-5H-pyrrolo[2,1-c][1,4]naphthodiazepin-5-one (22i)

9-Methoxy-8-(2-[4-(2-pyridyl)piperazino]ethoxy)-(13aS)-1,2,3,13a-tetrahydro-5H-pyrrolo[2,1-c][1,4]naphthodiazepin-5-one (23a)

9-Methoxy-8-(3-[4-(2-pyridyl)piperazino]propoxy)-(13aS)-1,2,3,13a-tetrahydro-5H-pyrrolo[2,1-c][1,4]naphthodiazepin-5-one (23b)

9-Methoxy-8-(4-[4-(2-pyridyl)piperazino]butoxy)-(13aS)-1,2,3,13a-tetrahydro-5H-pyrrolo[2,1-c][1,4]naphthodiazepin-5-one (23c)

9-Methoxy-8-(5-[4-(2-pyridyl)piperazino]pentyloxy)-(13aS)-1,2,3,13a-tetrahydro-5H-pyrrolo[2,1-c][1,4]naphthodiazepin-5-one (23d)

9-Methoxy-8-(6-[4-(2-pyridyl)piperazino]hexyloxy)-(13aS)-1,2,3,13a-tetrahydro-5H-pyrrolo[2,1-c][1,4]naphthodiazepin-5-one (23e)

9-Methoxy-8-(7-[4-(2-pyridyl)piperazino]heptyloxy)-(13aS)-1,2,3,13a-tetrahydro-5H-pyrrolo[2,1-c][1,4]naphthodiazepin-5-one (23f)

9-Methoxy-8-(8-[4-(2-pyridyl)piperazino]octyloxy)-(13aS)-1,2,3,13a-tetrahydro-5H-pyrrolo[2,1-c][1,4]naphthodiazepin-5-one (23g)

9-Methoxy-8-(9-[4-(2-pyridyl)piperazino]nonyloxy)-(13aS)-1,2,3,13a-tetrahydro-5H-pyrrolo[2,1-c][1,4]naphthodiazepin-5-one (23h)

9-Methoxy-8-(10-[4-(2-pyridyl)piperazino]decyloxy)-(13aS)-1,2,3,13a-tetrahydro-5H-pyrrolo[2,1-c][1,4]naphthodiazepin-5-one (23i)

9-Methoxy-8-(2-[4-(2-pyrimidinyl)piperazino]ethoxy)-(13aS)-1,2,3,13a-tetrahydro-5H-pyrrolo[2,1-c][1,4]naphthodiazepin-5-one (24a)

9-Methoxy-8-(3-[4-(2-pyrimidinyl)piperazino]propoxy)-(13aS)-1,2,3,13a-tetrahydro-5H-pyrrolo[2,1-c][1,4]naphthodiazepin-5-one (24b)

9-Methoxy-8-(4-[4-(2-pyrimidinyl)piperazino]butoxy)-(13aS)-1,2,3,13a-tetrahydro-5H-pyrrolo[2,1-c][1,4]naphthodiazepin-5-one (24c)

9-Methoxy-8-(5-[4-(2-pyrimidinyl)piperazino]pentyloxy)-(13aS)-1,2,3,13a-tetrahydro-5H-pyrrolo[2,1-c][1,4]naphthodiazepin-5-one (24d)

9-Methoxy-8-(6-[4-(2-pyrimidinyl)piperazino]hexyloxy)-(13aS)-1,2,3,13a-tetrahydro-5H-pyrrolo[2,1-c][1,4]naphthodiazepin-5-one (24e)

9-Methoxy-8-(7-[4-(2-pyrimidinyl)piperazino]heptyloxy)-(13aS)-1,2,3,13a-tetrahydro-5H-pyrrolo[2,1-c][1,4]naphthodiazepin-5-one (24f)

9-Methoxy-8-(8-[4-(2-pyrimidinyl)piperazino]octyloxy)-(13aS)-1,2,3,13a-tetrahydro-5H-pyrrolo[2,1-c][1,4]naphthodiazepin-5-one (24g)

9-Methoxy-8-(9-[4-(2-pyrimidinyl)piperazino]nonyloxy)-(13aS)-1,2,3,13a-tetrahydro-5H-pyrrolo[2,1-c][1,4]naphthodiazepin-5-one (24h)

9-Methoxy-8-(10-[4-(2-pyrimidinyl)piperazino]decyloxy)-(13aS)-1,2,3,13a-tetrahydro-5H-pyrrolo[2,1-c][1,4]naphthodiazepin-5-one (24i)

In another embodiment of the present invention, pyrrolo[2,1-c][1,4]naphthodiazepine linked substituted piperazine compounds as claimed in claim 1, wherein the structural formula of the representative compounds 1a-i to 24a-i are:

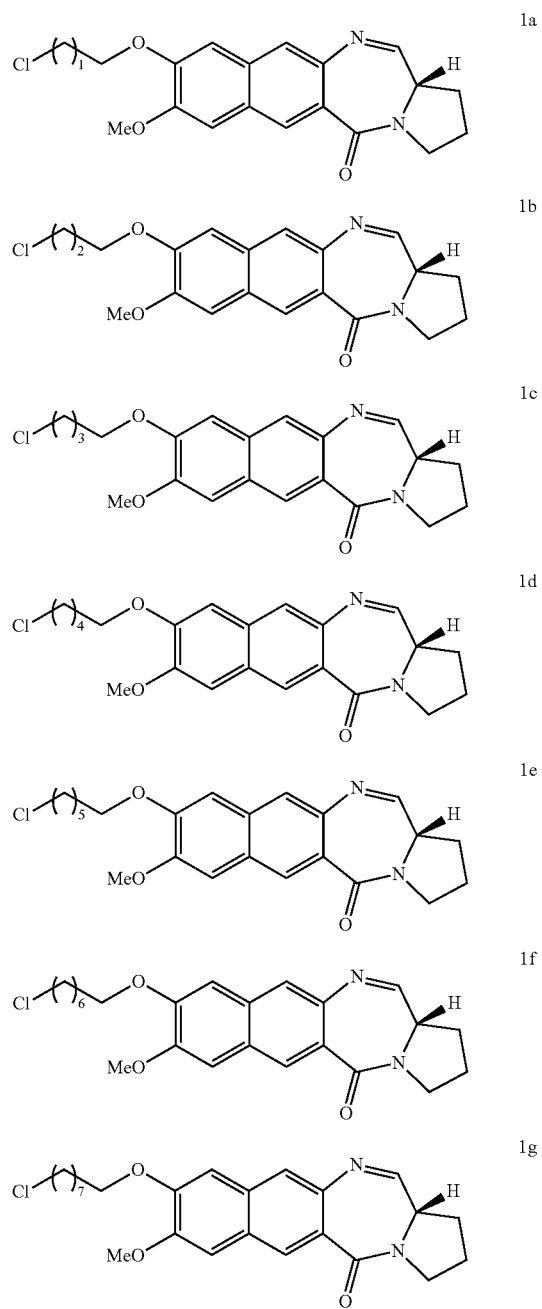

-continued
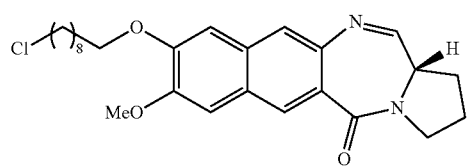
1h
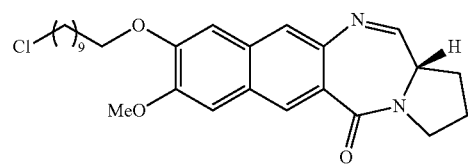
1i
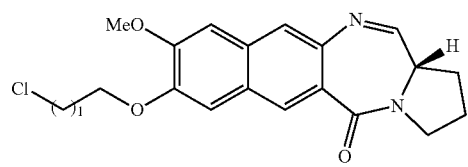
2a
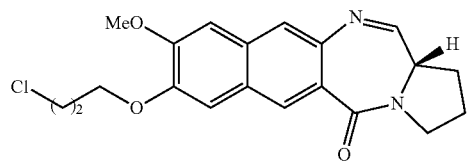
2b
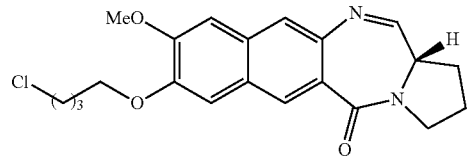
2c
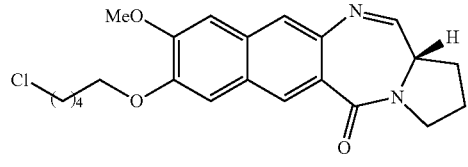
2d
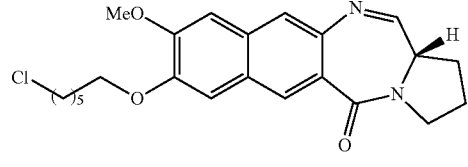
2e
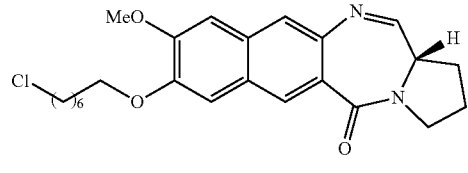
2f
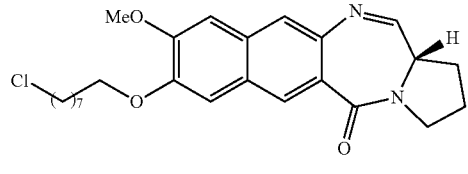
2g
-continued
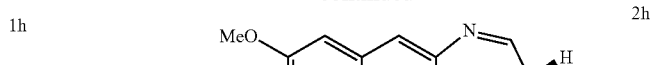
2h
2i
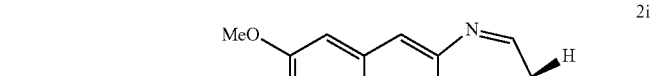
3a
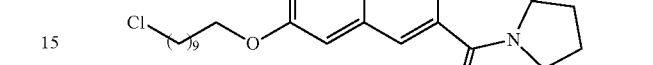
3b
3c
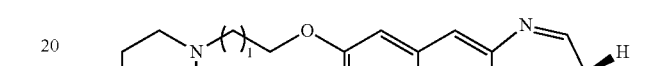
3d
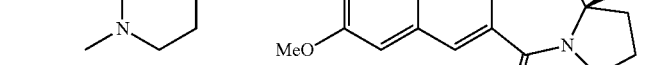
3e
3f

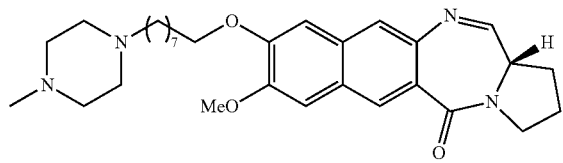
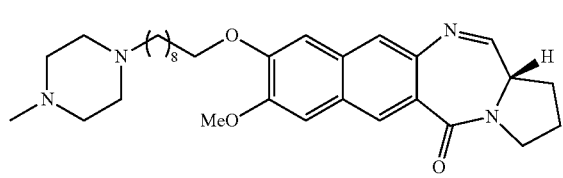
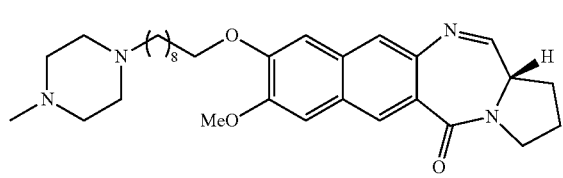
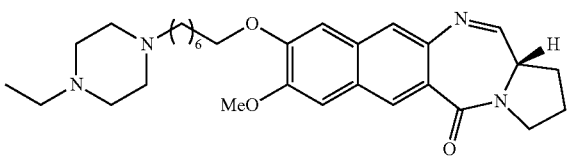
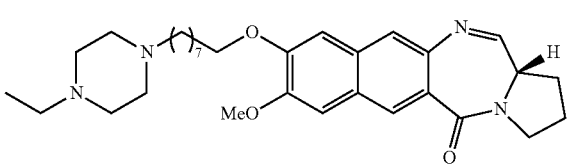

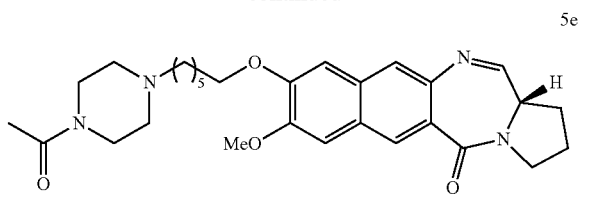
5e
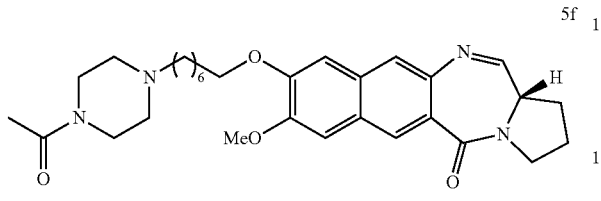
5f
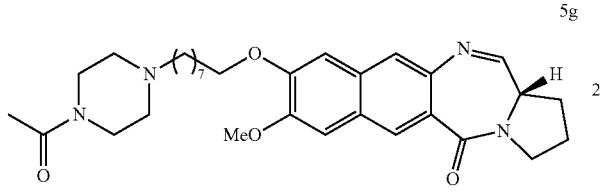
5g
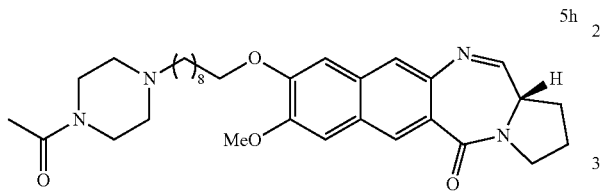
5h
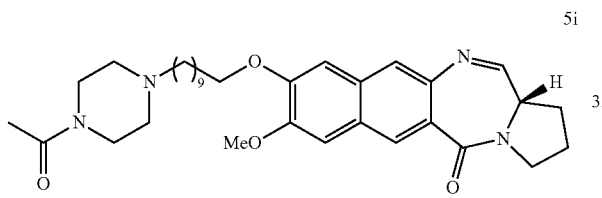
5i
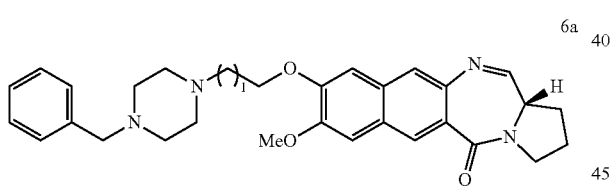
6a
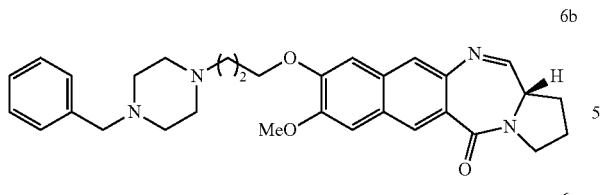
6b
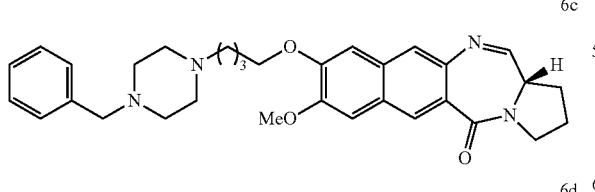
6c
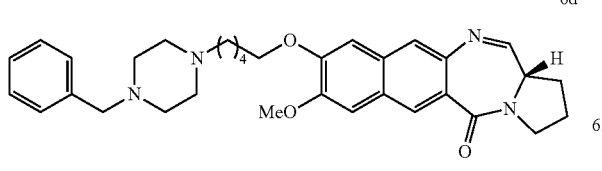
6d
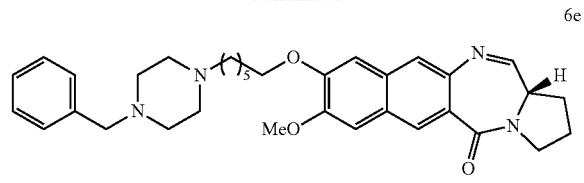
6e
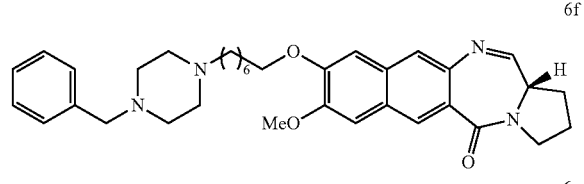
6f
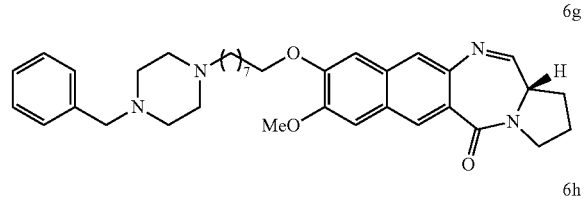
6g
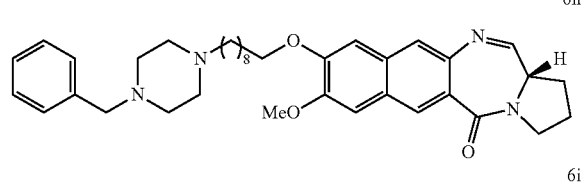
6h
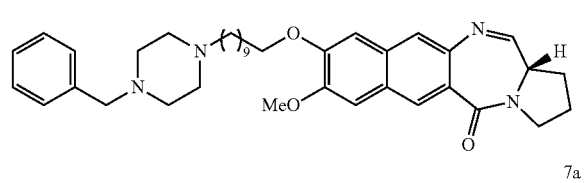
6i
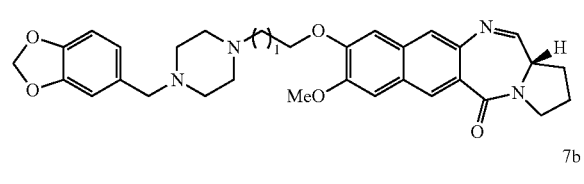
7a
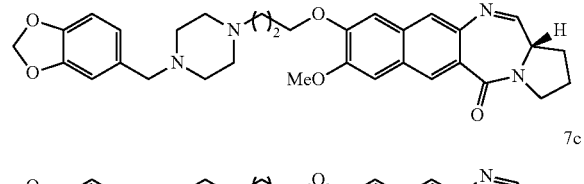
7b
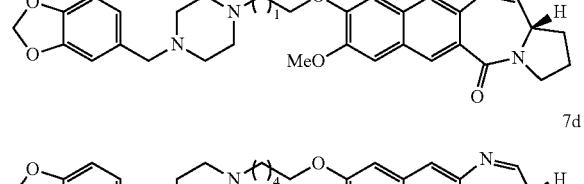
7c
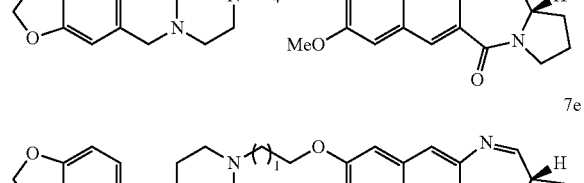
7d
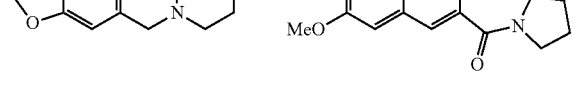
7e

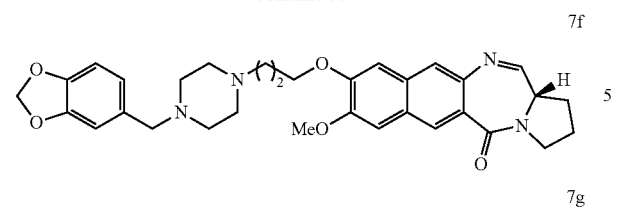 7f
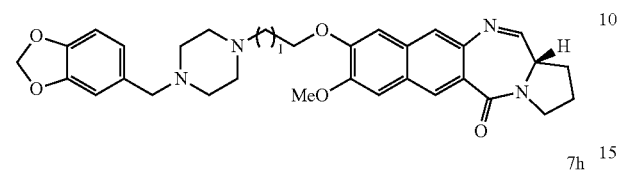 7g
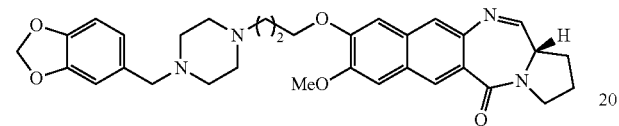 7h
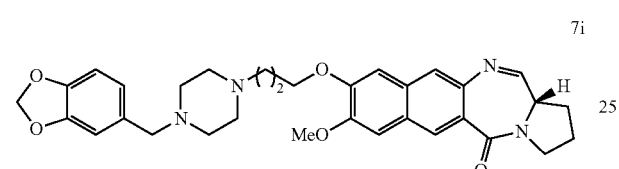 7i
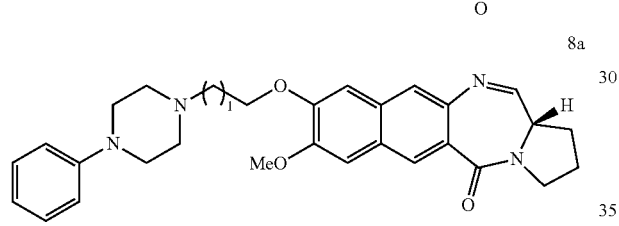 8a
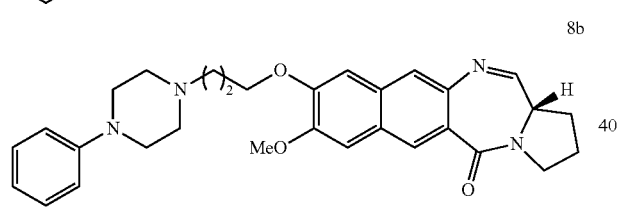 8b
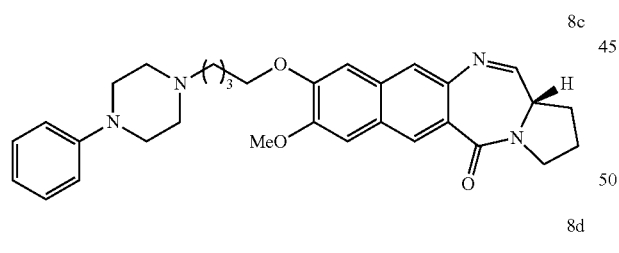 8c
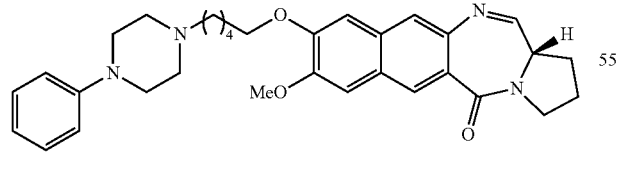 8d
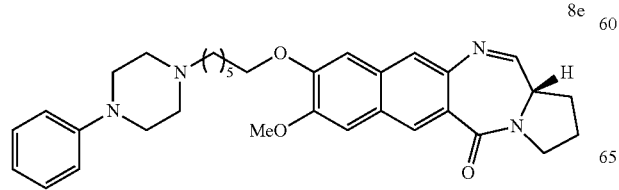 8e
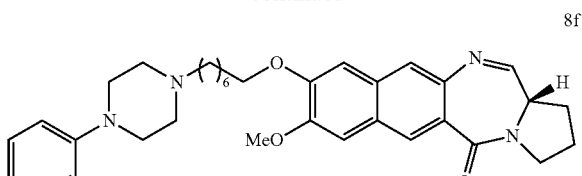 8f
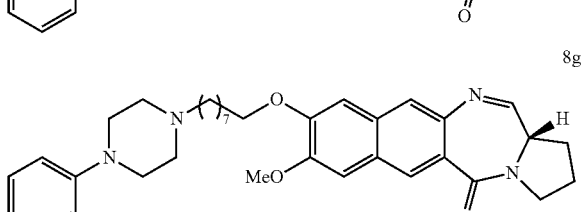 8g
 8h
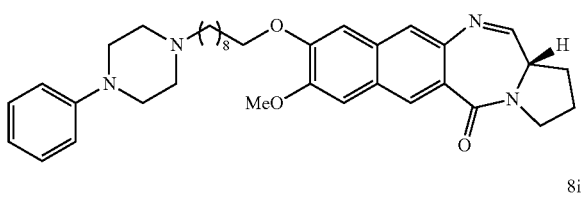 8i
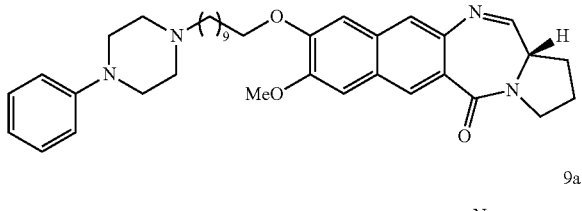 9a
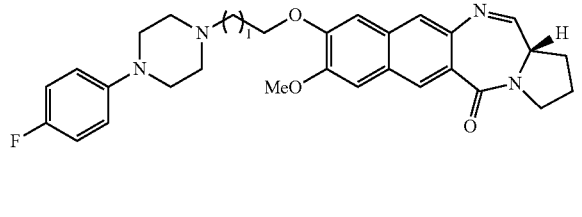 9b
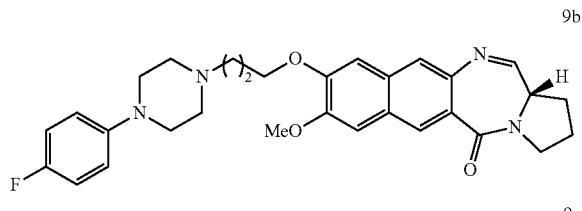 9c
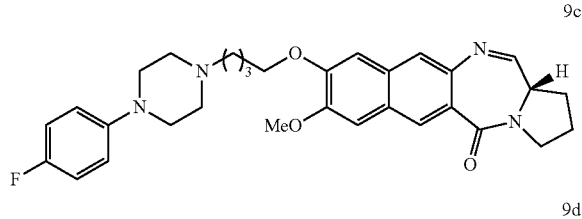 9d

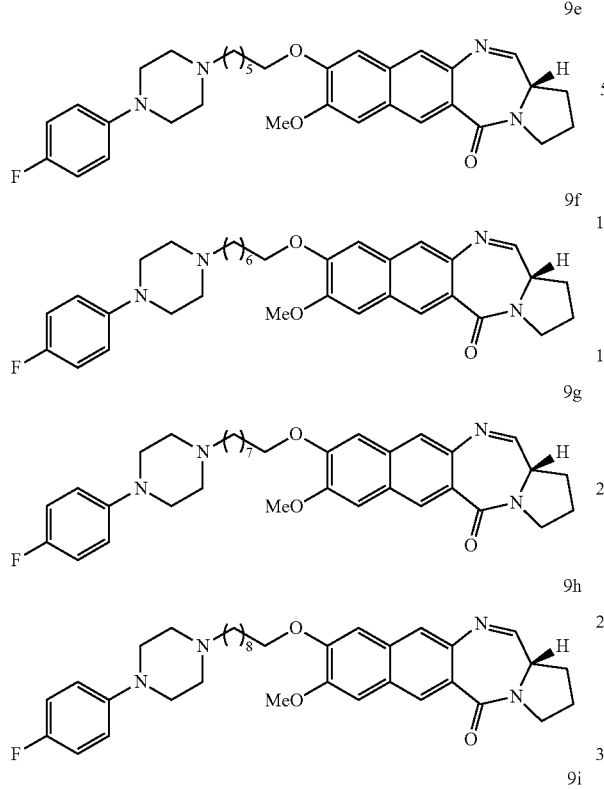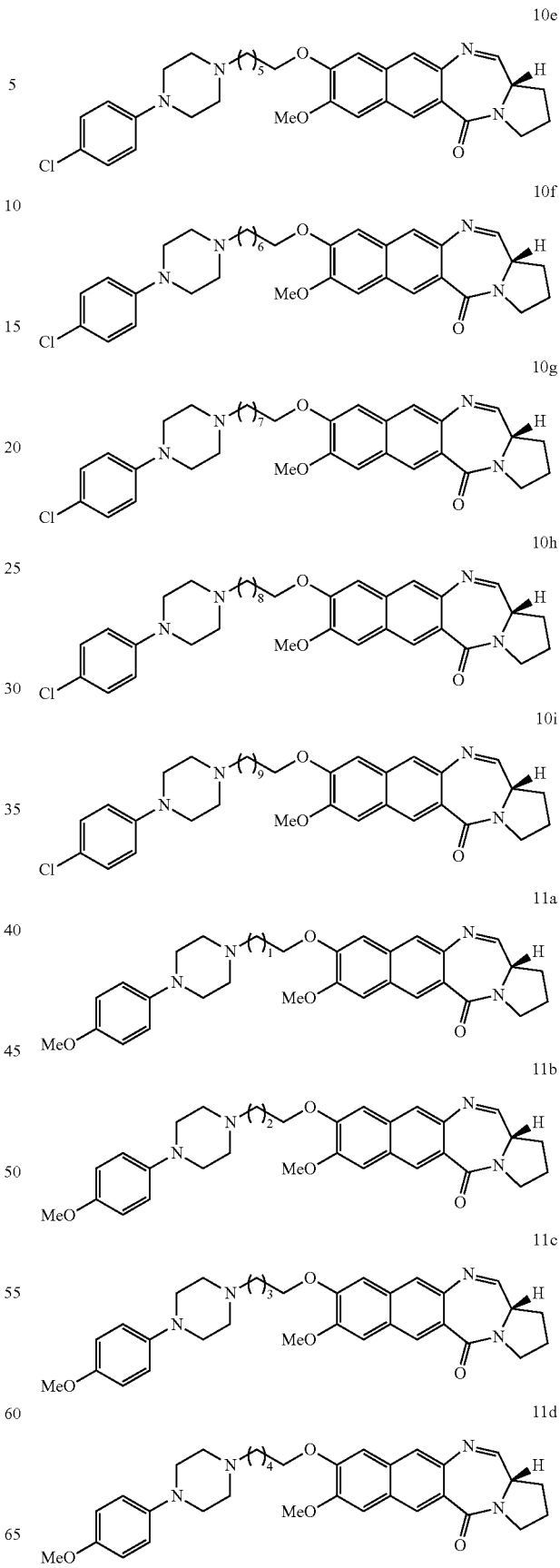

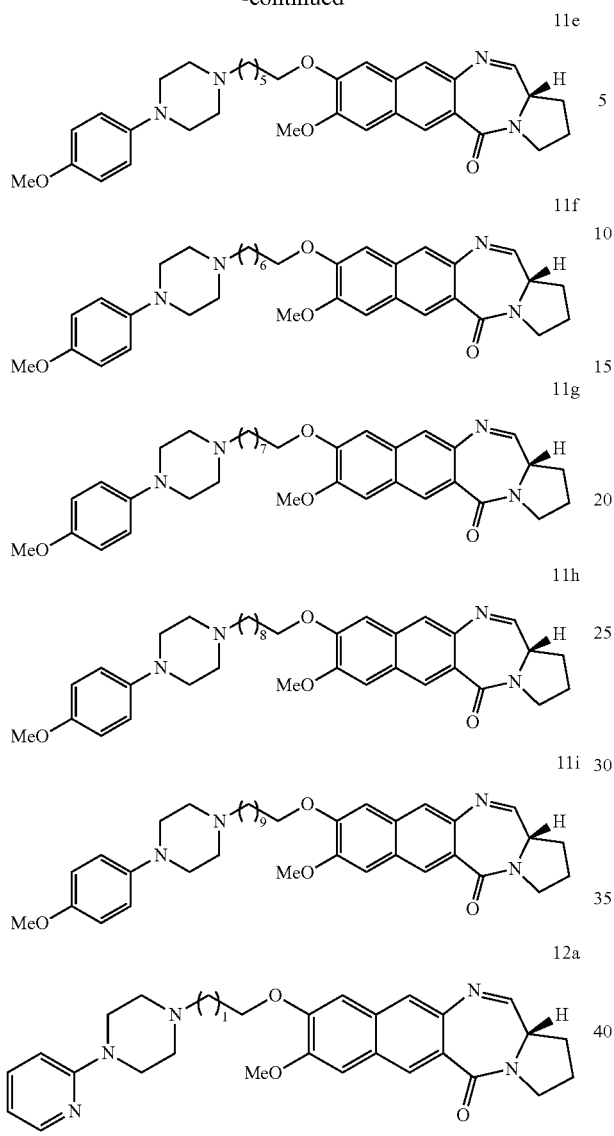
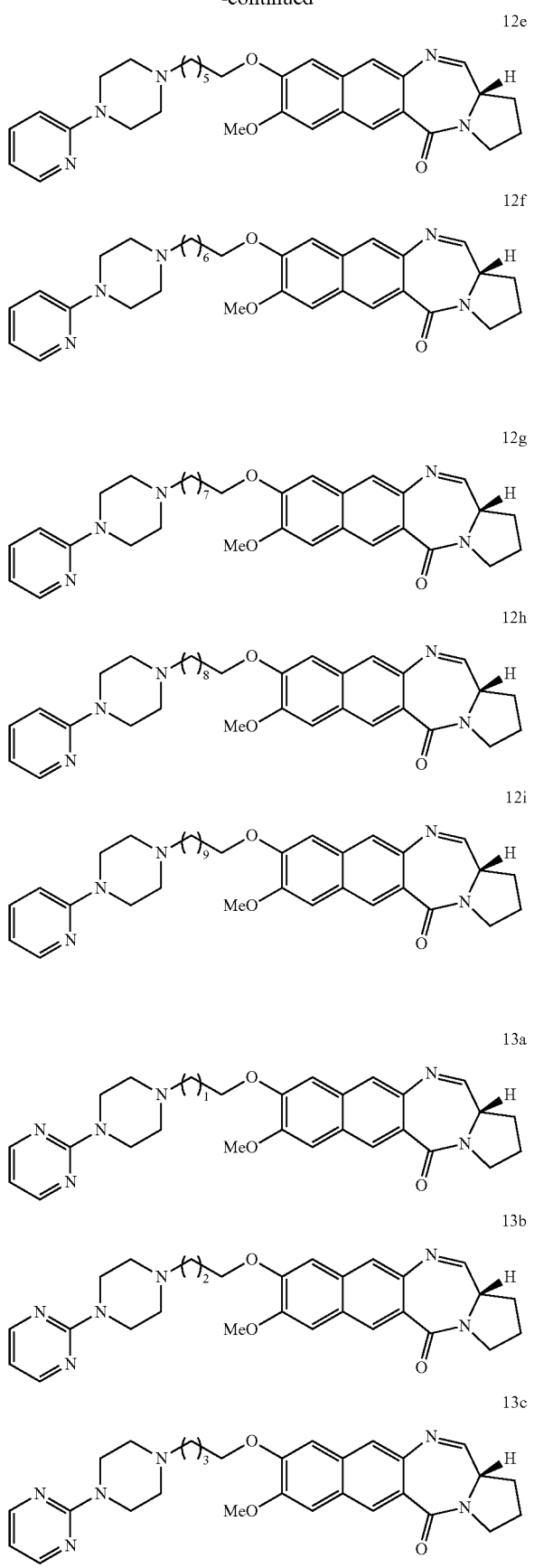

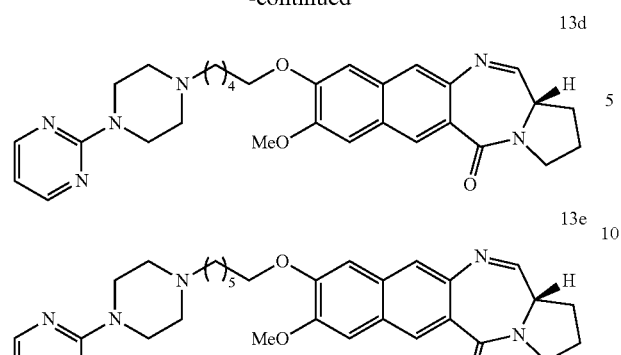
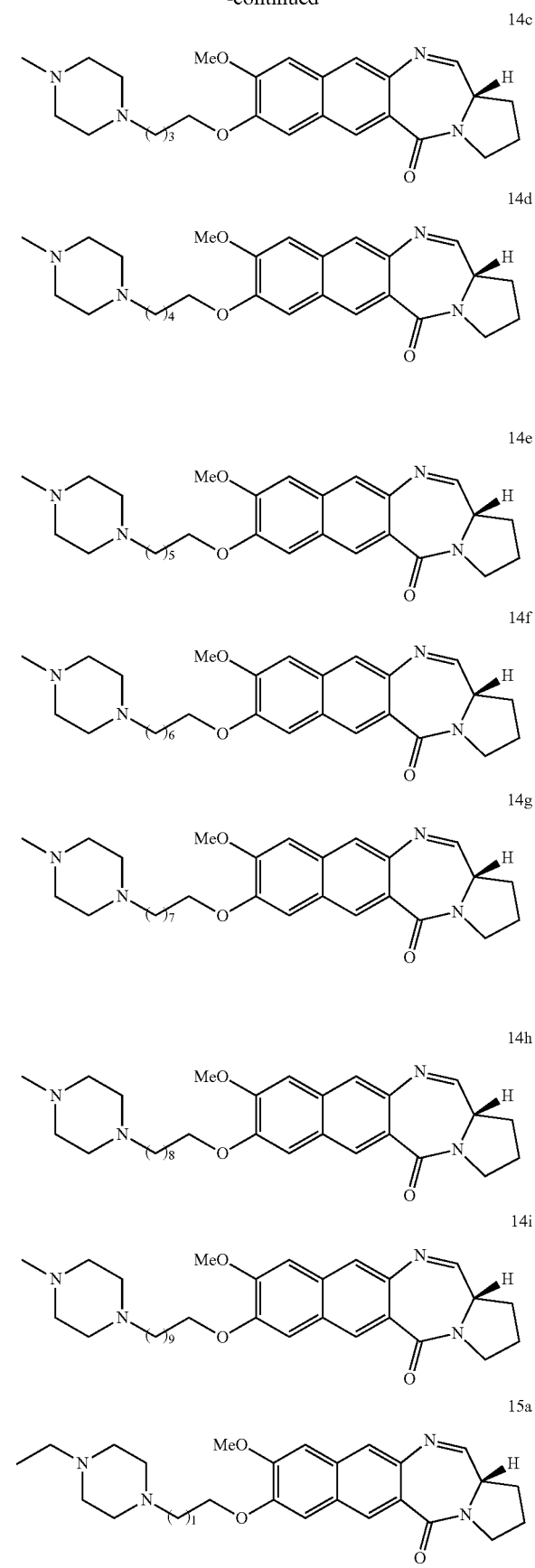

15b
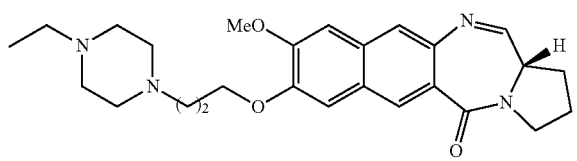
15c
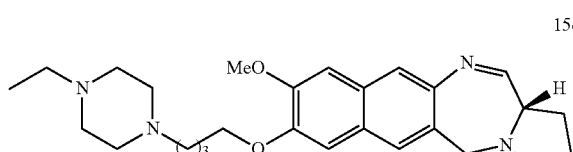
15d
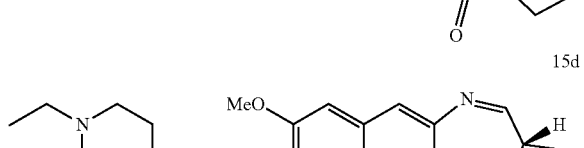
15e
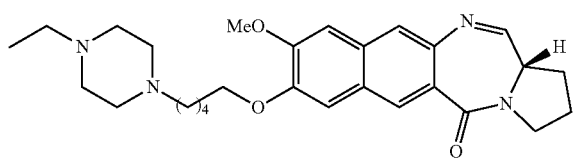
15f
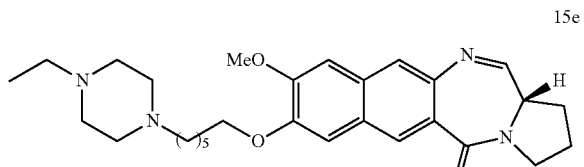
15g
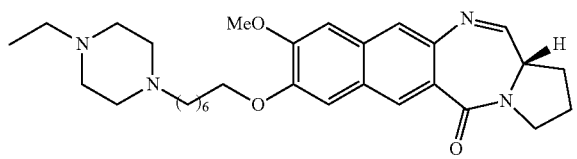
15h
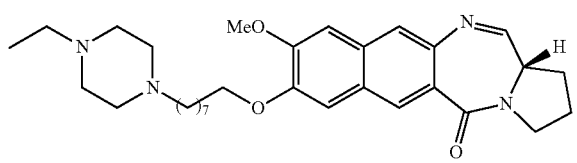
15i
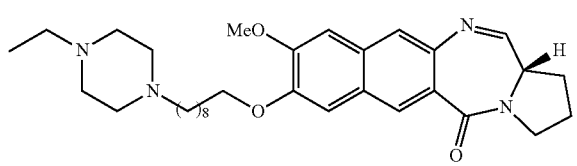
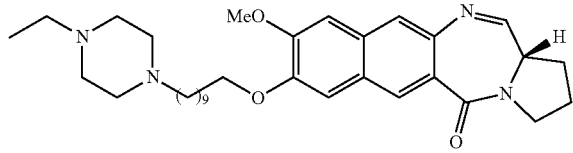
16a
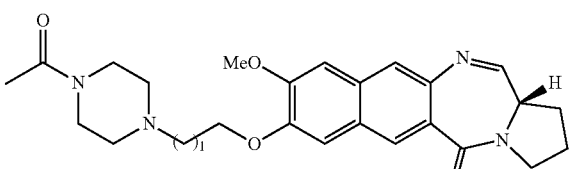
16b
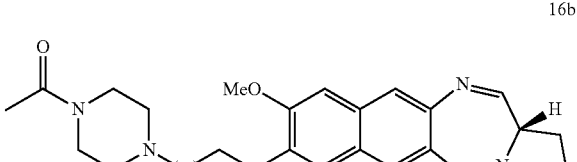
16c
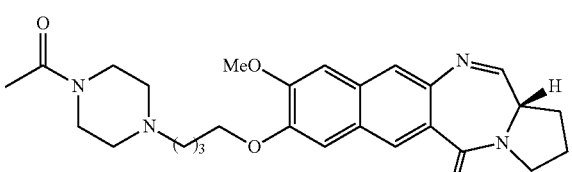
16d
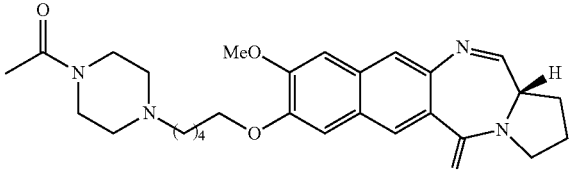
16e
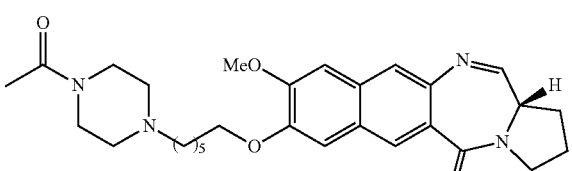
16f
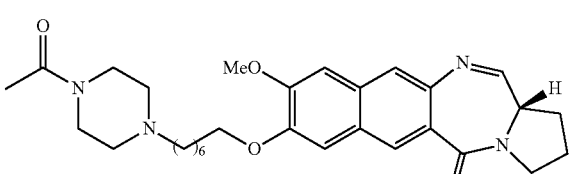
16g
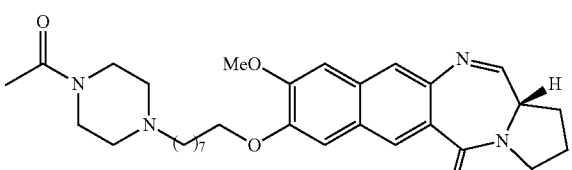

16h
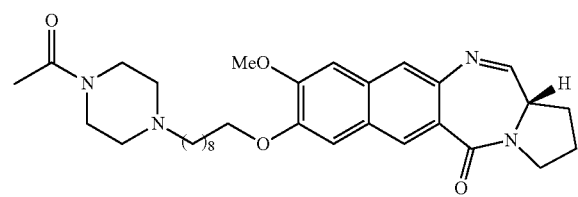
16i
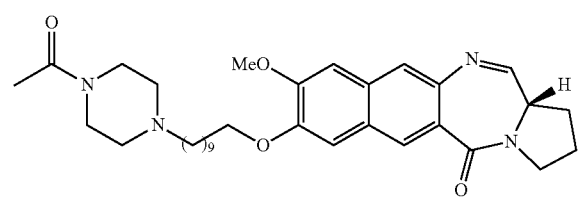
17a
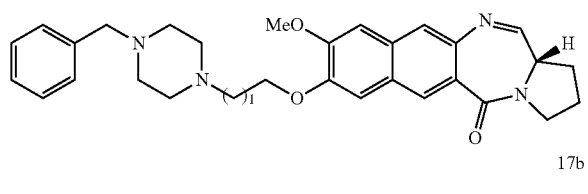
17b
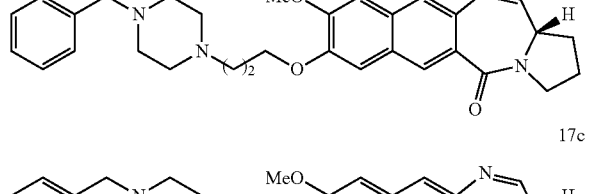
17c
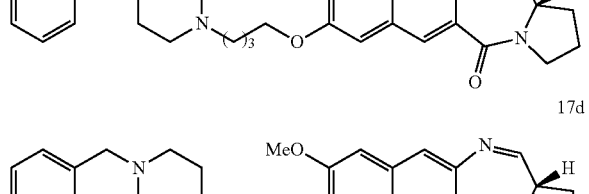
17d
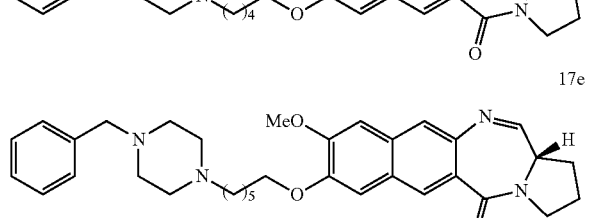
17e
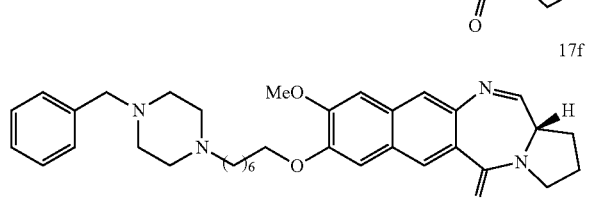
17f
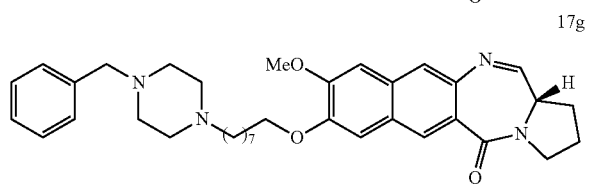
17g
17h
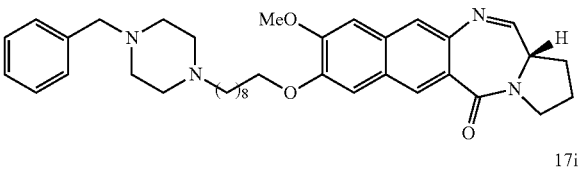
17i
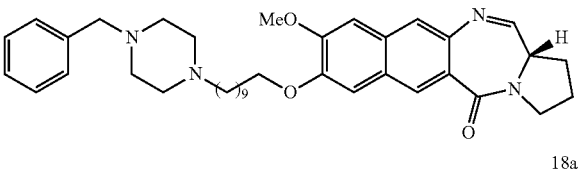
18a
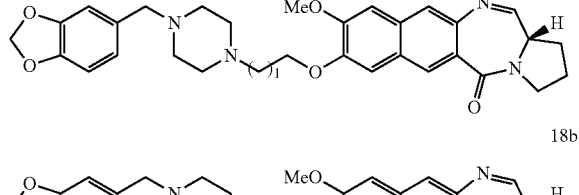
18b
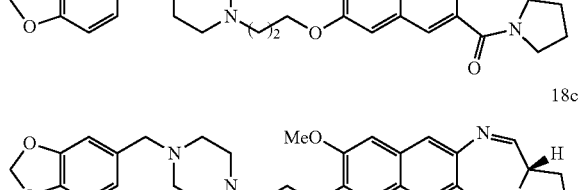
18c
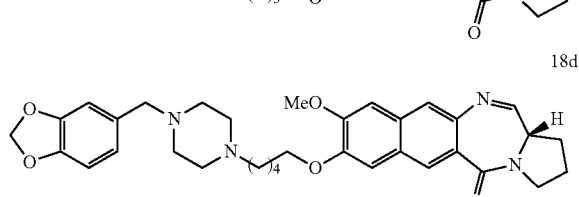
18d
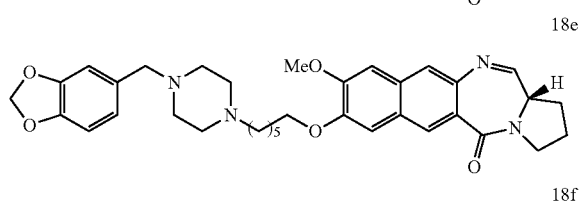
18e
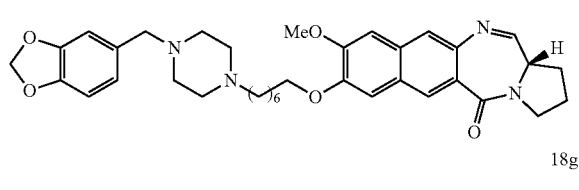
18f
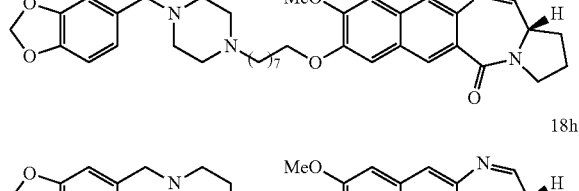
18g
18h
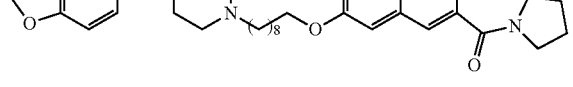

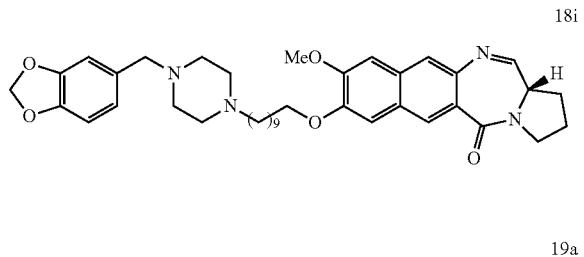
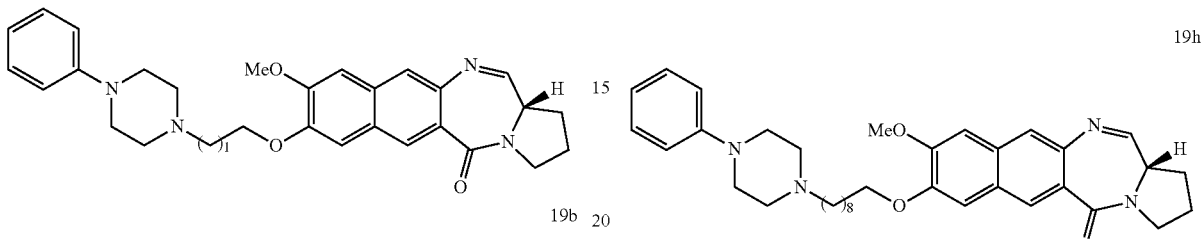
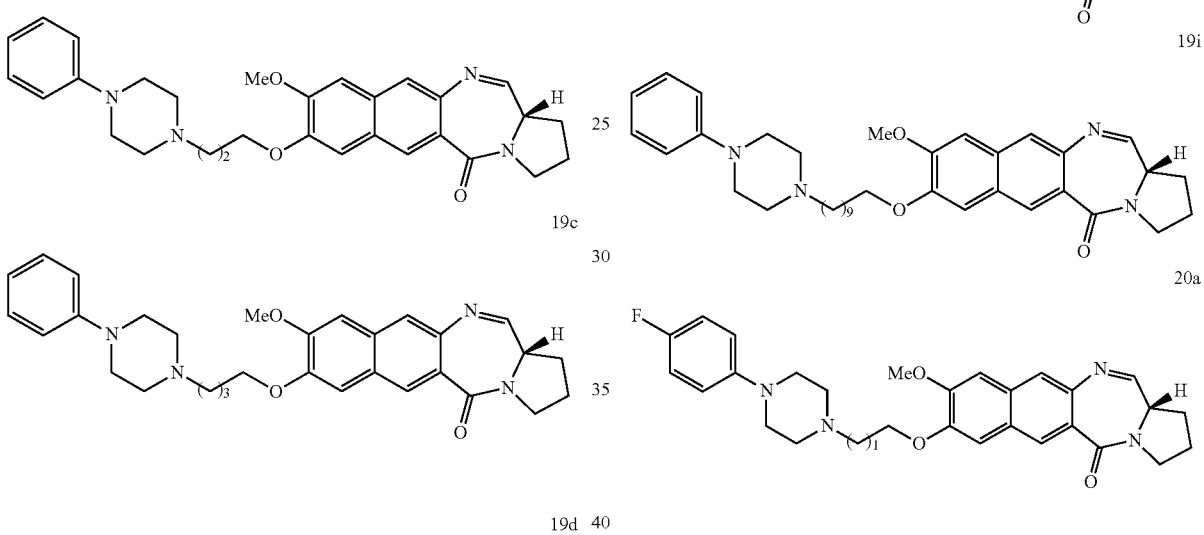
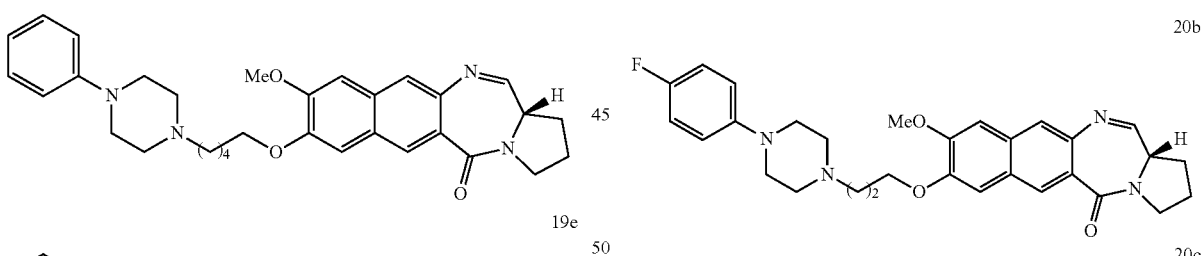
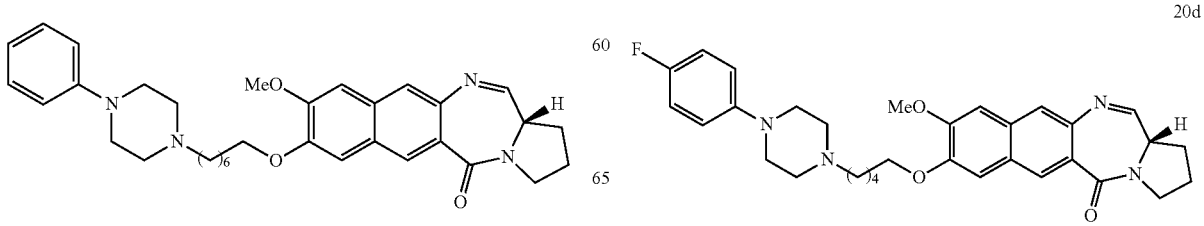

20e
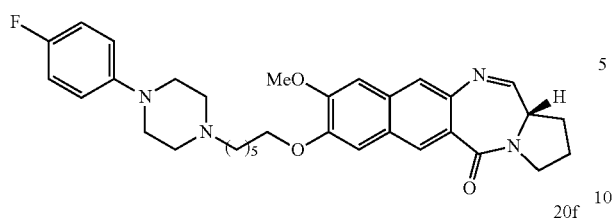
20f
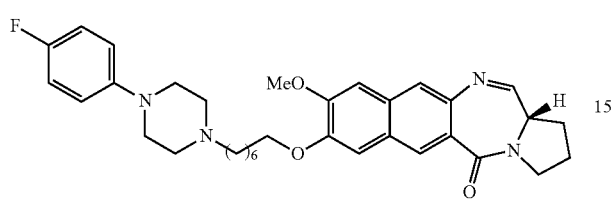
20g
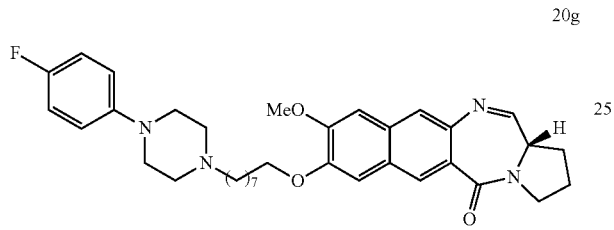
20h
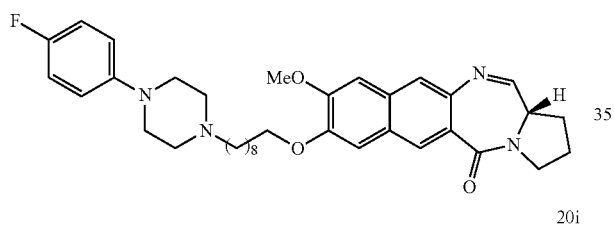
20i
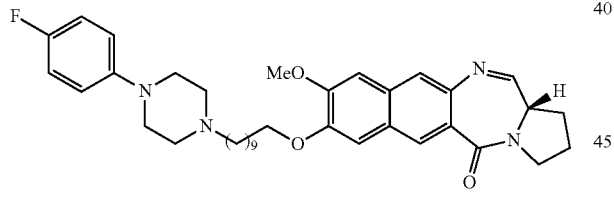
21a
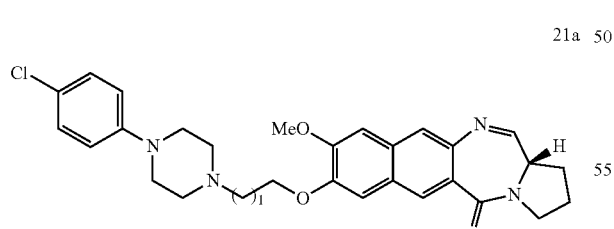
21b
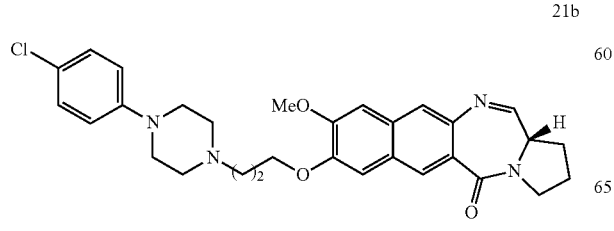
21c
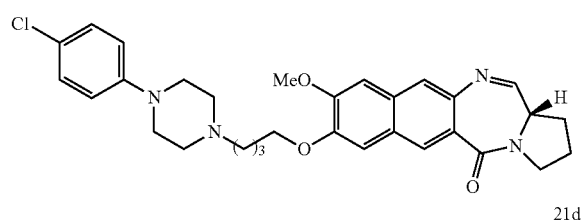
21d
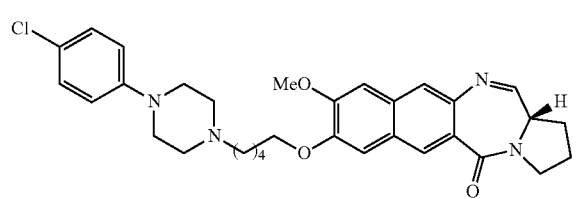
21e
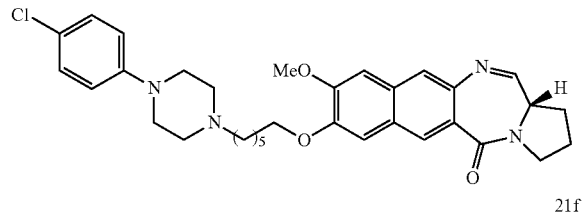
21f
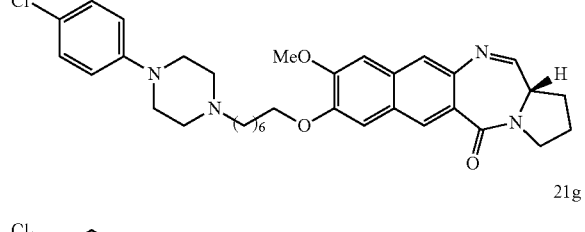
21g
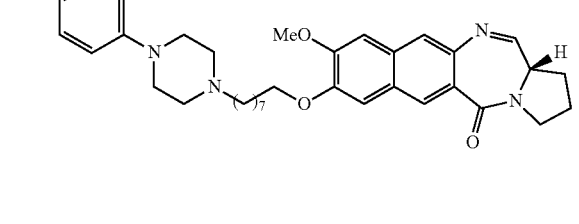
21h
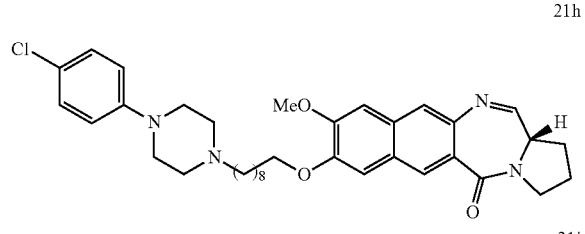
21i
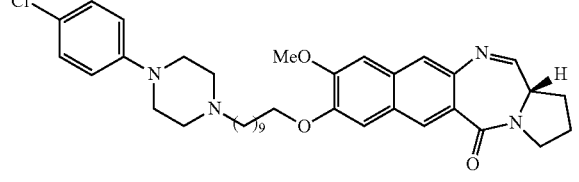

22a
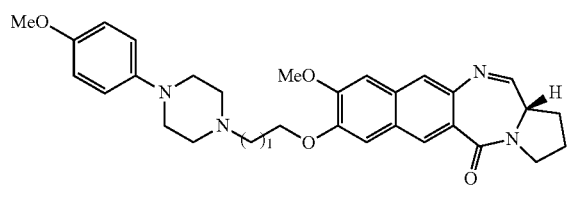
22b
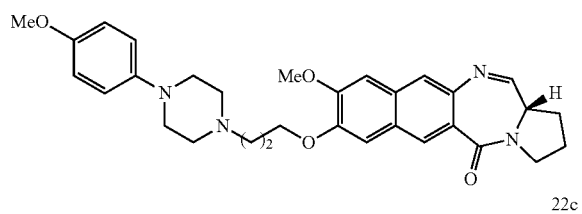
22c
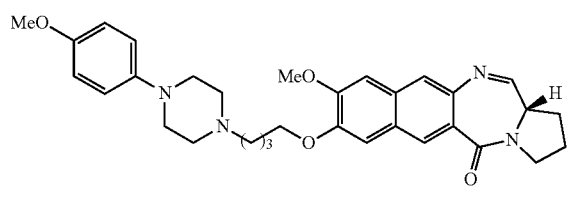
22d
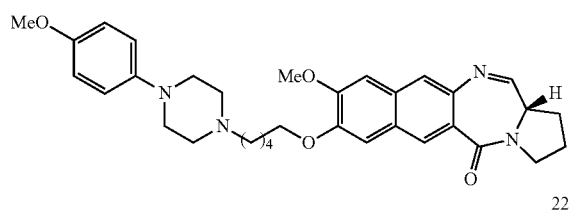
22e
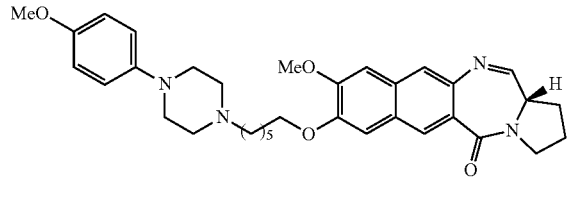
22f
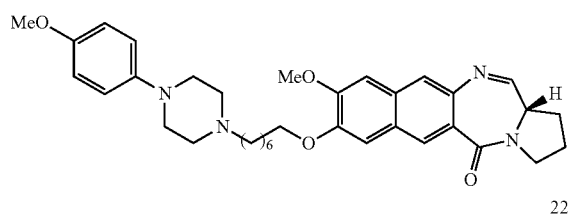
22g
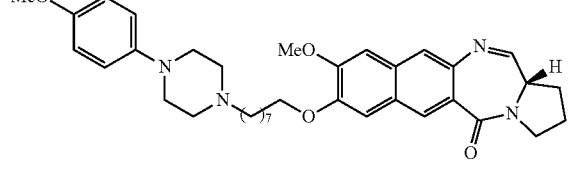
22h
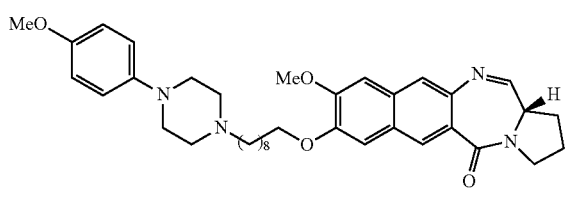
22i
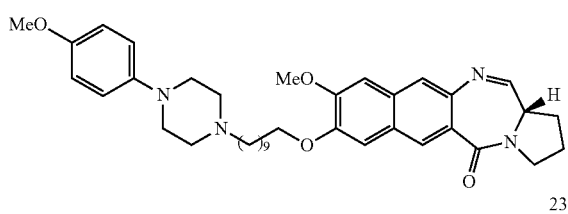
23a
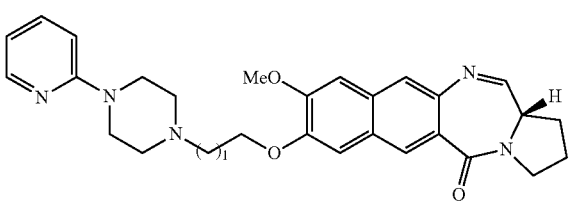
23b
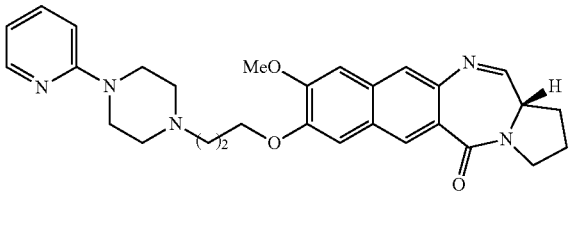
23c
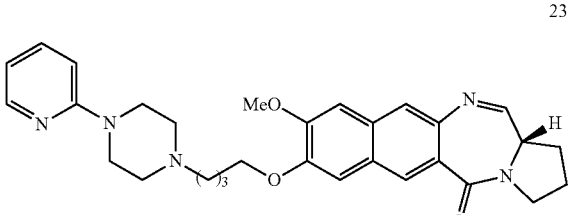
23d
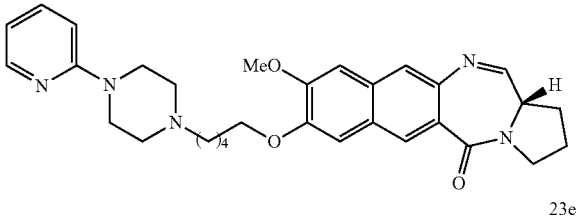
23e
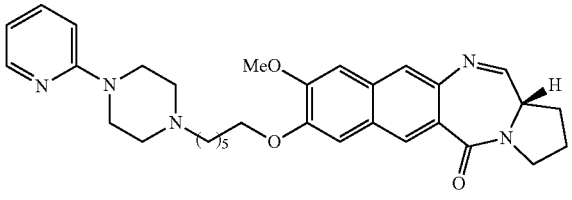

23f
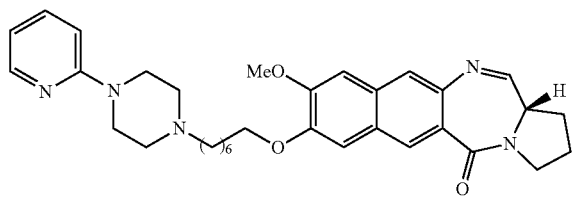

23g
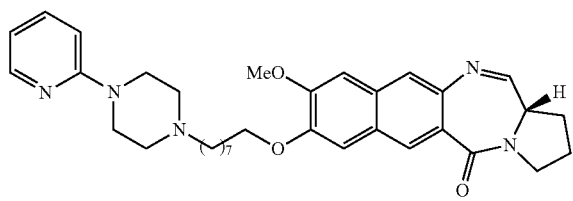

23h
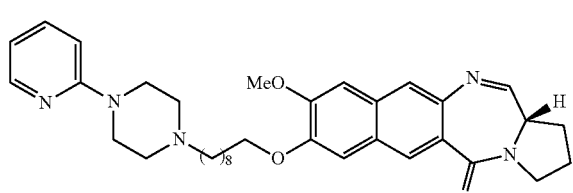

23i
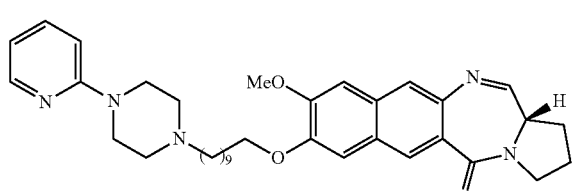

24a
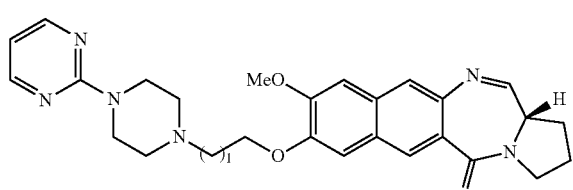

24b
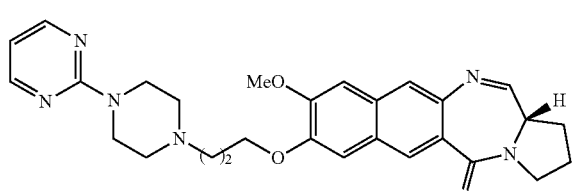

24c
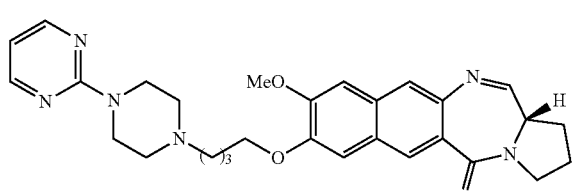

24d
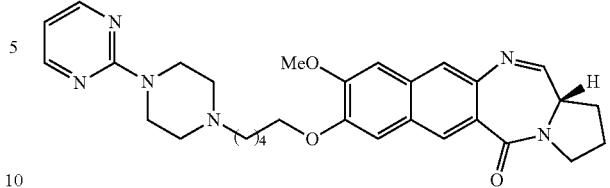

24e
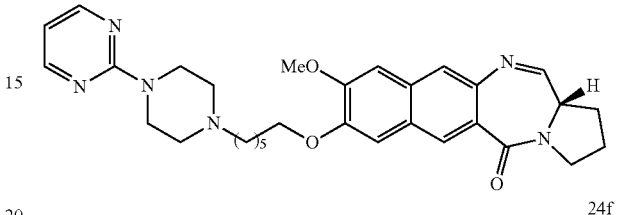

24f
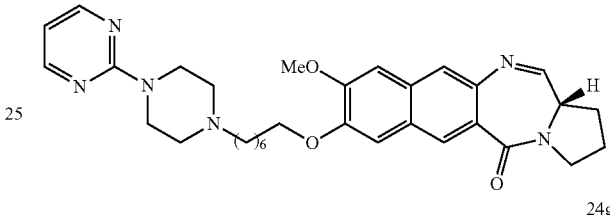

24g
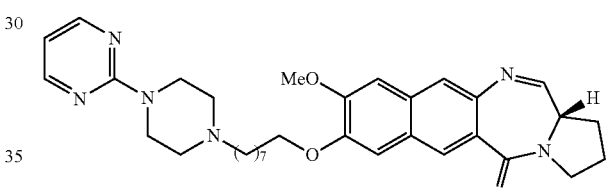

24h
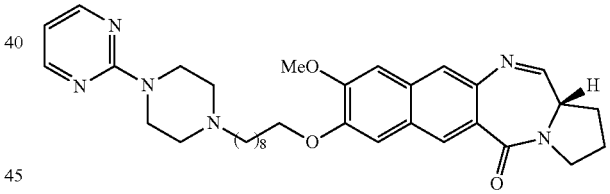

24i
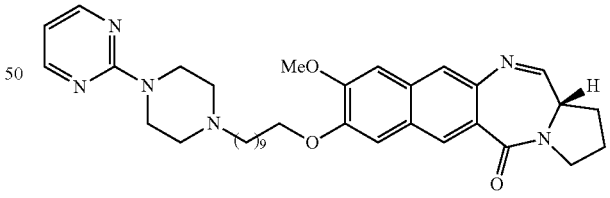

In another embodiment of the present invention, pyrrolo[2,1-c][1,4]naphthodiazepine linked substituted piperazine compound as claimed in claim 2, exhibiting Thermal denaturation ($\Delta T_m$) value in the range of 4.9 to 9.5° C. after incubation at 37° C. for 0 to 18 hrs.

In another embodiment of the present invention, pyrrolo[2,1-c][1,4]naphthodiazepine linked substituted piperazine compound 1a as claimed in claim 2 exhibiting in-vitro cytotoxicity in breast cancer cell line (MCF-7), lung cancer cell line (A549), liver cancer cell line (HEPG2), large cell lung cancer cell line (NCIH460), prostrate cancer cell line (PC-3), kidney cancer cell line (COS-1), small intestine cancer cell line (IEC-6) and skeletal cancer cell line (L-6).

In another embodiment of the present invention, pyrrolo[2,1-c][1,4]naphthodiazepine linked substituted piperazine compound 2a exhibiting in-vitro cytotoxicity in breast cancer cell line (MCF-7), lung cancer cell line (A549), liver cancer cell line (HEPG2), large cell lung cancer cell line (NCIH460), prostrate cancer cell line (PC-3), kidney cancer cell line (COS-1), small intestine cancer cell line (IEC-6) and skeletal cancer cell line (L-6).

In another embodiment of the present invention, pyrrolo[2,1-c][1,4]naphthodiazepine linked substituted piperazine compound 5a exhibiting in-vitro cytotoxicity in breast cancer cell line (MCF-7), lung cancer cell line (A549), liver cancer cell line (HEPG2), large cell lung cancer cell line (NCIH460), prostrate cancer cell line (PC-3) and skeletal cancer cell line (L-6).

In another embodiment of the present invention, pyrrolo[2,1-c][1,4]naphthodiazepine linked substituted piperazine compound 7a exhibiting in-vitro cytotoxicity in breast cancer cell line (MCF-7), lung cancer cell line (A549), liver cancer cell line (HEPG2), large cell lung cancer cell line (NCIH460), prostrate cancer cell line (PC-3), kidney cancer cell line (COS-1), small intestine cancer cell line (IEC-6) and skeletal cancer cell line (L-6).

In another embodiment of the present invention pyrrolo[2,1-c][1,4]naphthodiazepine linked substituted piperazine compound 8a exhibiting in-vitro cytotoxicity in breast cancer cell line (MCF-7), lung cancer cell line (A549), liver cancer cell line (HEPG2), large cell lung cancer cell line (NCIH460), prostrate cancer cell line (PC-3), kidney cancer cell line (COS-1), small intestine cancer cell line (IEC-6) and skeletal cancer cell line (L-6).

In another embodiment of the present invention, pyrrolo[2,1-c][1,4]naphthodiazepine linked substituted piperazine compound 12a exhibiting in-vitro cytotoxicity in breast cancer cell line (MCF-7), lung cancer cell line (A549), liver cancer cell line (HEPG2), large cell lung cancer cell line (NCIH460), prostrate cancer cell line (PC-3), kidney cancer cell line (COS-1), small intestine cancer cell line (IEC-6) and skeletal cancer cell line (L-6).

In another embodiment of the present invention, pyrrolo[2,1-c][1,4]naphthodiazepine linked substituted piperazine compound 13a exhibiting in-vitro cytotoxicity in breast cancer cell line (MCF-7), lung cancer cell line (A549), liver cancer cell line (HEPG2), large cell lung cancer cell line (NCIH460), prostrate cancer cell line (PC-3), kidney cancer cell line (COS-1), small intestine cancer cell line (IEC-6) and skeletal cancer cell line (L-6).

In another embodiment of the present invention, pyrrolo[2,1-c][1,4]naphthodiazepine linked substituted piperazine compound 15a exhibiting in-vitro cytotoxicity in breast cancer cell line (MCF-7), lung cancer cell line (A549), liver cancer cell line (HEPG2), large cell lung cancer cell line (NCIH460), prostrate cancer cell line (PC-3), kidney cancer cell line (COS-1), small intestine cancer cell line (IEC-6) and skeletal cancer cell line (L-6).

In another embodiment of the present invention, pyrrolo[2,1-c][1,4]naphthodiazepine linked substituted piperazine compound 19a exhibiting in-vitro cytotoxicity in breast cancer cell line (MCF-7), lung cancer cell line (A549), liver cancer cell line (HEPG2), large cell lung cancer cell line (NCIH460), prostrate cancer cell line (PC-3), kidney cancer cell line (COS-1), small intestine cancer cell line (IEC-6) and skeletal cancer cell line (L-6).

In another embodiment of the present invention, pyrrolo[2,1-c][1,4]naphthodiazepine linked substituted piperazine compound 20a exhibiting in-vitro cytotoxicity in breast cancer cell line (MCF-7), lung cancer cell line (A549), liver cancer cell line (HEPG2), large cell lung cancer cell line (NCIH460), prostate cancer cell line (PC-3), small intestine cancer cell line (IEC-6) and skeletal cancer cell line (L-6).

In another embodiment of the present invention, pyrrolo[2,1-c][1,4]naphthodiazepine linked substituted piperazine compound 23a exhibiting in-vitro cytotoxicity in breast cancer cell line (MCF-7), lung cancer cell line (A549), liver cancer cell line (HEPG2), large cell lung cancer cell line (NCIH460), prostrate cancer cell line (PC-3), kidney cancer cell line (COS-1), small intestine cancer cell line (IEC-6) and skeletal cancer cell line (L-6).

In another embodiment of the present invention, pyrrolo[2,1-c][1,4]naphthodiazepine linked substituted piperazine compound 24a exhibiting in-vitro cytotoxicity in breast cancer cell line (MCF-7), lung cancer cell line (A549), liver cancer cell line (HEPG2), large cell lung cancer cell line (NCIH460), prostate cancer cell line (PC-3), small intestine cancer cell line (IEC-6) and skeletal cancer cell line (L-6).

In another embodiment of the present invention, pyrrolo[2,1-c][1,4]naphthodiazepine linked substituted piperazine 1a, 2a, 5a, 7a, 8a, 12a, 13a, 15a, 19a, 20a, 23a and 24a as claimed in claim 2, wherein the concentration of the compound used for in vitro activity against breast cancer cell lines for $IC_{50}$ is in the range of 0.002-3.99 μm at an exposure period of at least 48 hrs.

In another embodiment of the present invention, pyrrolo[2,1-c][1,4]naphthodiazepine linked substituted piperazine 1a, 2a, 5a, 7a, 8a, 12a, 13a, 15a, 19a, 20a, 23a and 24a as claimed in claim 2, wherein the concentration of the compound used for in vitro activity against lung cancer cell lines for $IC_{50}$ is in the range of 0.02-11.92 μm at an exposure period of at least 48 hrs.

In another embodiment of the present invention, pyrrolo[2,1-c][1,4]naphthodiazepine linked substituted piperazine 1a, 2a, 5a, 7a, 8a, 12a, 13a, 15a, 19a, 20a, 23a and 24a as claimed in claim 2, wherein the concentration of the compound used for in vitro activity against liver cancer cell lines for $IC_{50}$ is in the range of 0.02-7.32 μm at an exposure period of at least 48 hrs.

In another embodiment of the present invention, pyrrolo[2,1-c][1,4]naphthodiazepine linked substituted piperazine 1a, 2a, 5a, 7a, 8a, 12a, 13a, 15a, 19a, 20a, 23a and 24a as claimed in claim 2, wherein the concentration of the compound used for in vitro activity against large cell lung cancer cell lines for $IC_{40}$ is in the range of 0.002-1.68 μm at an exposure period of at least 48 hrs.

In another embodiment of the present invention, pyrrolo[2,1-c][1,4]naphthodiazepine linked substituted piperazine 1a, 2a, 5a, 7a, 8a, 12a, 13a, 15a, 19a, 20a, 23a and 24a as claimed in claim 2, wherein the concentration of the compound used for in vitro activity against prostate cancer cell lines for $IC_{50}$ is in the range of 0.01-13.5 μm at an exposure period of at least 48 hrs.

In another embodiment of the present invention, pyrrolo[2,1-c][1,4]naphthodiazepine linked substituted piperazine 1a, 2a, 5a, 7a, 8a, 12a, 13a, 15a, 19a, 20a, 23a and 24a as claimed in claim 2, wherein the concentration of the compound used for in vitro activity against kidney cancer cell lines for $IC_{50}$ is in the range of 0.80-4.32 μm at an exposure period of at least 48 hrs.

In another embodiment of the present invention, pyrrolo[2,1-c][1,4]naphthodiazepine linked substituted piperazine 1a, 2a, 5a, 7a, 8a, 12a, 13a, 15a, 19a, 20a, 23a and 24a as claimed in claim 2, wherein the concentration of the compound used for in vitro activity against small intestine cancer cell lines for $IC_{50}$ is in the range of 0.01-5.84 μm at an exposure period of at least 48 hrs.

In another embodiment of the present invention, pyrrolo[2,1-c][1,4]naphthodiazepine linked substituted piperazine 1a, 2a, 5a, 7a, 8a, 12a, 13a, 15a, 19a, 20a, 23a and 24a as claimed in claim 2, wherein the concentration of the compound used for in vitro activity against skeletal cancer cell lines for $IC_{50}$ is in the range of 0.002-2.66 μm at an exposure period of at least 48 hrs.

In another embodiment of the present invention, a process for the preparation of Pyrrolo[2,1-c][1,4]naphthodiazepine linked substituted piperazine compounds of general formula A as claimed in claim 1 wherein the said process comprising the steps of:

a. reacting compound of formula 27a or 27b with $LiOH.H_2O$ in $THF:MeOH:H_2O$ (4:1:1) at temperature ranging between 27 to 30° C. for a period ranging between 4 to 6 h to obtain compound of general formula 28a or 28b respectively.

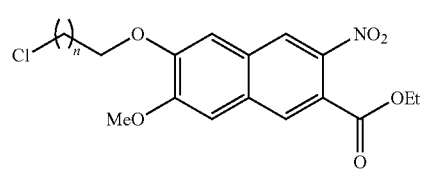

27a

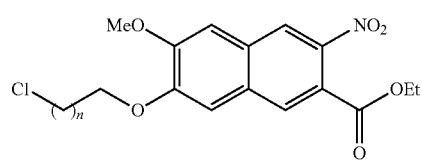

27b

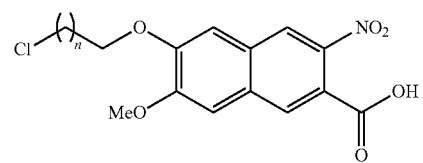

28a

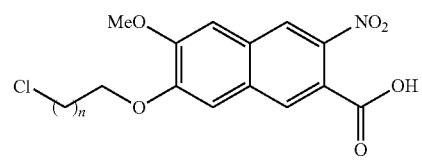

28b b. reacting compounds of formula 28a or 28b as obtained in step (a) with $SOCl_2$ in benzene at temperature ranging between 27 to 30° C. for a period ranging between 6 to 8 h and followed by coupling with (S)-methylpyrrolidine-2-carboxylate in THF at temperature ranging between 0 to 5° C. to obtain compound of general formula 29a or 29b respectively.

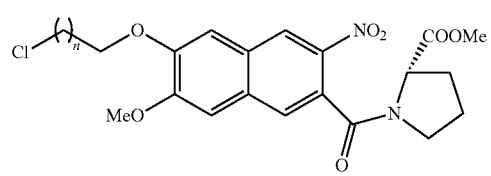

29a

-continued

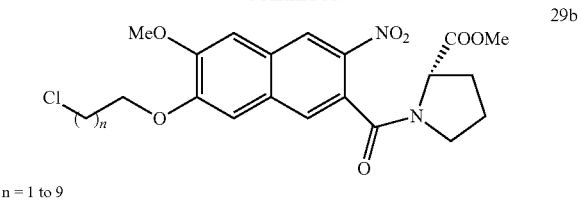

29b n = 1 to 9 c. reacting compounds of formula 29a or 29b as obtained in step (b) with DIABAL-H (diisobutylaluminiumhydride) in dichloromethane (DCM) solvent at temperature ranging between −60 to −78° C. for a period ranging between 30 to 40 min and protecting with EtSH (ethanethiol) and TMSCl (trimethylsilylchloride) at temperature ranging between 27 to 30° C. for a period ranging between 8 to 12 h to obtain compounds of general formula 30a or 30b respectively.

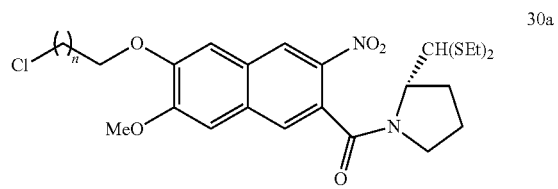

30a

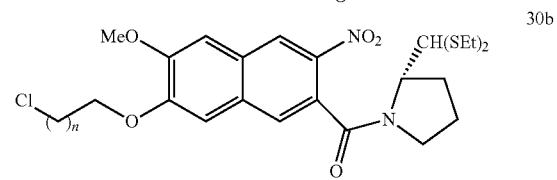

30b n = 1 to 9 d. reacting compounds of formula 30a or 30b as obtained in step (c) with substituted piperazines in mole ratio ranging between 1:5 to 1:10 at temperature ranging between 100 to 120° C. for a period ranging between to obtain nitro compounds of general formula 32a or 32b respectively.

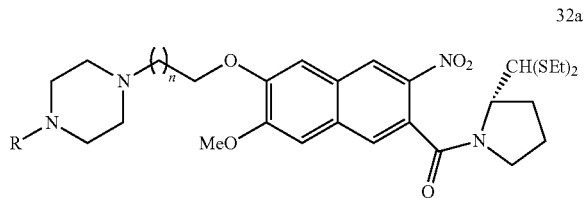

32a

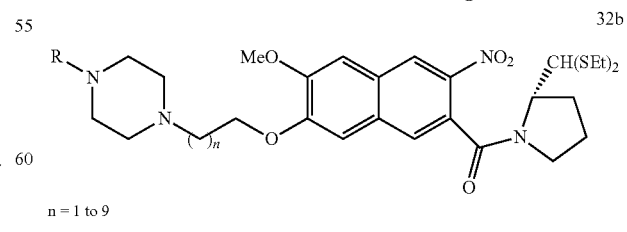

32b n = 1 to 9 e. reducing nitro compound of general formula 30a or 30b or 32a or 32b as obtained in step (c) or (d) with $SnCl_2.2H_2O$ in methanol solvent at temperature range of 65 to 70° C. for a period ranging between 3 to 5 h to obtain amino compound of general formula 31a or 31b or 33a or 33b respectively.

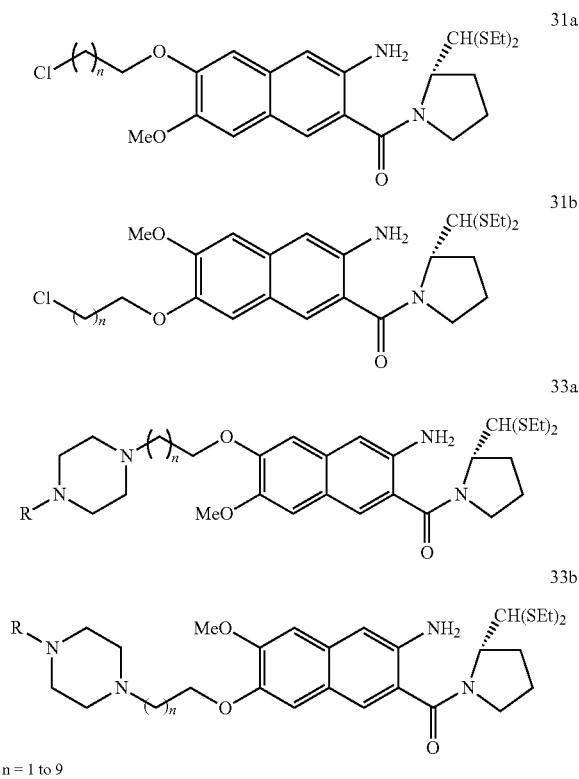

n = 1 to 9 f. reacting the amino compound of formula 31a or 31b or 33a or 33b as obtained in step (e) with a deprotecting agent HgCl$_2$ and CaCO$_3$ in MeCN:H$_2$O (4:1 ratio) at temperature ranging between 27 to 30° C. for a period ranging between 12 to 24 h to obtain the desired compound of formula 1a-i to 24a-i.

In another embodiment of the present invention, a process as claimed in claim 25, wherein substituted piperazines used in step (f) is selected from the group consisting of 1-acetyl piperazine, 1-piperinoyl piperazine, 1-phenyl piperazine, 1-pyridyl piperazine, 1-pyrimidyl piperazine, 1-ethyl piperazine, 1-(4-fluorophenyl)piperazine, 1-benzyl piperazine, 1-(4-chlorophenyl)piperazine and 1-(4-methoxyphenyl)piperazine. In another embodiment of the present invention, a process as claimed in claim 25, wherein yield of compound of formula A is in the range of 55-75%.

DETAILED DESCRIPTION OF THE INVENTION

Figure 1:
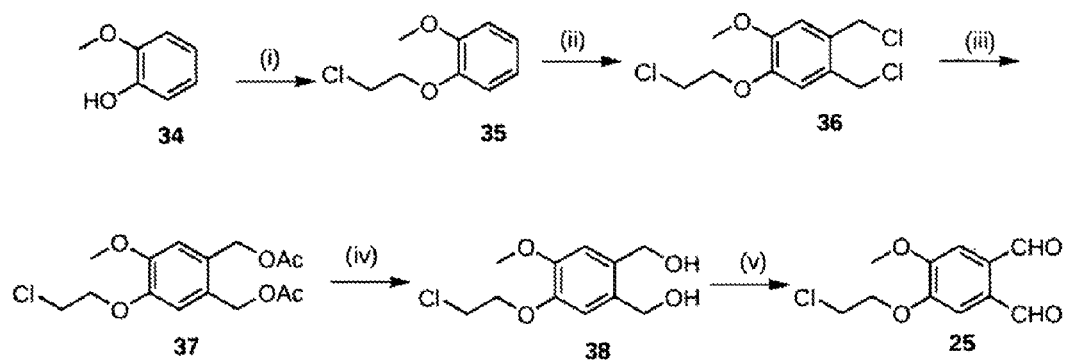
FIG. 1 Scheme 1 represent schematic diagram for the preparation of compound 25, wherein reagent and conditions are (i) 1,2-dichloroethane, KOH, reflux, 24 h; (ii) HCHO, HCl gas, 0° C., 6 h; (iii) AcOH, NaOAc, 2 h, reflux; (iv) NH$_3$ gas, MeOH, 2 h, 0° C., (v) dry DMSO, (COCl)$_2$, −78° C., 2 h.
Figure 2:
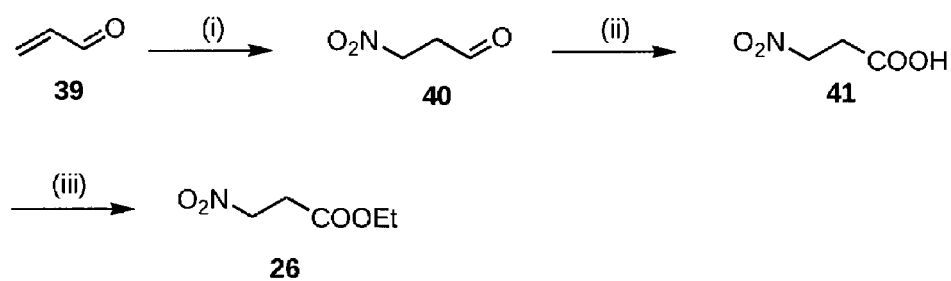
FIG. 2 Scheme 2 represent schematic diagram for the preparation of compound 26, wherein reagent and conditions are (i) NaNO$_2$, AcOH, 0° C., 3 h; (ii) Acetonitrile, NaClO$_2$, NaH$_2$PO$_4$, H$_2$O$_2$, 0° C., 1 h; (iii) AcOH, NaOAc, 2 h, reflux.
Figure 3:
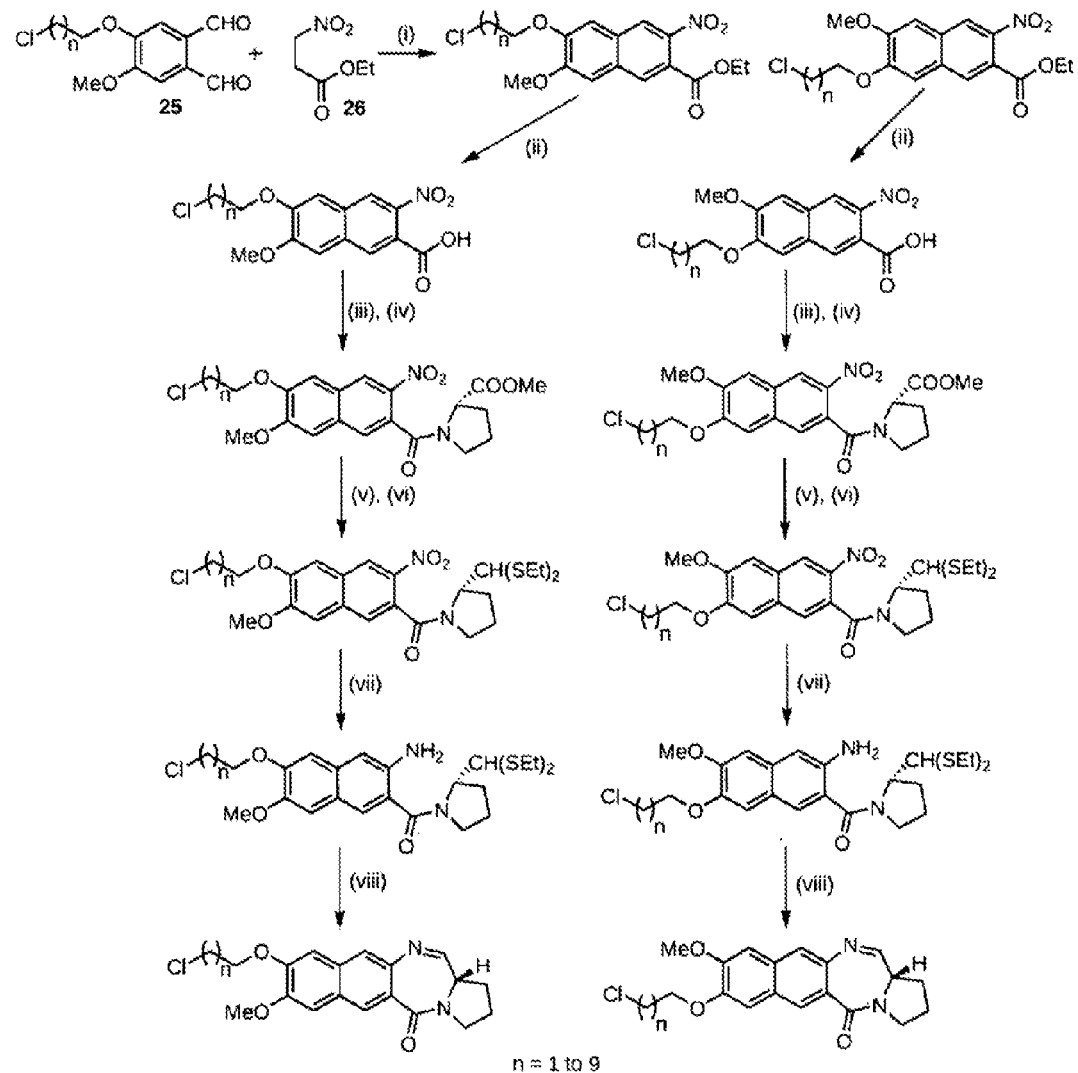
FIG. 3 Scheme 3 represent schematic diagram for the preparation of compound of general formula 1 wherein reagent and conditions are (i) NaOEt, CH$_2$Cl$_2$, 0° C., 2 h; (ii) LiOH.H$_2$O, THF:MeOH:H$_2$O (3:1:1) 27° C., 4 h; (iii) SOCl$_2$, benzene, 27° C., 12 h; (iv) N(Et)$_3$, THF, 0° C., 1 h; (v) DIBAL-H, CH$_2$Cl$_2$, −78° C., 40 min; (vi) EtSH, TMSCI, CH$_2$Cl$_2$, 27° C., 12 h; (vii) SnCl$_2$.2H$_2$O, MeOH, 2 h, reflux; (viii) HgCl$_2$—CaCO$_3$, MeCN—H$_2$O (4:1), 12 h, 27° C.
Figure 4:
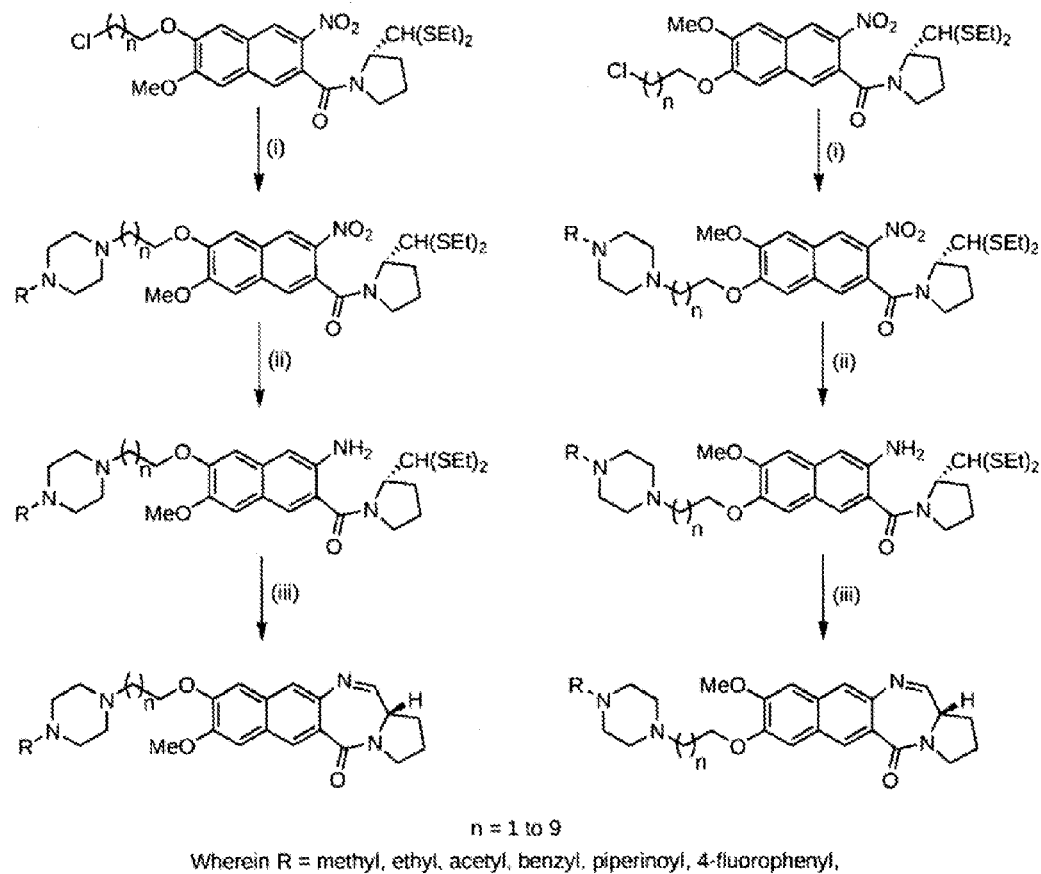
FIG. 4 Scheme 4 represent schematic diagram for the preparation of compound of general formula 1 wherein reagent and conditions are (i) substituted piperazine, K$_2$CO$_3$, 120° C., 1 h; (ii) SnCl$_2$.2H$_2$O, MeOH, 2 h, reflux; (iii) HgCl$_2$—CaCO$_3$, MeCN—H$_2$O (4:1), 12 h, 27° C.

The precursors ethyl 6-(2-chloroethoxy)-7-methoxy-3-nitro-2-naphthoate and ethyl 6-(2-chloroethoxy)-7-methoxy-3-nitro-2-naphthoate of formula 27a,b (Berger et al. *J. Med. Chem.*, 2005, 48, 5909. have been synthesized by known literature methods.

These new analogues 1a-i to 24a-i of pyrrolo[2,1-c][1,4] naphthodiazepine hybrids linked at C-8 and C-9 position have shown promising DNA binding activity and efficient anticancer activity in various cell lines. The molecules synthesized are of massive biological significance with potential sequence selective DNA-binding property and cytotoxicity. This present invention is illustrated in Scheme 1 and 2 as herein given below:

1) Synthesis of C-8 and C-9 linked pyrrolonaphthodiazepine antitumour antibiotic hybrid imines.
2) Purification by column chromatography using different solvents like ethyl acetate, hexane, chloroform and methanol.

EXAMPLES

The following examples are given by way of illustration of the working of the invention in actual practice and therefore should not be construed to limit the scope of present invention.

Example 1

8-Methoxy-9-(2-chloroethoxy)-(13aS)-1,2,3,13a-tetrahdro-5H-pyrrolo[2,1-c][1,4]naphthodiazepine-5-one (1a)

To a solution of freshly distilled 3.34 mL of acrolein (39) and 5.2 gr of NaNO$_2$ in a 20 mL of THF added 3.58 mL of AcOH at 0° C. drop wise over 1 h with vigorous stirring. Addition must be slow otherwise brown vapours of Nitrous oxide developed. Then 10 mL water was added to dissolve the suspended salts. Organic layer was separated and extracted with dichloromethane (4×10 ml) Wash the organic solutes with saturated sodium bicarbonate solution (2×15 ml), saturated sodium chloride (2×10 mL) and water (1×10 mL). the solution was dried overnight with MgSO$_4$. Filtration and removal of the solvents at 40 torr gives pale yellow liquid 3-nitropropanaldehyde (40) with boiling point 60° C. at 2.5 torr. Yield 3.2 gr (63%).

To a solution of 6.6 gr of 3-nitropropanaldehyde (40) in 50 mL of acetonitrile, 1.6 gr of sodium dihydrogenphosphate in 20 mL of water and 5 mL of H$_2$O$_2$ was added a solution of 8 gr or sodium chlorite in 70 mL of water dropwise over 2 h at 0° C. Then stirring was continued for 1 h at room temperature. Add about 0.5 gr of sodium sulphite and stir to destroy the unreacted H$_2$O$_2$ and HOCl. Then add water, acidified with 10% Aq HCl and extracted with ethyl acetate (2×50 ml). To the aqueous phase solid NaCl was added and again extracted with ethyl acetate (3×50 mL). The solution was dried with $Na_2SO_4$ and concentrated gives yellow viscous oil. Purification from the column chromatography gives 3-nitropropionic acid (41) as a white solid. Yield 7.3 gr (96%).

To a solution of 2 gr of 3-nitropropionic acid (41) in 30 mL of ethanol add catalytic amount of concentrated sulphuric acid (0.8 mL) and reflux overnight. Then add water and extracted with ethylacetate. The organic layer was washed with saturated sodium bicarbonate solution, saturated sodium chloride and water. Purification from column gives ethyl 3-nitropropionic acid (26) as pale yellow liquid with boiling point 92° C. at 2.5 torr.

A mixture of 52.88 g (0.426 mol) of guaiacol (34), 50 ml (0.426 mol) of 1,2-dichloroethane, 88.3 g (0.639 mol) of potassium hydroxide and heated at reflux for 24 h. The mixture was concentrated and extracted into ethyl acetate and evaporate the solvent and purified by column chromatography to gave 41.47 g (52%) of 1-(2-Chloroethoxy)-2-methoxy benzene (35) as a white solid, mp 42-43° C.

To a solution of 55.99 g (300 mmol) of 35 in 250 mL of 1,4-dioxane was added 40 mL of concentrated hydrochloric acid while stirring at 0° C. While HCl gas was bubbled in, 30 mL of 35% formalin was added. After 45 min, another equal volume of formalin was added. The addition of HCl gas was continued for 6 h, and the ice bath was removed after 2 h and allowed to warm to ambient temperature. The reaction mixture was stirred overnight at ambient temperature. The green reaction mixture was then cooled in an ice bath, and the resulting solid was filtered and washed with cold dioxane/water (2.5:1). Silica gel chromatography of the crude solid, eluting with 2:1 hexanes/dichloromethane, provided 36.35 g (42%) of 1-(2-Chloroethoxy)-4,5-bis(chloromethyl)-2-methoxy benzene (36) as a white solid, mp 117-118° C.

To a solution of 5.67 g (20 mmol) of 36 in 75 mL of acetic acid was added a solution of 3.5 g of anhydrous sodium acetate (42.7 mmol) in 100 mL of acetic acid. This mixture was refluxed with stirring for 2 h. Solids were removed by filtration and washed with acetic acid. The filtrate was evaporated to approximately 30 mL, then poured into water and extracted with ether. The organic phase was washed with aqueous sodium carbonate, water, and brine. After drying over sodium sulfate, the solution was filtered and evaporated to give 5.69 g (86%) of 2-[(acetyloxy)methyl]-4-(2-chloroethoxy)-5-methoxybenzyl acetate (37) as a white solid, mp 79-80° C.

A solution of 14.0 g of the 2-[(acetyloxy)methyl]-4-(2-chloroethoxy)-5-methoxybenzyl acetate (42.3 mmol) (37) in 600 mL of methanol was stirred and cooled in an ice bath while ammonia gas was bubbled in, until the solution was saturated. The flask was stoppered and stored in the refrigerator for 15 h. The reaction mixture was evaporated to give a white solid that was dried and chromatographed on a silica gel column, eluting with 2:1 hexanes/ethyl acetate, to give 9.87 g (95%) of (38) as a white solid, mp 93-94° C. MS, m/z: 264.10 (M+NH4)+.

To a 500 mL three-neck round-bottom flask fitted with mechanical stirrer, thermometer, and addition funnel was added 100 mL of dry methylene chloride and 8 mL (91.7 mmol) of oxalyl chloride under nitrogen. This was cooled to −78° C. in a dry ice/acetone bath. Then 13.6 mL (191.6 mmol) of DMSO in 25 mL of dry methylene chloride was added dropwise. After complete addition it was further stirred for 5 min. Then 9.87 g (40.0 mmol) of 38 in 10 mL of dry methylene chloride (with enough DMSO added to dissolve the solid) was added dropwise. The reaction mixture was stirred for an additional 30 min, and then 100 mL of triethylamine was added slowly at −78° C. After being stirred for 10 min, the solution was allowed to warm to room temperature, and then 200 mL of ice/water was added. Following separation of the layers, the aqueous layer was extracted with methylene chloride (2×100 mL). The organic layers were combined, dried over $MgSO_4$, filtered, and evaporated to give the crude product as a solid. This solid was slurried with cold methanol and filtered, washed with cold methanol, then dried in vacuo to give 6.37 g (66%) of 25 as a yellow solid, mp 113-114° C. MS, m/z: 242.0 (M+H)+.

To a solution of 2.43 g (16.5 mmol) of ethyl 3-nitropropionate (26) in 15 mL of absolute ethanol cooled in an ice bath was added 20 mL of 1 N sodium ethoxide in ethanol dropwise over 10 min, keeping the temperature at 0-5° C. A slurry of 2.43 g (10.0 mmol) of 25 in 5 mL of ethanol was added. The ice bath was removed, and the reaction mixture was stirred for 16 h. The mixture was transferred to a beaker with 300 mL of water and neutralized with acetic acid to pH 4. A solid was collected and washed first with water, then with 40 mL of cold ethanol. The solid was dried in vacuo to provide 2.48 g (70%) of ethyl 7-(2-chloroethoxy)-6-methoxy-3-nitro-2-naphthoate (27a) and ethyl 6-(2-chloroethoxy)-7-methoxy-3-nitro-2-naphthoate (27b) (1:1 mixture) as a yellow solid, mp 119-129° C. MS, m/z: 354 (M+H)+.

To a stirred solution of 27a (2.48 g, 7 mmol) in THF:$MeOH:H_2O$ (4:1:1) add $LiOH.H_2O$ (336 mg, 14 mmol) at temperature 27° C. and stirring was continued for a period of 6 h. After completion of reaction, solvent was removed under reduced pressure, neutralized with 1 N HCl and extracted into ethyl acetate. The organic layer was washed with water, dried over $Na_2SO_4$, concentrated to obtain compound of general formula 6-(2-chloroethoxy)-7-methoxy-3-nitro-2-naphthoic acid (28a) which was directly used without purification (1.94 g, 85%); MS, m/z: 326 (M+H)+.

To a stirred solution of 28a (1.94 g, 6 mmol) in benzene (35 mL) was treated with thionyl chloride (0.86 ml, 12 mmol), catalytic amount of DMF (5 drops) under nitrogen atmosphere at room temperature then and kept for overnight. After removal of solvent, the benzoyl chloride intermediate was added slowly to a solution of the methyl (2R)tetrahydro-1H-2-pyrrole carboxylate (874 mg, 10 mmol), TEA (4 ml, 28 mmol) in THF at 0° C. and kept for 1-2 h. After completion of the reaction as indicated by TLC, the solvent was removed; water was added, extracted into chloroform. The organic layer is washed with $NaHCO_3$ solution and brain. The organic layer was dried over $Na_2SO_4$ and concentrated under reduced pressure to get crude product, which was purified by column chromatography (50% ethyl acetate-hexane) to obtain methyl (25S)-1-[6-(2-chloroethoxy)-7-methoxy-3-nitro-2-naphthyl]carbonyl tetrahydro-1H-2-pyrrolecarboxylate (29a) as a pale yellow solid (2g, 85%); mp 221-225° C.; MS, m/z: 437 (M+H)+.

To a stirred solution of 29a (2 g, 10 mmol) in dry dichloromethane add diisobutyl aluminiumhydride (6.8 ml, 6.8 mmol) drop wise at −78° C., stirred for 45 min. After completion of the reaction 1 N HCl was added and separated organic layer. The organic layer was washed with water, brain, dried over $Na_2SO_4$ and concentrated to get aldehyde as a pale yellow solid (1.2 g 65%). The aldehyde was dissolved in dichloromethane add trimethylsilylchloride (0.93 ml, 6 mmol) and ethanethiol (0.54 ml, 6 mmol) at room temperature (27° C.) and stirred for 12 h. After completion of the reaction, sodium bicarbonate solution was added to neutralize excess trimethylsilylchloride. The organic layer was separated, washed with water, brain, dried over $Na_2SO_4$ and concentrated to get crude product. Which was purified by column chromatography to obtain [6-(2-chloroethoxy)-7-methoxy- 3-nitro-2-naphthyl](2S)-2-[di(ethylsulfanyl)methyl]tetrahydro-1H-1-pyrrolyl methanone (30a) as a pale yellow solid (1.28 g, 85%); MS, m/z: 514 (M+H)+

To compound (S)-(2-(bis(ethylthio)methyl)pyrrolidin-1-yl)(6-(2-chloroethoxy)-7-methoxy-3-nitronaphthalen-2-yl) methanone (30a) (300 mg, 0.58 mmol) in methanol (20 mL) was added $SnCl_2.2H_2O$ (0.65 g, 2.9 mmol) and refluxed at 65° C. for 5 h or until the TLC indicated that reaction was completed. The methanol was evaporated under vacuum; the aqueous layer was then carefully adjusted to pH 8 with 10% $NaHCO_3$ solution and then extracted with ethyl acetate and chloroform (2×30 mL and 2×30 mL). The combined organic phase was dried over $Na_2SO_4$ and evaporated under vacuum to afford the crude amino diethylthioacetal 31a (240 mg, 85%), which was used directly in the next step.

A solution of 31a (240 mg, 0.49 mmol), $HgCl_2$ (337 mg, 1.24 mmol) and $CaCO_3$ (124 mg, 1.24 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using MeOH—$CHCl_3$ (4%) to give compound 1a (105 mg, 59%). This material was repeatedly evaporated from $CHCl_3$ in vacuum to generate the imine form.

$^1$H NMR ($CDCl_3$, 300 MHz): δ 1.95-2.17 (m, 2H), 2.29-2.39 (m, 2H), 3.57-3.66 (m, 1H), 3.77-3.89 (m, 2H), 3.95 (t, 2H, J=6.043 Hz), 4.01 (s, 3H), 4.40 (t, 2H, J=6.04 Hz), 7.13 (s, 1H), 7.20 (s, 1H), 7.63 (s, 1H), 7.84 (d, 1H, J=4.53 Hz), 8.39 (s, 1H).

ESIMS: m/z 359 ($M^+$+1).

Example 2

9-Methoxy-8-(2-chloroethoxy-3a)-(13aS)-1,2,3,13a-tetrahdro-5H-pyrrolo[2,1-c][1,4]naphthodiazepine-5-one (2a)

To compound (S)-(2-(bis(ethylthio)methyl)pyrrolidin-1-yl)(7-(2-chloroethoxy)-6-methoxy-3-nitronaphthalen-2-yl) methanone (30b) (300 mg, 0.58 mmol) in methanol (20 mL) was added $SnCl_2.2H_2O$ (1.125 g, 5 mmol) and refluxed at 65° C. for 5 h or until the TLC indicated that reaction was completed. The methanol was evaporated under vacuum, the aqueous layer was then carefully adjusted to pH 8 with 10% $NaHCO_3$ solution and then extracted with ethyl acetate and chloroform (2×30 mL and 2×30 mL). The combined organic phase was dried over $Na_2SO_4$ and evaporated under vacuum to afford the crude amino diethylthioacetal 31b (240 mg, 85%), which was used directly in the next step.

A solution of 31b (240 mg, 0.49 mmol), $HgCl_2$ (337 mg, 1.24 mmol) and $CaCO_3$ (124 mg, 1.24 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using MeOH—$CHCl_3$ (4%) to give compound 2a (105 mg, 59%). This material was repeatedly evaporated from $CHCl_3$ in vacuum to generate the imine form.

$^1$H NMR ($CDCl_3$, 300 MHz): δ 1.96-2.19 (m, 2H), 2.29-2.40 (m, 2H), 3.58-3.66 (m, 1H), 3.77-3.89 (m, 2H), 3.94 (t, 2H, J=6.043 Hz), 4.01 (s, 3H), 4.40 (t, 2H, J=6.04 Hz), 7.13 (s, 1H), 7.21 (s, 1H), 7.63 (s, 1H), 7.85 (d, 1H, J=4.53 Hz), 8.41 (s, 1H).

ESIMS: m/z 359 ($M^+$+1).

Example 3

8-Methoxy-9-[2-(4-aceylpiperazino)ethoxy]-(13aS)-1,2,3,13a-tetrahydro-5H-pyrrolo[2,1-c][1,4]naphthodiazepin-5-one (5a)

To a mixture of compound (S)-(2-(bis(ethylthio)methyl)pyrrolidin-1-yl)(6-(2-chloroethoxy)-7-methoxy-3-nitronaphthalen-2-yl)methanone (30a) (300 mg, 0.58 mmol) and excess 1-acetyl piperazine (10 ml) add $K_2CO_3$ (552 mg, 4 mmol) and heated at 120° C. for 60 min. After completion of the reaction as indicated by TLC, potassium carbonate was removed by suction filtration and the crude product thus obtained was purified by column chromatography using ethyl acetate-hexane (1:1) as eluant to afford pure compound of general formula 32a (265 mg, 75%).

$^1$H NMR ($CDCl_3$, 300 MHz): δ 1.34-1.41 (m, 6H), 2.09 (s, 3H), 2.10-2.18 (m, 2H), 2.24-2.37 (m, 2H), 2.60-2.68 (brs, 4H), 2.70-2.87 (m, 4H), 3.04 (t, 2H, J=6.04 Hz), 3.32-3.39 (m, 2H), 3.53-3.63 (brs, 4H), 4.01 (s, 3H), 4.28 (t, 2H, J=6.04 Hz), 4.65-4.72 (m; 1H), 4.83 (d, 1H, J=3.96 Hz), 7.12 (s, 1H), 7.60 (s, 1H), 8.05 (s, 1H), 8.48 (s, 1H).

ESIMS: m/z 605 ($M^+$+1).

To compound of general formula 32a (604 mg, 1 mmol) in methanol (20 mL) was added $SnCl_2.2H_2O$ (1.125 g, 5 mmol) and refluxed at 65° C. for 5 h or until the TLC indicated that reaction was completed. The methanol was evaporated under vacuum, the aqueous layer was then carefully adjusted to pH 8 with 10% $NaHCO_3$ solution and then extracted with ethyl acetate and chloroform (2×30 mL and 2×30 mL). The combined organic phase was dried over $Na_2SO_4$ and evaporated under vacuum to afford the crude amino diethylthioacetal of general formula 33a (478 mg, 80%), which was used directly in the next step.

A solution of general formula 33a (572 mg, 1 mmol), $HgCl_2$ (613 mg, 2.26 mmol) and $CaCO_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using MeOH—$CHCl_3$ (4%) to give compound 5a (270 mg, 60%). This material was repeatedly evaporated from $CHCl_3$ in vacuum to generate the imine form.

$^1$H NMR ($CDCl_3$, 300 MHz): δ 1.99-2.08 (m, 2H), 2.09 (s, 3H), 2.27-2.36 (m, 2H), 2.59-2.67 (brs, 4H), 2.96 (t, 2H, J=6.04 Hz), 3.56-3.67 (brs, 4H), 3.79-3.94 (m, 3H), 3.98 (s, 3H), 4.29 (t, 2H, J=6.04 Hz), 7.12 (s, 1H), 7.19 (s, 1H), 7.67 (s, 1H), 7.84 (d, 1H, J=4.53 Hz), 8.42 (s, 1H).

ESIMS: m/z 451 ($M^+$+1).

Example 4

8-Methoxy-9-(2-[4-(1,3-benzodioxol-5-ylmethyl) piperazino]ethoxy)(3aS)-1,2,3,13a-tetrahydro-5H-pyrrolo[2,1-c][1,4]naphthodiazepin-5-one (7a)

To a mixture of compound (S)-(2-(bis(ethylthio)methyl) pyrrolidin-1-yl)(6-(2-chloroethoxy)-7-methoxy-3-nitronaphthalen-2-yl)methanone (30a) (300 mg, 0.58 mmol)

and excess 1-piperinoyl piperazine (10 ml) add K$_2$CO$_3$ (552 mg, 4 mmol) and heated at 120° C. for 60 min. After completion of the reaction as indicated by TLC, potassium carbonate was removed by suction filtration and the crude product thus obtained was purified by column chromatography using ethyl acetate-hexane (1:1) as eluant to afford pure compound of general formula 32a (305 mg, 75%).

$^1$H NMR (CDCl$_3$, 300 MHz): δ 1.34-1.41 (m, 6H), 2.09 (s, 3H), 2.10-2.17 (m, 2H), 2.23-2.38 (m, 2H), 2.60-2.68 (brs, 4H), 2.70-2.87 (m, 4H), 3.04 (t, 2H, J=6.04 Hz), 3.32-3.39 (m, 2H), 3.53-3.63 (brs, 4H), 4.01 (s, 3H), 4.28 (t, 2H, J=6.04 Hz), 4.65-4.72 (m, 1H), 4.83 (d, 1H, J=3.96 Hz), 5.31 (s, 2H), 5.97 (s, 1H), 6.76 (s, 1H), 6.88 (s, 1H), 7.10 (s, 1H), 7.18 (s, 1H), 7.62 (s, 1H), 8.41 (s, 1H).

ESIMS: m/z 697 (M$^+$+1).

To compound of general formula 32a (305 mg, 0.43 mmol) in methanol (20 mL) was added SnCl$_2$.2H$_2$O (493 mg, 2.19 mmol) and refluxed at 65° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal of general formula 33a (236 mg, 81%), which was used directly in the next step.

A solution of general formula 33a (236 mg, 0.35 mmol), HgCl$_2$ (613 mg, 0.88 mmol) and CaCO$_3$ (88 mg, 0.88 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 7a (105 mg, 55%). This material was repeatedly evaporated from CHCl$_3$ in vacuum to generate the imine form.

$^1$H NMR (CDCl$_3$, 300 MHz): δ 1.86-2.10 (m, 2H), 2.27-2.31 (m, 2H), 2.73 (brs, 4H), 2.86 (brs, 4H), 3.60 (t, 2H, J=6.04 Hz), 3.72-3.91 (m, 3H), 3.95 (s, 3H), 4.29 (t, 2H, J=6.04 Hz), 5.30 (s, 2H), 5.94 (s, 1H), 6.75 (s, 1H), 6.85 (s, 1H), 7.10 (s, 1H), 7.17 (s, 1H), 7.60 (s, 1H), 7.83 (d, 1H, J=3.77 Hz), 8.40 (s, 1H).

ESIMS: m/z 543 (M$^+$+1).

Example 5

8-Methoxy-9-[2-(4-benzylpiperazino)ethoxy]-(13aS)-1,2,3,13a-tetrahydro-5H-pyrrolo[2,1-c][1,4]naphthodiazepin-5-one (6a)

To a mixture of compound (S)-(2-(bis(ethylthio)methyl)pyrrolidin-1-yl)(6-(2-chloroethoxy)-7-methoxy-3-nitronaphthalen-2-yl)methanone (30a) (300 mg, 0.58 mmol) and excess 1-benzyl piperazine (10 ml) add K$_2$CO$_3$ (552 mg, 4 mmol) and heated at 120° C. for 60 min. After completion of the reaction as indicated by TLC, potassium carbonate was removed by suction filtration and the crude product thus obtained was purified by column chromatography using ethyl acetate-hexane (1:1) as eluant to afford pure compound of general formula 32a (297 mg, 78%).

$^1$H NMR (CDCl$_3$, 300 MHz): δ 1.34-1.41 (m, 6H), 2.09 (s, 3H), 2.10-2.17 (m, 2H), 2.23-2.38 (m, 2H), 2.60-2.68 (brs, 4H), 2.70-2.87 (m, 4H), 3.04 (t, 2H, J=6.04 Hz), 3.32-3.39 (m, 2H), 3.51 (s, 2H), 3.53-3.63 (brs, 4H), 4.01 (s, 3H), 4.28 (t, 2H, J=5.95 Hz), 4.65-4.72 (m, 1H), 4.83 (d, 1H, J=3.96 Hz), 5.31 (s, 2H), 5.96 (s, 1H), 6.74 (s, 1H), 6.89 (s, 1H), 7.11 (s, 1H), 7.18 (s, 1H), 7.61 (s, 1H), 8.43 (s, 1H).

ESIMS: m/z 697 (M$^+$+1).

To compound of general formula 32a (297 mg, 0.45 mmol) in methanol (20 mL) was added SnCl$_2$.2H$_2$O (512 mg, 2.2 mmol) and refluxed at 65° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal of general formula 33a (539 mg, 81%), which was used directly in the next step.

A solution of general formula 33a (666 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 6a (297 mg, 55%). This material was repeatedly evaporated from CHCl$_3$ in vacuum to generate the imine form.

$^1$H NMR (CDCl$_3$, 300 MHz): δ 1.86-2.10 (m, 2H), 2.27-2.31 (m, 2H), 2.73 (brs, 4H), 2.86 (brs, 4H), 3.60 (t, 2H, J=6.04 Hz), 3.72-3.91 (m, 3H), 3.95 (s, 3H), 4.29 (t, 2H, J=6.04 Hz), 5.30 (s, 2H), 5.94 (s, 1H), 6.75 (s, 1H), 6.85 (s, 1H), 7.10 (s, 1H), 7.17 (s, 1H), 7.60 (s, 1H), 7.83 (d, 1H, J=3.77 Hz), 8.40 (s, 1H).

ESIMS: m/z 543 (M$^+$+1).

Example 6

8-Methoxy-9-[2-(4-phenylpiperazino)ethoxy]-(13aS)-1,2,3,13a-tetrahydro-5H-pyrrolo[2,1-c][1,4]naphthodiazepin-5-one (8a)

To a mixture of compound (S)-(2-(bis(ethylthio)methyl)pyrrolidin-1-yl)(6-(2-chloroethoxy)-7-methoxy-3-nitronaphthalen-2-yl)methanone (30a) (300 mg, 0.58 mmol) and excess 1-phenyl piperazine (10 ml) add K$_2$CO$_3$ (552 mg, 4 mmol) and heated at 120° C. for 60 min. After completion of the reaction as indicated by TLC, potassium carbonate was removed by suction filtration and the crude product thus obtained was purified by column chromatography using ethyl acetate-hexane (1:1) as eluant to afford pure compound of general formula 32a (452 mg, 71%).

$^1$H NMR (CDCl$_3$, 300 MHz): δ 1.34-1.41 (m, 6H), 1.76-2.10 (m, 2H), 2.05-2.37 (m, 2H), 2.70-2.91 (m, 6H), 3.01 (t, 2H, J=6.04 Hz), 3.12-3.19 (m, 2H), 3.25 (t, 4H, J=5.28 Hz), 3.31-3.41 (m, 2H), 3.51-3.54 (m, 1H), 3.68-3.72 (m, 1H), 4.03 (s, 3H), 4.33 (t, 2H, J=6.04 Hz), 4.70-4.78 (m, 1H), 4.92 (d, 1H, J=3.77 Hz), 6.86 (t, 1H, J=7.55 Hz), 6.95 (d, 2H, J=9.06 Hz), 7.15 (s, 1H), 7.23-7.31 (m, 3H), 7.66 (s, 1H), 8.55 (s, 1H).

ESIMS: m/z 639 (M$^+$+1).

To compound of general formula 32a (638 mg, 1 mmol) in methanol (20 mL) was added SnCl$_2$.2H$_2$O (1.125 g, 5 mmol) and refluxed at 65° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal of general formula 33a (504 mg, 83%), which was used directly in the next step.

A solution of general formula 33a (608 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 8a (275 mg, 57%). This material was repeatedly evaporated from CHCl$_3$ in vacuum to generate the imine form.

$^1$H NMR (CDCl$_3$, 300 MHz): δ 2.01-2.13 (m, 2H), 2.27-2.36 (m, 2H), 2.84-2.87 (brs, 4H), 3.05 (t, 2H, J=6.04 Hz), 3.26-3.29 (brs, 4H), 3.79-3.96 (m, 3H), 3.99 (s, 3H), 4.35 (t, 2H, J=6.04 Hz), 6.87 (t, 1H, J=6.79 Hz), 6.95 (d, 2H, J=8.30 Hz), 7.14 (s, 1H), 7.20 (s, 1H), 7.25 (d, 1H, J=6.79 Hz), 7.29 (d, 1H, J=7.55 Hz), 7.62 (s, 1H), 7.84 (d, 1H, J=4.83 Hz), 8.42 (s, 1H).

ESIMS: m/z 485 (M$^+$+1).

Example 7

8-Methoxy-9-(2-[4-(2-pyridyl)piperazino]ethoxy)-(13aS)-1,2,3,13a-tetrahydro-5H-pyrrolo[2,1-c][1,4]naphthodiazepin-5-one (12a)

To a mixture of compound (S)-(2-(bis(ethylthio)methyl)pyrrolidin-1-yl)(6-(2-chloroethoxy)-7-methoxy-3-nitronaphthalen-2-yl)methanone (30a) (300 mg, 0.58 mmol) and excess 1-pyridyl piperazine (10 ml) add K$_2$CO$_3$ (552 mg, 4 mmol) and heated at 120° C. for 60 min. After completion of the reaction as indicated by TLC, potassium carbonate was removed by suction filtration and the crude product thus obtained was purified by column chromatography using ethyl acetate-hexane (1:1) as eluant to afford pure compound of general formula 32a (504 mg, 79%).

$^1$H NMR (CDCl$_3$, 300 MHz): δ 1.34-1.40 (m, 6H), 1.97-2.08 (m, 2H), 2.26-2.38 (m, 2H), 2.70-2.91 (m, 8H), 3.03 (t, 2H, J=5.66 Hz), 3.30-3.40 (m, 2H), 3.59-3.62 (brs, 4H), 4.03 (s, 3H), 4.36 (t, 2H, J=5.66 Hz), 4.72-4.78 (m, 1H), 4.91 (d, 1H, J=3.77 Hz), 6.63-6.68 (m, 2H), 7.16 (s, 1H), 7.29 (s, 1H), 7.44-7.53 (m, 1H), 7.66 (s, 1H), 8.18 (d, 1H, J=3.39 Hz), 8.53 (s, 1H).

ESIMS: m/z 640 (M$^+$+1).

To compound of general formula 32a (639 mg, 1 mmol) in methanol (20 mL) was added SnCl$_2$.2H$_2$O (1.125 g, 5 mmol) and refluxed at 65° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal of general formula 33a (573 mg, 84%), which was used directly in the next step.

A solution of general formula 33a (609 mg, 1 mmol), HgCl$_2$ (511 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 12a (257 mg, 53%). This material was repeatedly evaporated from CHCl$_3$ in vacuum to generate the imine form.

$^1$H NMR (CDCl$_3$, 300 MHz): δ 2.01-2.12 (m, 2H), 2.27-2.36 (m, 2H), 2.70 (brs, 4H), 3.00 (t, 2H, J=6.24 Hz), 3.88 (brs, 4H), 3.91-3.96 (m, 3H), 3.98 (s, 3H), 4.33 (t, 2H, J=6.04 Hz), 6.48 (s, 1H), 7.14 (s, 1H), 7.19 (s, 1H), 7.61 (s, 1H), 7.83 (d, 1H, J=5.20 Hz), 8.30 (d, 3H, J=5.50 Hz), 8.54 (s. 1H).

ESIMS: m/z 486 (M$^+$+1).

Example 8

8-Methoxy-9-(2-[4-(2-pyrimidinyl)piperazino]ethoxy)-(13aS)-1,2,3,13a-tetrahydro-5H-pyrrolo[2,1-c][1,4]naphthodiazepin-5-one (13a)

To a mixture of compound (S)-(2-(bis(ethylthio)methyl)pyrrolidin-1-yl)(6-(2-chloroethoxy)-7-methoxy-3-nitronaphthalen-2-yl)methanone (30a) (300 mg, 0.58 mmol) and excess 1-pyrimidyl piperazine (10 ml) add K$_2$CO$_3$ (552 mg, 4 mmol) and heated at 120° C. for 60 min. After completion of the reaction as indicated by TLC, potassium carbonate was removed by suction filtration and the crude product thus obtained was purified by column chromatography using ethyl acetate-hexane (1:1) as eluant to afford pure compound of general formula 32a (467 mg, 73%).

$^1$H NMR (CDCl$_3$, 300 MHz): δ 1.34-1.42 (m, 6H), 1.97-2.08 (m, 2H), 2.26-2.38 (m, 2H), 2.70-2.91 (m, 8H), 3.03 (t, 2H, J=6.04 Hz), 3.30-3.40 (m, 2H), 3.57-3.61 (brs, 4H), 4.03 (s, 3H), 4.36 (t, 2H, J=6.04 Hz), 4.72-4.78 (m, 1H), 4.91 (d, 1H, J=3.77 Hz), 6.50 (t, 1H, J=4.35 Hz), 7.16 (s, 1H), 7.20 (s, 1H), 7.61 (s, 1H), 8.33 (d, 2H, J=6.25 Hz), 8.44 (s, 1H).

ESIMS: m/z 642 (M$^+$+1).

To compound of general formula 32a (641 mg, 1 mmol) in methanol (20 mL) was added SnCl$_2$.2H$_2$O (1.125 g, 5 mmol) and refluxed at 65° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal of general formula 33a (495 mg, 81%), which was used directly in the next step.

A solution of general formula 33a (611 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 13a (256 mg, 59%). This material was repeatedly evaporated from CHCl$_3$ in vacuum to generate the imine form.

$^1$H NMR (CDCl$_3$, 300 MHz): δ 2.02-2.10 (m, 2H), 2.29-2.34 (m, 2H), 2.66-2.71 (brs, 4H), 3.00 (t, 2H, J=6.24 Hz), 3.88-3.89 (brs, 4H), 3.91-3.97 (m, 3H), 3.98 (s, 3H), 4.33 (t, 2H, J=6.04 Hz), 6.48 (t, 1H, J=4.16 Hz), 7.14 (s, 1H), 7.19 (s, 1H), 7.61 (s, 1H), 7.84 (d, 1H, J=4.16 Hz), 8.30 (d, 2H, J=5.20 Hz), 8.42 (s, 1H).

ESIMS: m/z 487 (M$^+$+1).

Example 9

9-Methoxy-8-[2-(4-ethylpiperazino)ethoxy](13aS)-1,2,3,13a-tetrahydro-5H-pyrrolo[2,1-c][1,4]naphthodiazepin-5-one (15a)

To a mixture of compound (S)-(2-(bis(ethylthio)methyl)pyrrolidin-1-yl)(7-(2-chloroethoxy)-6-methoxy-3-nitronaphthalen-2-yl)methanone (30b) (300 mg, 0.58 mmol) and excess 1-ethyl piperazine (10 ml) add $K_2CO_3$ (552 mg, 4 mmol) and heated at 120° C. for 60 min. After completion of the reaction as indicated by TLC, potassium carbonate was removed by suction filtration and the crude product thus obtained was purified by column chromatography using ethyl acetate-hexane (1:1) as eluant to afford pure compound of general formula 32b (460 mg, 78%).

$^1$H NMR (CDCl$_3$, 300 MHz): δ 1.05 (t, 3H, J=7.55 Hz), 1.34-1.41 (m, 6H), 2.25-2.34 (m, 2H), 2.37-2.46 (m, 2H), 2.52-2.56 (brs, 4H), 2.62-2.71 (brs, 4H), 2.93 (t, 2H, J=6.04 Hz), 3.29-3.39 (m, 2H), 4.01 (s, 3H), 4.25 (t, 2H, J=6.04 Hz), 4.66-4.74 (m, 1H), 4.85 (d, 1H, J=3.77 Hz), 7.12 (s, 1H), 7.24 (s, 1H), 7.61 (s, 1H), 8.50 (s, 1H); ESIMS: m/z 591 (M$^+$+1).

To compound of general formula 32b (590 mg, 1 mmol) in methanol (20 mL) was added SnCl$_2$.2H$_2$O (1.125 g, 5 mmol) and refluxed at 65° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal of general formula 33b (431 mg, 77%), which was used directly in the next step.

A solution of general formula 33b (560 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 15a (244 mg, 56%). This material was repeatedly evaporated from CHCl$_3$ in vacuum to generate the imine form.

$^1$H NMR (CDCl$_3$, 300 MHz): δ 1.23 (t, 3H, J=5.12 Hz), 1.99-2.07 (m, 2H), 2.24-2.30 (m, 2H), 2.72-2.75 (m, 2H), 2.84 (brs, 8H), 2.97 (t, 2H, J=5.12 Hz), 3.79-3.91 (m, 3H), 3.95 (s, 3H), 4.25 (t, 2H, J=5.25 Hz), 7.08 (s, 1H), 7.07 (s, 1H), 7.59 (s, 1H), 7.82 (d, 1H, J=3.66 Hz), 8.39 (s, 1H).

ESIMS: m/z 437 (M$^+$+1).

Example 10

9-Methoxy-8-[2-(4-phenylpiperazino)ethoxy]-(13aS)-1,2,3,13a-tetrahydro-5H-pyrrolo[2,1-c][1,4]naphthodiazepin-5-one (19a)

To a mixture of compound (S)-(2-(bis(ethylthio)methyl)pyrrolidin-1-yl)(7-(2-chloroethoxy)-6-methoxy-3-nitronaphthalen-2-yl)methanone (30b) (300 mg, 0.58 mmol) and excess 1-phenyl piperazine (10 ml) add $K_2CO_3$ (552 mg, 4 mmol) and heated at 120° C. for 60 min. After completion of the reaction as indicated by TLC, potassium carbonate was removed by suction filtration and the crude product thus obtained was purified by column chromatography using ethyl acetate-hexane (1:1) as eluant to afford pure compound of general formula 32b (446 mg, 70%).

$^1$H NMR (CDCl$_3$, 300 MHz): δ 1.35-1.40 (m, 6H), 1.78-1.93 (m, 2H), 2.05-2.16 (m, 2H), 2.67-2.89 (m, 8H), 2.98 (t, 2H, J=6.47 Hz), 3.20 (t, 4H, J=4.85 Hz), 3.29-3.38 (m, 2H), 4.00 (s, 3H), 4.30 (t, 2H, J=5.66 Hz), 4.66-4.72 (m, 1H), 4.84 (d, 1H, J=3.23 Hz), 6.80 (t, 1H, J=7.28 Hz), 6.85 (d, 2H, J=8.09 Hz), 7.15 (s, 1H), 7.18-7.22 (m, 3H), 7.59 (s, 1H), 8.50 (s, 1H).

ESIMS: m/z 639 (M$^+$+1).

To compound of general formula 32b (638 mg, 1 mmol) in methanol (20 mL) was added SnCl$_2$.2H$_2$O (1.125 g, 5 mmol) and refluxed at 65° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal of general formula 33b (535 mg, 88%), which was used directly in the next step.

A solution of general formula 33b (608 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 19a (266 mg, 55%). This material was repeatedly evaporated from CHCl$_3$ in vacuum to generate the imine form.

$^1$H NMR (CDCl$_3$, 300 MHz): δ 1.98-2.12 (m, 2H), 2.25-2.34 (m, 2H), 2.77-2.84 (brs, 4H), 3.03 (t, 2H, J=5.28 Hz), 3.23-3.29 (brs, 4H), 3.78-3.96 (m, 3H), 4.00 (s, 3H), 4.34 (t, 2H, J=6.04 Hz), 6.86 (t, 1H, J=6.79 Hz), 6.95 (d, 2H, J=7.55 Hz), 7.11 (s, 1H), 7.23-7.29 (m, 4H), 7.63 (s, 1H), 7.84 (d, 1H, J=4.53 Hz), 8.41 (s, 1H).

ESIMS: m/z 485 (M$^+$+1).

Example 11

9-Methoxy-8-(2-[4-(4-fluorophenyl)piperazino]ethoxy)-(3aS)-1,2,3,13a-tetrahydro-5H-pyrrolo[2,1-c][1,4]naphthodiazepin-5-one (20a)

To a mixture of compound (S)-(2-(bis(ethylthio)methyl)pyrrolidin-1-yl)(7-(2-chloroethoxy)-6-methoxy-3-nitronaphthalen-2-yl)methanone (30b) (300 mg, 0.58 mmol) and excess 1-(4-fluorophenyl)piperazine (10 ml) add $K_2CO_3$ (552 mg, 4 mmol) and heated at 120° C. for 60 min. After completion of the reaction as indicated by TLC, potassium carbonate was removed by suction filtration and the crude product thus obtained was purified by column chromatography using ethyl acetate-hexane (1:1) as eluant to afford pure compound of general formula 32b (479 mg, 73%).

$^1$H NMR (CDCl$_3$, 300 MHz): δ 1.35-1.40 (m, 6H), 2.04-2.14 (m, 2H), 2.27-2.36 (m, 2H), 2.71-2.91 (m, 8H), 3.02 (t, 2H, J=5.66 Hz), 3.17 (t, 4H, J=4.85 Hz), 3.32-3.41 (m, 2H), 4.02 (s, 3H), 4.35 (t, 2H, J=5.66 Hz), 4.70-4.77 (m, 1H), 4.90 (d, 1H, J=4.04 Hz), 6.88 (d, 1H, J=4.85 Hz), 6.89 (d, 1H, J=4.85 Hz), 6.96 (t, 2H, J=8.09 Hz), 7.18 (s, 1H), 7.25 (s, 1H), 7.65 (s, 1H), 8.56 (s, 1H).

ESIMS: m/z 657 (M+1).

To compound of general formula 32b (656 mg, 1 mmol) in methanol (20 mL) was added SnCl$_2$.2H$_2$O (1.125 g, 5 mmol)

and refluxed at 65° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal of general formula 33b (532 mg, 85%), which was used directly in the next step.

A solution of general formula 33b (626 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 20a (291 mg, 58%). This material was repeatedly evaporated from CHCl$_3$ in vacuum to generate the imine form.

$^1$H NMR (CDCl$_3$, 300 MHz): δ 1.35-1.40 (m, 6H), 1.78-1.94 (m, 2H), 2.05-2.14 (m, 2H), 2.67-2.89 (m, 8H), 2.98 (t, 2H, J=6.47 Hz), 3.20 (t, 4H, J=4.85 Hz), 3.29-3.38 (m, 2H), 4.00 (s, 3H), 4.30 (t, 2H, J=5.66 Hz), 4.66-4.72 (m, 1H), 4.84 (d, 1H, J=3.23 Hz), 6.88 (d, 1H, J=4.85 Hz), 6.89 (d, 1H, J=4.85 Hz), 6.94 (t, 2H, J=8.09 Hz), 7.17 (s, 1H), 7.25 (s, 1H), 7.60 (s, 1H), 7.84 (d, 1H, J=4.52 Hz), 8.55 (s, 1H).

ESIMS: m/z 503 (M$^+$+1).

Example 12

9-Methoxy-8-(2-[4-(2-pyridyl)piperazino]ethoxy)-(13aS)-1,2,3,13a-tetrahydro-5H-pyrrolo[2,1-c][1,4]naphthodiazepin-5-one (23a)

To a mixture of compound (S)-(2-(bis(ethylthio)methyl)pyrrolidin-1-yl)(7-(2-chloroethoxy)-6-methoxy-3-nitronaphthalen-2-yl)methanone (30b) (300 mg, 0.58 mmol) and excess 1-pyridylpiperazine (10 ml) add K$_2$CO$_3$ (552 mg, 4 mmol) and heated at 120° C. for 60 min. After completion of the reaction as indicated by TLC, potassium carbonate was removed by suction filtration and the crude product thus obtained was purified by column chromatography using ethyl acetate-hexane (1:1) as eluant to afford pure compound of general formula 32b (492 mg, 77%).

$^1$H NMR (CDCl$_3$, 300 MHz): δ 1.34-1.41 (m, 6H), 1.99-2.08 (m, 2H), 2.26-2.42 (m, 2H), 2.70-2.91 (m, 8H), 3.03 (t, 2H, J=5.66 Hz), 3.30-3.40 (m, 2H), 3.59-3.62 (brs, 4H), 4.03 (s, 3H), 4.36 (t, 2H, J=5.66 Hz), 4.72-4.78 (m, 1H), 4.91 (d, 1H, J=3.77 Hz), 6.63-6.68 (m, 2H), 7.16 (s, 1H), 7.29 (s, 1H), 7.44-7.53 (m, 1H), 7.66 (s, 1H), 8.20 (d, 1H, J=3.39 Hz), 8.55 (s, 1H).

ESIMS: m/z 640 (M$^+$+1).

To compound of general formula 32b (639 mg, 1 mmol) in methanol (20 mL) was added SnCl$_2$.2H$_2$O (1.125 g, 5 mmol) and refluxed at 65° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal of general formula 33b (493 mg, 81%), which was used directly in the next step.

A solution of general formula 33b (609 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 23a (291 mg, 60%). This material was repeatedly evaporated from CHCl$_3$ in vacuum to generate the imine form.

$^1$H NMR (CDCl$_3$, 300 MHz): δ 1.79-2.12 (m, 2H), 2.25-2.39 (m, 2H), 2.77 (brs, 4H), 3.01 (t, 2H, J=6.04 Hz), 3.60 (brs, 4H), 3.76-3.94 (m, 3H), 3.99 (s, 3H), 4.34 (t, 2H, J=6.04 Hz), 6.64 (d, 2H, J=9.06 Hz), 7.14 (s, 1H), 7.19 (s, 1H), 7.45-7.51 (m, 1H), 7.62 (s, 1H), 7.85 (d, 1H, J=4.53 Hz), 8.18 (d, 1H, J=3.77 Hz), 8.42 (s, 1H).

ESIMS: m/z 486 (M$^+$+1).

Example 13

9-Methoxy-8-(2-[4-(2-pyrimidinyl)piperazino]ethoxy)-(13aS)-1,2,3,13a-tetrahydro-5H-pyrrolo[2,1-c][1,4]naphthodiazepin-5-one (24a)

To a mixture of compound (S)-(2-(bis(ethylthio)methyl)pyrrolidin-1-yl)(7-(2-chloroethoxy)-6-methoxy-3-nitronaphthalen-2-yl)methanone (30b) (300 mg, 0.58 mmol) and excess 1-pyridylpiperazine (10 ml) add K$_2$CO$_3$ (552 mg, 4 mmol) and heated at 120° C. for 60 min. After completion of the reaction as indicated by TLC, potassium carbonate was removed by suction filtration and the crude product thus obtained was purified by column chromatography using ethyl acetate-hexane (1:1) as eluant to afford pure compound of general formula 32b (486 mg, 76%).

$^1$H NMR (CDCl$_3$, 300 MHz): δ 1.34-1.41 (m, 6H), 1.99-2.08 (m, 2H), 2.26-2.42 (m, 2H), 2.70-2.91 (m, 8H), 3.03 (t, 2H, J=5.66 Hz), 3.30-3.40 (m, 2H), 3.59-3.62 (brs, 4H), 4.03 (s, 3H), 4.36 (t, 2H, J=5.66 Hz), 4.72-4.78 (m, 1H), 4.91 (d, 1H, J=3.77 Hz), 6.48 (t, 1H, J=4.25 Hz), 7.14 (s, 1H), 7.19 (s, 1H), 7.62 (s, 1H), 8.30 (d, 2H, J=5.20 Hz), 8.44 (s, 1H).

ESIMS: m/z 641 (M$^+$+1).

To compound of general formula 32b (640 mg, 1 mmol) in methanol (20 mL) was added SnCl$_2$.2H$_2$O (1.125 g, 5 mmol) and refluxed at 65° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal of general formula 33b (529 mg, 84%), which was used directly in the next step.

A solution of general formula 33b (630 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 24a (291 mg, 60%). This material was repeatedly evaporated from CHCl$_3$ in vacuum to generate the imine form.

$^1$H NMR (CDCl$_3$, 300 MHz): δ 2.02-2.10 (m, 2H), 2.29-2.34 (m, 2H), 2.66-2.71 (brs, 4H), 3.00 (t, 2H, J=6.24 Hz), 3.88-3.89 (brs, 4H), 3.91-3.97 (m, 3H), 3.98 (s, 3H), 4.33 (t, 2H, J=6.04 Hz), 6.48 (t, 1H, J=4.16 Hz), 7.14 (s, 1H), 7.19 (s, 1H), 7.61 (s, 1H), 7.84 (d, 1H, J=4.16 Hz), 8.30 (d, 2H, J=5.20 Hz), 8.42 (s, 1H).

ESIMS: m/z 487 (M+1).

BIOLOGICAL ACTIVITY

DNA Binding Affinity of Substituted Piperazine Linked Pyrrolo Naphtho Diazepine Hybrids:

Compounds have been subjected to thermal denaturation studies with duplex-form calf thymus DNA (CT-DNA) using an modification of a reported procedure (Newman, M. S. *Carcinog-compr. Surv.* 1976, 1, 203; (b) Hecht, S. S.; Loy, M.; Hoffman, *Carcinog-compr. Surv.* 1976, 1, 325). Working solutions in aqueous buffer (10 mM $NaH_2PO_4/Na_2HPO_4$, 1 mM $Na_2EDTA$, pH 7.00+0.01) containing CT-DNA (100 μm in phosphate) and the PND (pyrrolo naphtha diazepine) (20 μm) have been prepared by addition of concentrated PND (pyrrolo naphtha diazepine) solutions in DMSO to obtain a fixed [PND]/[DNA] molar ratio of 1:5. The DNA-PND (pyrrolo naphtha diazepine) solutions have been incubated at 37° C. for 0 and 18 h prior to analysis. Samples have been monitored at 260 nm using a Beckman DU-800 spectrophotometer fitted with high performance temperature controller, and heated at 1° C. min in the 40-110° C. range. DNA helix→coil transition temperatures ($T_m$) have been obtained from the maxima in the $d(A_{260})/dT$ derivative plots. Drug-induced alterations in DNA melting behavior are given by: $\Delta T_m = T_m$ (DNA+PND)−$T_m$(DNA alone), where the $T_m$ value for the PND-free CT-DNA is 69.1±0.01. The fixed [PND]/[DNA] ratio used has not resulted in binding saturation of the host DNA duplex for any compound examined.

The DNA binding activity for these novel substituted piperazine linked pyrrolo naphtho diazepine hybrids has been examined by thermal denaturation studies using calf thymus (CT) DNA. Melting studies show that these compounds stabilize the thermal helix→coil or melting stabilization ($\Delta T_m$) ($\Delta Tm = Tm(DNA+PND)−Tm(DNA$ alone)) for the CT-DNA duplex at pH 7.0, incubated at 37° C., where PND/DNA molar ratio is 1:5. The data for some of the compounds are included in Table 1 for comparison.

TABLE 1

Thermal denaturation data for piperazine linked pyrrolo naphtho diazepine hybrids with calf thymus (CT) DNA at a molar ratio of 1:5 in aqueous sodium phosphate buffer at pH 7 and having the following thermal denaturation data:

| PND hybrides | [PBD]:[DNA] molar ratio[b] | ($\Delta T_m$ ° C.)[a] after incubation at 37° C. for 0 hr | 18 hrs |
|---|---|---|---|
| 1a | 1:5 | 6.2 | 7.6 |
| 2a | 1:5 | 7.1 | 9.5 |
| 5a | 1:5 | 5.5 | 7.1 |
| 7a | 1:5 | 4.9 | 6.5 |
| 8a | 1:5 | 5.1 | 6.9 |
| 12a | 1:5 | 5.8 | 7.1 |
| 13a | 1:5 | 5.0 | 6.5 |
| 15a | 1:5 | 6.1 | 7.2 |
| 19a | 1:5 | 6.5 | 7.3 |
| 20a | 1:5 | 5.9 | 7.0 |
| 23a | 1:5 | 5.0 | 6.8 |
| 24a | 1:5 | 4.9 | 6.5 |
| DC-81 | 1:5 | 0.3 | 0.7 |

[a]For CT-DNA alone at pH 7.00 ± 0.01, $T_m$ = 69.1° C. ± 0.01 (mean value from 10 separate determinations), all $\Delta T_m$ values are ±0.1-0.2° C.
[b]For a 1:5 molar ratio of [PND]/[DNA], where CT-DNA concentration = 100 μM and ligand concentration = 20 μM in aqueous sodium phosphate buffer [10 mM sodium phosphate +1 mM EDTA, pH 7.00 ± 0.01].

ANTICANCER ACTIVITY

In vitro biological activity studies were carried out at the pharmacology division, IICT, Hyderabad. The compounds were evaluated for in vitro anticancer activity against eight tumour cell lines derived from eight cancer types (breast, lung, liver, skeletal, kidney, prostrate, small intestine) as shown in Table 2. For each compound, dose response curves for each cell line were measured at a minimum of five concentrations at 10 fold dilutions. A protocol of 48 h continuous drug exposure was used and a MTT assay was used to estimate cell viability or growth. The concentration causing 50% inhibition ($IC_{50}$) compared with the control was calculated. Some of the compounds have been evaluated for their in vitro cytotoxicity in eight cell lines from seven human cancer types. The results are expressed as $IC_{50}$ determined relative to that of untreated control cells (Table-2).

TABLE 2

$IC_{50}$ (concentration in μM) values for the representative compounds against human tumour cell lines.

| comp | MCF7[a] | A549[b] | HEPG2[c] | NCIH460[d] | PC-3[e] | COS-1[f] | IEC-6[g] | L-6[h] |
|---|---|---|---|---|---|---|---|---|
| 1a | 0.05 | 0.02 | 0.52 | 0.30 | 0.39 | 3.06 | 0.02 | 1.08 |
| 2a | 0.002 | 0.11 | 0.02 | 0.02 | 0.02 | 0.91 | 0.01 | 0.002 |
| 5a | 2.88 | 0.66 | 7.32 | 1.68 | 13.5 | nt | nt | 2.66 |
| 7a | 0.20 | 2.21 | 0.11 | 0.08 | 0.64 | 2.58 | 0.05 | 0.77 |
| 8a | 1.50 | 7.42 | 0.47 | 0.43 | 1.60 | 6.39 | 0.14 | 1.01 |
| 12a | 0.01 | 0.32 | 0.22 | 0.24 | 0.10 | 4.32 | 0.16 | 0.86 |
| 13a | 0.04 | 0.86 | 0.04 | 0.26 | 0.08 | 1.87 | 0.02 | 0.61 |
| 15a | 0.04 | 0.54 | 0.20 | 1.25 | 0.41 | 3.66 | 0.13 | 1.87 |
| 19a | 0.18 | 9.90 | 0.04 | 0.006 | 0.30 | 0.80 | 0.01 | 0.26 |
| 20a | 3.99 | 10.55 | 4.03 | 0.99 | 4.37 | nt | 5.84 | 6.36 |
| 23a | 0.02 | 1.99 | 0.04 | 0.11 | 0.10 | 4.32 | 0.01 | 0.74 |
| 24a | 1.97 | 11.92 | 1.04 | 0.002 | 0.01 | nt | 0.20 | 2.21 |
| DC-81 | 12.58 | 17.46 | 5.27 | 8.93 | 14.21 | 32.89 | 15.38 | 27.61 |

DC-81 = pyrrolo[2,1-c][1,4]benzodiazepine
[a]= breast cancer cell line,
[b]= lung cancer cell line,
[c]= liver cancer cell line,
[d]= large cell lung cancer cell line,
[e]= prostrate cancer cell line,
[f]= kidney cancer cell line,
[g]= small intestine cell line,
[h]= skeletal cancer cell line,
nt = not tested.

ADVANTAGES OF THE INVENTION

DNA alkylating agents have been widely used in cancer chemotherapy. These agents have several drawbacks including a lack of drug-specific affinity towards tumour cells. To overcome this problem, in the present invention the alkylating agents coupled with DNA minor groove binders. More over the thermal denaturation study reveals that conjugates are more effective than their individual motifs.

We claim:
1. A compound of formula A:

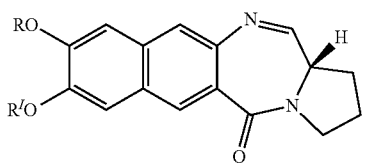

Formula A

Where R=R$^I$=CH$_3$,

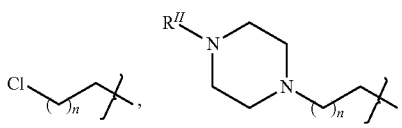

n=1-9 and R$^{II}$=methyl, ethyl, acetyl, benzyl, piperinoyl, 4-fluorophenyl, 4-chlorophenyl, 4-methoxyphenyl, pyridyl, pyrimidyl.

2. The compound according to claim 1, selected from the group consisting of:
- 8-Methoxy-9-(2-chloroethoxy)-(13aS)-1,2,3,13a-tetrahydro-5H-pyrrolo[2,1-c][1,4]naphthodiazepine-5-one (1a)
- 8-Methoxy-9-(3-chloropropoxy)-(13aS)-1,2,3,13a-tetrahydro-5H-pyrrolo[2,1-c][1,4]naphthodiazepine-5-one (1b)
- 8-Methoxy-9-(4-chlorobutoxy)-(13aS)-1,2,3,13a-tetrahydro-5H-pyrrolo[2,1-c][1,4]naphthodiazepine-5-one (1c)
- 8-Methoxy-9-[(5-chloropentyl)oxy]-(13aS)-1,2,3,13a-tetrahydro-5H-pyrrolo[2,1-c][1,4]naphthodiazepine-5-one (1d)
- 8-Methoxy-9-[(6-chlorohexyl)oxy]-(13aS)-1,2,3,13a-tetrahydro-5H-pyrrolo[2,1-c][1,4]naphthodiazepine-5-one (1e)
- 8-Methoxy-9-[(7-chloroheptyl)oxy]-(13aS)-1,2,3,13a-tetrahydro-5H-pyrrolo[2,1-c][1,4]naphthodiazepine-5-one (1f)
- 8-Methoxy-9-[(8-chlorooctyl)oxy]-(13aS)-1,2,3,13a-tetrahydro-5H-pyrrolo[2,1-c][1,4]naphthodiazepine-5-one (1g)
- 8-Methoxy-9-[(9-chlorononyl)oxy]-(13aS)-1,2,3,13a-tetrahydro-5H-pyrrolo[2,1-c][1,4]naphthodiazepine-5-one (1h)
- 8-Methoxy-9-[(10-chlorodecyl)oxy]-(13aS)-1,2,3,13a-tetrahydro-5H-pyrrolo[2,1-c][1,4]naphthodiazepine-5-one (1i)
- 9-Methoxy-8-(2-chloroethoxy)-(13aS)-1,2,3,13a-tetrahydro-5H-pyrrolo[2,1-c][1,4]naphthodiazepine-5-one (2a)
- 9-Methoxy-8-(3-chloropropoxy)-(13aS)-1,2,3,13a-tetrahydro-5H-pyrrolo[2,1-c][1,4]naphthodiazepine-5-one (2b)
- 9-Methoxy-8-(4-chlorobutoxy)-(13aS)-1,2,3,13a-tetrahydro-5H-pyrrolo[2,1-c][1,4]naphthodiazepine-5-one (2c)
- 9-Methoxy-8-[(5-chloropentyl)oxy]-(13aS)-1,2,3,13a-tetrahydro-5H-pyrrolo[2,1-c][1,4]naphthodiazepine-5-one (2d)
- 9-Methoxy-8-[(6-chlorohexyl)oxy]-(13aS)-1,2,3,13a-tetrahydro-5H-pyrrolo[2,1-c][1,4]naphthodiazepine-5-one (2e)
- 9-Methoxy-8-[(7-chloroheptyl)oxy]-(13aS)-1,2,3,13a-tetrahydro-5H-pyrrolo[2,1-c][1,4]naphthodiazepine-5-one (2f)
- 9-Methoxy-8-[(8-chlorooctyl)oxy]-(13aS)-1,2,3,13a-tetrahydro-5H-pyrrolo[2,1-c][1,4]naphthodiazepine-5-one (2g)
- 9-Methoxy-8-[(9-chlorononyl)oxy]-(13aS)-1,2,3,13a-tetrahydro-5H-pyrrolo[2,1-c][1,4]naphthodiazepine-5-one (2h)
- 9-Methoxy-8-[(10-chlorodecyl)oxy]-(13aS)-1,2,3,13a-tetrahydro-5H-pyrrolo[2,1-c][1,4]naphthodiazepine-5-one (2i)
- 8-Methoxy-9-[2-(4-methylpiperazino)ethoxy]-(13aS)-1,2,3,13a-tetrahydro-5H-pyrrolo[2,1-c][1,4]naphthodiazepin-5-one (3a)
- 8-Methoxy-9-[3-(4-methylpiperazino)propoxy]-(13aS)-1,2,3,13a-tetrahydro-5H-pyrrolo[2,1-c][1,4]naphthodiazepin-5-one (3b)
- 8-Methoxy-9-[4-(4-methylpiperazino)butoxy]-(13aS)-1,2,3,13a-tetrahydro-5H-pyrrolo[2,1-c][1,4]naphthodiazepin-5-one (3c)
- 8-Methoxy-9-[5-(4-methylpiperazino)pentyloxy]-(13aS)-1,2,3,13a-tetrahydro-5H-pyrrolo[2,1-c][1,4]naphthodiazepin-5-one (3d)
- 8-Methoxy-9-[6-(4-methylpiperazino)hexyloxy]-(13aS)-1,2,3,13a-tetrahydro-5H-pyrrolo[2,1-c][1,4]naphthodiazepin-5-one (3e)
- 8-Methoxy-9-[7-(4-methylpiperazino)heptyloxy]-(13aS)-1,2,3,13a-tetrahydro-5H-pyrrolo[2,1-c][1,4]naphthodiazepin-5-one (3g)
- 8-Methoxy-9-[8-(4-methylpiperazino)octyloxy]-(13aS)-1,2,3,13a-tetrahydro-5H-pyrrolo[2,1-c][1,4]naphthodiazepin-5-one (3g)
- 8-Methoxy-9-[9-(4-methylpiperazino)nonyloxy]-(13aS)-1,2,3,13a-tetrahydro-5H-pyrrolo[2,1-c][1,4]naphthodiazepin-5-one (3h)
- 8-Methoxy-9-[10-(4-methylpiperazino)decyloxy]-(13aS)-1,2,3,13a-tetrahydro-5H-pyrrolo[2,1-c][1,4]naphthodiazepin-5-one (3i)
- 8-Methoxy-9-[2-(4-ethylpiperazino)ethoxy]-(13aS)-1,2,3,13a-tetrahydro-5H-pyrrolo[2,1-c][1,4]naphthodiazepin-5-one (4a)
- 8-Methoxy-9-[3-(4-ethylpiperazino)propoxy]-(13aS)-1,2,3,13a-tetrahydro-5H-pyrrolo[2,1-c][1,4]naphthodiazepin-5-one (4b)
- 8-Methoxy-9-[4-(4-ethylpiperazino)butoxy]-(13aS)-1,2,3,13a-tetrahydro-5H-pyrrolo[2,1-c][1,4]naphthodiazepin-5-one (4c)
- 8-Methoxy-9-[5-(4-ethylpiperazino)pentyloxy]-(13aS)-1,2,3,13a-tetrahydro-5H-pyrrolo[2,1-c][1,4]naphthodiazepin-5-one (4d)
- 8-Methoxy-9-[6-(4-ethylpiperazino)hexyloxy]-(13aS)-1,2,3,13a-tetrahydro-5H-pyrrolo[2,1-c][1,4]naphthodiazepin-5-one (4e)

8-Methoxy-9-[7-(4-ethylpiperazino)heptyloxy]-(13aS)-1,2,3,13a-tetrahydro-5H-pyrrolo[2,1-c][1,4]naphthodiazepin-5-one (4f)

8-Methoxy-9-[8-(4-ethylpiperazino)octyloxy]-(13aS)-1,2,3,13a-tetrahydro-5H-pyrrolo[2,1-c][1,4]naphthodiazepin-5-one (4g)

8-Methoxy-9-[9-(4-ethylpiperazino)nonyloxy]-(13aS)-1,2,3,13a-tetrahydro-5H-pyrrolo[2,1-c][1,4]naphthodiazepin-5-one (4h)

8-Methoxy-9-[10-(4-ethylpiperazino)decyloxy]-(13aS)-1,2,3,13a-tetrahydro-5H-pyrrolo[2,1-c][1,4]naphthodiazepin-5-one (4i)

8-Methoxy-9-[2-(4-aceylpiperazino)ethoxy]-(13aS)-1,2,3,13a-tetrahydro-5H-pyrrolo[2,1-c][1,4]naphthodiazepin-5-one (5a)

8-Methoxy-9-[3-(4-acetylpiperazino)propoxy]-(13aS)-1,2,3,13a-tetrahydro-5H-pyrrolo[2,1-c][1,4]naphthodiazepin-5-one (5b)

8-Methoxy-9-[4-(4-acetylpiperazino)butoxy]-(13aS)-1,2,3,13a-tetrahydro-5H-pyrrolo[2,1-c][1,4]naphthodiazepin-5-one (5c)

8-Methoxy-9-[5-(4-acetylpiperazino)pentyloxy]-(13aS)-1,2,3,13a-tetrahydro-5H-pyrrolo[2,1-c][1,4]naphthodiazepin-5-one (5d)

8-Methoxy-9-[6-(4-acetylpiperazino)hexyloxy]-(13aS)-1,2,3,13a-tetrahydro-5H-pyrrolo[2,1-c][1,4]naphthodiazepin-5-one (5e)

8-Methoxy-9-[7-(4-acetylpiperazino)heptyloxy]-(13aS)-1,2,3,13a-tetrahydro-5H-pyrrolo[2,1-c][1,4]naphthodiazepin-5-one (5f)

8-Methoxy-9-[8-(4-acetylpiperazino)octyloxy]-(13aS)-1,2,3,13a-tetrahydro-5H-pyrrolo[2,1-c][1,4]naphthodiazepin-5-one (5g)

8-Methoxy-9-[9-(4-acetylpiperazino)nonyloxy]-(13aS)-1,2,3,13a-tetrahydro-5H-pyrrolo[2,1-c][1,4]naphthodiazepin-5-one (5h)

8-Methoxy-9-[10-(4-acetylpiperazino)decyloxy]-(13aS)-1,2,3,13a-tetrahydro-5H-pyrrolo[2,1-c][1,4]naphthodiazepin-5-one (5i)

8-Methoxy-9-[2-(4-benzylpiperazino)ethoxy]-(13aS)-1,2,3,13a-tetrahydro-5H-pyrrolo[2,1-c][1,4]naphthodiazepin-5-one (6a)

8-Methoxy-9-[3-(4-benzylpiperazino)propoxy]-(13aS)-1,2,3,13a-tetrahydro-5H-pyrrolo[2,1-c][1,4]naphthodiazepin-5-one (6b)

8-Methoxy-9-[4-(4-benzylpiperazino)butoxy]-(13aS)-1,2,3,13a-tetrahydro-5H-pyrrolo[2,1-c][1,4]naphthodiazepin-5-one (6c)

8-Methoxy-9-[5-(4-benzylpiperazino)pentyloxy]-(13aS)-1,2,3,13a-tetrahydro-5H-pyrrolo[2,1-c][1,4]naphthodiazepin-5-one (6d)

8-Methoxy-9-[6-(4-benzylpiperazino)hexyloxy]-(13aS)-1,2,3,13a-tetrahydro-5H-pyrrolo[2,1-c][1,4]naphthodiazepin-5-one (6e)

8-Methoxy-9-[7-(4-benzylpiperazino)heptyloxy]-(13aS)-1,2,3,13a-tetrahydro-5H-pyrrolo[2,1-c][1,4]naphthodiazepin-5-one (6f)

8-Methoxy-9-[8-(4-benzylpiperazino)octyloxy]-(13aS)-1,2,3,13a-tetrahydro-5H-pyrrolo[2,1-c][1,4]naphthodiazepin-5-one (6g)

8-Methoxy-9-[9-(4-benzylpiperazino)nonyloxy]-(13aS)-1,2,3,13a-tetrahydro-5H-pyrrolo[2,1-c][1,4]naphthodiazepin-5-one (6h)

8-Methoxy-9-[10-(4-benzylpiperazino)decyloxy]-(13aS)-1,2,3,13a-tetrahydro-5H-pyrrolo[2,1-c][1,4]naphthodiazepin-5-one (6i)

8-Methoxy-9-(2-[4-(1,3-benzodioxol-5-ylmethyl)piperazino]ethoxy)(13aS)-1,2,3,13a-tetrahydro-5H-pyrrolo[2,1-c][1,4]naphthodiazepin-5-one (7a)

8-Methoxy-9-(3-[4-(1,3-benzodioxol-5-ylmethyl)piperazino]propoxy)(13aS)-1,2,3,13a-tetrahydro-5H-pyrrolo[2,1-c][1,4]naphthodiazepin-5-one (7b)

8-Methoxy-9-(4-[4-(1,3-benzodioxol-5-ylmethyl)piperazino]butoxy)(13aS)-1,2,3,13a-tetrahydro-5H-pyrrolo[2,1-c][1,4]naphthodiazepin-5-one (7c)

8-Methoxy-9-(5-[4-(1,3-benzodioxol-5-ylmethyl)piperazino]pentyloxy)(13aS)-1,2,3,13a-tetrahydro-5H-pyrrolo[2,1-c][1,4]naphthodiazepin-5-one (7d)

8-Methoxy-9-(6-[4-(1,3-benzodioxol-5-ylmethyl)piperazino]hexyloxy)(13aS)-1,2,3,13a-tetrahydro-5H-pyrrolo[2,1-c][1,4]naphthodiazepin-5-one (7e)

8-Methoxy-9-(7-[4-(1,3-benzodioxol-5-ylmethyl)piperazino]heptyloxy)(13aS)-1,2,3,13a-tetrahydro-5H-pyrrolo[2,1-c][1,4]naphthodiazepin-5-one (7f)

8-Methoxy-9-(8-[4-(1,3-benzodioxol-5-ylmethyl)piperazino]octyloxy)(13aS)-1,2,3,13a-tetrahydro-5H-pyrrolo[2,1-c][1,4]naphthodiazepin-5-one (7g)

8-Methoxy-9-(9-[4-(1,3-benzodioxol-5-ylmethyl)piperazino]nonyloxy)(13aS)-1,2,3,13a-tetrahydro-5H-pyrrolo[2,1-c][1,4]naphthodiazepin-5-one (7h)

8-Methoxy-9-(10-[4-(1,3-benzodioxol-5-ylmethyl)piperazino]decyloxy)(13aS)-1,2,3,13a-tetrahydro-5H-pyrrolo[2,1-c][1,4]naphthodiazepin-5-one (7i)

8-Methoxy-9-[2-(4-phenylpiperazino)ethoxy]-(13aS)-1,2,3,13a-tetrahydro-5H-pyrrolo[2,1-c][1,4]naphthodiazepin-5-one (8a)

8-Methoxy-9-[3-(4-phenylpiperazino)propoxy]-(13aS)-1,2,3,13a-tetrahydro-5H-pyrrolo[2,1-c][1,4]naphthodiazepin-5-one (8b)

8-Methoxy-9-[4-(4-phenylpiperazino)butoxy]-(13aS)-1,2,3,13a-tetrahydro-5H-pyrrolo[2,1-c][1,4]naphthodiazepin-5-one (8c)

8-Methoxy-9-[5-(4-phenylpiperazino)pentyloxy]-(13aS)-1,2,3,13a-tetrahydro-5H-pyrrolo[2,1-c][1,4]naphthodiazepin-5-one (8d)

8-Methoxy-9-[6-(4-phenylpiperazino)hexyloxy]-(13aS)-1,2,3,13a-tetrahydro-5H-pyrrolo[2,1-c][1,4]naphthodiazepin-5-one (8e)

8-Methoxy-9-[7-(4-phenylpiperazino)heptyloxy]-(13aS)-1,2,3,13a-tetrahydro-5H-pyrrolo[2,1-c][1,4]naphthodiazepin-5-one (8f)

8-Methoxy-9-[8-(4-phenylpiperazino)octyloxy]-(13aS)-1,2,3,13a-tetrahydro-5H-pyrrolo[2,1-c][1,4]naphthodiazepin-5-one (8g)

8-Methoxy-9-[9-(4-phenylpiperazino)nonyloxy]-(13aS)-1,2,3,13a-tetrahydro-5H-pyrrolo[2,1-c][1,4]naphthodiazepin-5-one (8h)

8-Methoxy-9-[10-(4-phenylpiperazino)decyloxy]-(13aS)-1,2,3,13a-tetrahydro-5H-pyrrolo[2,1-c][1,4]naphthodiazepin-5-one (8i)

8-Methoxy-9-(2-[4-(4-fluorophenyl)piperazino]ethoxy)-(13aS)-1,2,3,13a-tetrahydro-5H-pyrrolo[2,1-c][1,4]naphthodiazepin-5-one (9a)

8-Methoxy-9-(3-[4-(4-fluorophenyl)piperazino]propoxy)-(13aS)-1,2,3,13a-tetrahydro-5H-pyrrolo[2,1-c][1,4]naphthodiazepin-5-one (9b)

8-Methoxy-9-(4-[4-(4-fluorophenyl)piperazino]butoxy)-(13aS)-1,2,3,13a-tetrahydro-5H-pyrrolo[2,1-c][1,4]naphthodiazepin-5-one (9c)

8-Methoxy-9-(5-[4-(4-fluorophenyl)piperazino]pentyloxy)-(13aS)-1,2,3,13a-tetrahydro-5H-pyrrolo[2,1-c][1,4]naphthodiazepin-5-one (9d)

8-Methoxy-9-(6-[4-(4-fluorophenyl)piperazino]hexyloxy)-(13aS)-1,2,3,13a-tetrahydro-5H-pyrrolo[2,1-c][1,4]naphthodiazepin-5-one (9e)

8-Methoxy-9-(7-[4-(4-fluorophenyl)piperazino]heptyloxy)-(13aS)-1,2,3,13a-tetrahydro-5H-pyrrolo[2,1-c][1,4]naphthodiazepin-5-one (9f)

8-Methoxy-9-(8-[4-(4-fluorophenyl)piperazino]octyloxy)-(13aS)-1,2,3,13a-tetrahydro-5H-pyrrolo[2,1-c][1,4]naphthodiazepin-5-one (9g)

8-Methoxy-9-(9-[4-(4-fluorophenyl)piperazino]nonyloxy)-(13aS)-1,2,3,13a-tetrahydro-5H-pyrrolo[2,1-c][1,4]naphthodiazepin-5-one (9h)

8-Methoxy-9-(10-[4-(4-fluorophenyl)piperazino]decyloxy)-(13aS)-1,2,3,13a-tetrahydro-5H-pyrrolo[2,1-c][1,4]naphthodiazepin-5-one (9i)

8-Methoxy-9-(2-[4-(4-chlorophenyl)piperazino]ethoxy)-(13aS)-1,2,3,13a-tetrahydro-5H-pyrrolo[2,1-c][1,4]naphthodiazepin-5-one (10a)

8-Methoxy-9-(3-[4-(4-chlorophenyl)piperazino]propoxy)-(13aS)-1,2,3,13a-tetrahydro-5H-pyrrolo[2,1-c][1,4]naphthodiazepin-5-one (10b)

8-Methoxy-9-(4-[4-(4-chlorophenyl)piperazino]butoxy)-(13aS)-1,2,3,13a-tetrahydro-5H-pyrrolo[2,1-c][1,4]naphthodiazepin-5-one (10c)

8-Methoxy-9-(5-[4-(4-chlorophenyl)piperazino]pentyloxy)-(13aS)-1,2,3,13a-tetrahydro-5H-pyrrolo[2,1-c][1,4]naphthodiazepin-5-one (10d)

8-Methoxy-9-(6-[4-(4-chlorophenyl)piperazino]hexyloxy)-(13aS)-1,2,3,13a-tetrahydro-5H-pyrrolo[2,1-c][1,4]naphthodiazepin-5-one (10e)

8-Methoxy-9-(7-[4-(4-chlorophenyl)piperazino]heptyloxy)-(13aS)-1,2,3,13a-tetrahydro-5H-pyrrolo[2,1-c][1,4]naphthodiazepin-5-one (10f)

8-Methoxy-9-(8-[4-(4-chlorophenyl)piperazino]octyloxy)-(13aS)-1,2,3,13a-tetrahydro-5H-pyrrolo[2,1-c][1,4]naphthodiazepin-5-one (10g)

8-Methoxy-9-(9-[4-(4-chlorophenyl)piperazino]nonyloxy)-(13aS)-1,2,3,13a-tetrahydro-5H-pyrrolo[2,1-c][1,4]naphthodiazepin-5-one (10h)

8-Methoxy-9-(10-[4-(4-chlorophenyl)piperazino]decyloxy)-(13aS)-1,2,3,13a-tetrahydro-5H-pyrrolo[2,1-c][1,4]naphthodiazepin-5-one (10i)

8-Methoxy-9-(2-[4-(4-metoxyphenyl)piperazino]ethoxy)-(13aS)-1,2,3,13a-tetrahydro-5H-pyrrolo[2,1-c][1,4]naphthodiazepin-5-one (11a)

8-Methoxy-9-(3-[4-(4-metoxyphenyl)piperazino]propoxy)-(13aS)-1,2,3,13a-tetrahydro-5H-pyrrolo[2,1-c][1,4]naphthodiazepin-5-one (11b)

8-Methoxy-9-(4-[4-(4-metoxyphenyl)piperazino]butoxy)-(13aS)-1,2,3,13a-tetrahydro-5H-pyrrolo[2,1-c][1,4]naphthodiazepin-5-one (11c)

8-Methoxy-9-(5-[4-(4-metoxyphenyl)piperazino]pentyloxy)-(13aS)-1,2,3,13a-tetrahydro-5H-pyrrolo[2,1-c][1,4]naphthodiazepin-5-one (11d)

8-Methoxy-9-(6-[4-(4-metoxyphenyl)piperazino]hexyloxy)-(13aS)-1,2,3,13a-tetrahydro-5H-pyrrolo[2,1-c][1,4]naphthodiazepin-5-one (11e)

8-Methoxy-9-(7-[4-(4-metoxyphenyl)piperazino]heptyloxy)-(13aS)-1,2,3,13a-tetrahydro-5H-pyrrolo[2,1-c][1,4]naphthodiazepin-5-one (11f)

8-Methoxy-9-(8-[4-(4-metoxyphenyl)piperazino]octyloxy)-(13aS)-1,2,3,13a-tetrahydro-5H-pyrrolo[2,1-c][1,4]naphthodiazepin-5-one (11g)

8-Methoxy-9-(9-[4-(4-metoxyphenyl)piperazino]nonyloxy)-(13aS)-1,2,3,13a-tetrahydro-5H-pyrrolo[2,1-c][1,4]naphthodiazepin-5-one (11h)

8-Methoxy-9-(10-[4-(4-metoxyphenyl)piperazino]decyloxy)-(13aS)-1,2,3,13a-tetrahydro-5H-pyrrolo[2,1-c][1,4]naphthodiazepin-5-one (11i)

8-Methoxy-9-(2-[4-(2-pyridyl)piperazino]ethoxy)-(13aS)-1,2,3,13a-tetrahydro-5H-pyrrolo[2,1-c][1,4]naphthodiazepin-5-one (12a)

8-Methoxy-9-(3-[4-(2-pyridyl)piperazino]propoxy)-(13aS)-1,2,3,13a-tetrahydro-5H-pyrrolo[2,1-c][1,4]naphthodiazepin-5-one (12b)

8-Methoxy-9-(4-[4-(2-pyridyl)piperazino]butoxy)-(13aS)-1,2,3,13a-tetrahydro-5H-pyrrolo[2,1-c][1,4]naphthodiazepin-5-one (12c)

8-Methoxy-9-(5-[4-(2-pyridyl)piperazino]pentyloxy)-(13aS)-1,2,3,13a-tetrahydro-5H-pyrrolo[2,1-c][1,4]naphthodiazepin-5-one (12d)

8-Methoxy-9-(6-[4-(2-pyridyl)piperazino]hexyloxy)-(13aS)-1,2,3,13a-tetrahydro-5H-pyrrolo[2,1-c][1,4]naphthodiazepin-5-one (12e)

8-Methoxy-9-(7-[4-(2-pyridyl)piperazino]heptyloxy)-(13aS)-1,2,3,13a-tetrahydro-5H-pyrrolo[2,1-c][1,4]naphthodiazepin-5-one (12f)

8-Methoxy-9-(8-[4-(2-pyridyl)piperazino]octyloxy)-(13aS)-1,2,3,13a-tetrahydro-5H-pyrrolo[2,1-c][1,4]naphthodiazepin-5-one (12g)

8-Methoxy-9-(9-[4-(2-pyridyl)piperazino]nonyloxy)-(13aS)-1,2,3,13a-tetrahydro-5H-pyrrolo[2,1-c][1,4]naphthodiazepin-5-one (12h)

8-Methoxy-9-(10-[4-(2-pyridyl)piperazino]decyloxy)-(13aS)-1,2,3,13a-tetrahydro-5H-pyrrolo[2,1-c][1,4]naphthodiazepin-5-one (12i)

8-Methoxy-9-(2-[4-(2-pyrimidinyl)piperazino]ethoxy)-(13aS)-1,2,3,13a-tetrahydro-5H-pyrrolo[2,1-c][1,4]naphthodiazepin-5-one (13a)

8-Methoxy-9-(3-[4-(2-pyrimidinyl)piperazino]propoxy)-(13aS)-1,2,3,13a-tetrahydro-5H-pyrrolo[2,1-c][1,4]naphthodiazepin-5-one (13b)

8-Methoxy-9-(4-[4-(2-pyrimidinyl)piperazino]butoxy)-(13aS)-1,2,3,13a-tetrahydro-5H-pyrrolo[2,1-c][1,4]naphthodiazepin-5-one (13c)

8-Methoxy-9-(5-[4-(2-pyrimidinyl)piperazino]pentyloxy)-(13aS)-1,2,3,13a-tetrahydro-5H-pyrrolo[2,1-c][1,4]naphthodiazepin-5-one (13d)

8-Methoxy-9-(6-[4-(2-pyrimidinyl)piperazino]hexyloxy)-(13aS)-1,2,3,13a-tetrahydro-5H-pyrrolo[2,1-c][1,4]naphthodiazepin-5-one (13e)

8-Methoxy-9-(7-[4-(2-pyrimidinyl)piperazino]heptyloxy)-(13aS)-1,2,3,13a-tetrahydro-5H-pyrrolo[2,1-c][1,4]naphthodiazepin-5-one (13f)

8-Methoxy-9-(8-[4-(2-pyrimidinyl)piperazino]octyloxy)-(13aS)-1,2,3,13a-tetrahydro-5H-pyrrolo[2,1-c][1,4]naphthodiazepin-5-one (13g)

8-Methoxy-9-(9-[4-(2-pyrimidinyl)piperazino]nonyloxy)-(13a9-1,2,3,13a-tetrahydro-5H-pyrrolo[2,1-c][1,4]naphthodiazepin-5-one (13h)

8-Methoxy-9-(10-[4-(2-pyrimidinyl)piperazino]decyloxy)-(13aS)-1,2,3,13a-tetrahydro-5H-pyrrolo[2,1-c][1,4]naphthodiazepin-5-one (13i)

9-Methoxy-8-[2-(4-methylpiperazino)ethoxy]-(13aS)-1,2,3,13a-tetrahydro-5H-pyrrolo[2,1-c][1,4]naphthodiazepin-5-one (14a)

9-Methoxy-8-[3-(4-methylpiperazino)propoxy]-(13aS)-1,2,3,13a-tetrahydro-5H-pyrrolo[2,1-c][1,4]naphthodiazepin-5-one (14b)

9-Methoxy-8-[4-(4-methylpiperazino)butoxy]-(13aS)-1,2,3,13a-tetrahydro-5H-pyrrolo[2,1-c][1,4]naphthodiazepin-5-one (14c)

9-Methoxy-8-[5-(4-methylpiperazino)pentyloxy]-(13aS)-1,2,3,13a-tetrahydro-5H-pyrrolo[2,1-c][1,4]naphthodiazepin-5-one (14d)

9-Methoxy-8-[6-(4-methylpiperazino)hexyloxy]-(13aS)-1,2,3,13a-tetrahydro-5H-pyrrolo[2,1-c][1,4]naphthodiazepin-5-one (14e)

9-Methoxy-8-[7-(4-methylpiperazino)heptyloxy]-(13aS)-1,2,3,13a-tetrahydro-5H-pyrrolo[2,1-c][1,4]naphthodiazepin-5-one (14f)

9-Methoxy-8-[8-(4-methylpiperazino)octyloxy]-(13aS)-1,2,3,13a-tetrahydro-5H-pyrrolo[2,1-c][1,4]naphthodiazepin-5-one (14g)

9-Methoxy-8-[9-(4-methylpiperazino)nonyloxy]-(13aS)-1,2,3,13a-tetrahydro-5H-pyrrolo[2,1-c][1,4]naphthodiazepin-5-one (14h)

9-Methoxy-8-[10-(4-methylpiperazino)decyloxy]-(13aS)-1,2,3,13a-tetrahydro-5H-pyrrolo[2,1-c][1,4]naphthodiazepin-5-one (14i)

9-Methoxy-8-[2-(4-ethylpiperazino)ethoxy]-(13aS)-1,2,3,13a-tetrahydro-5H-pyrrolo[2,1-c][1,4]naphthodiazepin-5-one (15a)

9-Methoxy-8-[3-(4-ethylpiperazino)propoxy]-(13aS)-1,2,3,13a-tetrahydro-5H-pyrrolo[2,1-c][1,4]naphthodiazepin-5-one (15b)

9-Methoxy-8-[4-(4-ethylpiperazino)butoxy]-(13aS)-1,2,3,13a-tetrahydro-5H-pyrrolo[2,1-c][1,4]naphthodiazepin-5-one (15c)

9-Methoxy-8-[5-(4-ethylpiperazino)pentyloxy]-(13aS)-1,2,3,13a-tetrahydro-5H-pyrrolo[2,1-c][1,4]naphthodiazepin-5-one (15d)

9-Methoxy-8-[6-(4-ethylpiperazino)hexyloxy]-(13aS)-1,2,3,13a-tetrahydro-5H-pyrrolo[2,1-c][1,4]naphthodiazepin-5-one (15e)

9-Methoxy-8-[7-(4-ethylpiperazino)heptyloxy]-(13aS)-1,2,3,13a-tetrahydro-5H-pyrrolo[2,1-c][1,4]naphthodiazepin-5-one (15f)

9-Methoxy-8-[8-(4-ethylpiperazino)octyloxy]-(13aS)-1,2,3,13a-tetrahydro-5H-pyrrolo[2,1-c][1,4]naphthodiazepin-5-one (15g)

9-Methoxy-8-[9-(4-ethylpiperazino)nonyloxy]-(13aS)-1,2,3,13a-tetrahydro-5H-pyrrolo[2,1-c][1,4]naphthodiazepin-5-one (15h)

9-Methoxy-8-[10-(4-ethylpiperazino)decyloxy]-(13aS)-1,2,3,13a-tetrahydro-5H-pyrrolo[2,1-c][1,4]naphthodiazepin-5-one (15i)

9-Methoxy-8-[2-(4-aceylpiperazino)ethoxy]-(13aS)-1,2,3,13a-tetrahydro-5H-pyrrolo[2,1-c][1,4]naphthodiazepin-5-one (16a)

9-Methoxy-8-[3-(4-acetylpiperazino)propoxy]-(13aS)-1,2,3,13a-tetrahydro-5H-pyrrolo[2,1-c][1,4]naphthodiazepin-5-one (16b)

9-Methoxy-8-[4-(4-acetylpiperazino)butoxy]-(13aS)-1,2,3,13a-tetrahydro-5H-pyrrolo[2,1-c][1,4]naphthodiazepin-5-one (16c)

9-Methoxy-8-[5-(4-acetylpiperazino)pentyloxy]-(13aS)-1,2,3,13a-tetrahydro-5H-pyrrolo[2,1-c][1,4]naphthodiazepin-5-one (16d)

9-Methoxy-8-[6-(4-acetylpiperazino)hexyloxy]-(13aS)-1,2,3,13a-tetrahydro-5H-pyrrolo[2,1-c][1,4]naphthodiazepin-5-one (16e)

9-Methoxy-8-[7-(4-acetylpiperazino)heptyloxy]-(13aS)-1,2,3,13a-tetrahydro-5H-pyrrolo[2,1-c][1,4]naphthodiazepin-5-one (16f)

9-Methoxy-8-[8-(4-acetylpiperazino)octyloxy]-(13aS)-1,2,3,13a-tetrahydro-5H-pyrrolo[2,1-c][1,4]naphthodiazepin-5-one (16g)

9-Methoxy-8-[9-(4-acetylpiperazino)nonyloxy]-(13aS)-1,2,3,13a-tetrahydro-5H-pyrrolo[2,1-c][1,4]naphthodiazepin-5-one (16h)

9-Methoxy-8-[10-(4-acetylpiperazino)decyloxy]-(13aS)-1,2,3,13a-tetrahydro-5H-pyrrolo[2,1-c][1,4]naphthodiazepin-5-one (16i)

9-Methoxy-8-[2-(4-benzylpiperazino)ethoxy]-(13aS)-1,2,3,13a-tetrahydro-5H-pyrrolo[2,1-c][1,4]naphthodiazepin-5-one (17a)

9-Methoxy-8-[3-(4-benzylpiperazino)propoxy]-(13aS)-1,2,3,13a-tetrahydro-5H-pyrrolo[2,1-c][1,4]naphthodiazepin-5-one (17b)

9-Methoxy-8-[4-(4-benzylpiperazino)butoxy]-(13aS)-1,2,3,13a-tetrahydro-5H-pyrrolo[2,1-c][1,4]naphthodiazepin-5-one (17c)

9-Methoxy-8-[5-(4-benzylpiperazino)pentyloxy]-(13aS)-1,2,3,13a-tetrahydro-5H-pyrrolo[2,1-c][1,4]naphthodiazepin-5-one (17d)

9-Methoxy-8-[6-(4-benzylpiperazino)hexyloxy]-(13aS)-1,2,3,13a-tetrahydro-5H-pyrrolo[2,1-c][1,4]naphthodiazepin-5-one (17e)

9-Methoxy-8-[7-(4-benzylpiperazino)heptyloxy]-(13aS)-1,2,3,13a-tetrahydro-5H-pyrrolo[2,1-c][1,4]naphthodiazepin-5-one (17f)

9-Methoxy-8-[8-(4-benzylpiperazino)octyloxy]-(13aS)-1,2,3,13a-tetrahydro-5H-pyrrolo[2,1-c][1,4]naphthodiazepin-5-one (17g)

9-Methoxy-8-[9-(4-benzylpiperazino)nonyloxy]-(13aS)-1,2,3,13a-tetrahydro-5H-pyrrolo[2,1-c][1,4]naphthodiazepin-5-one (17h)

9-Methoxy-8-[10-(4-benzylpiperazino)decyloxy]-(13aS)-1,2,3,13a-tetrahydro-5H-pyrrolo[2,1-c][1,4]naphthodiazepin-5-one (17i)

9-Methoxy-8-(2-[4-(1,3-benzodioxol-5-ylmethyl)piperazino]ethoxy)(13aS)-1,2,3,13a-tetrahydro-5H-pyrrolo[2,1-c][1,4]naphthodiazepin-5-one (18a)

9-Methoxy-8-(3-[4-(1,3-benzodioxol-5-ylmethyl)piperazino]propoxy)(13aS)-1,2,3,13a-tetrahydro-5H-pyrrolo[2,1-c][1,4]naphthodiazepin-5-one (18b)

9-Methoxy-8-(4-[4-(1,3-benzodioxol-5-ylmethyl)piperazino]butoxy)(13aS)-1,2,3,13a-tetrahydro-5H-pyrrolo[2,1-c][1,4]naphthodiazepin-5-one (18c)

9-Methoxy-8-(5-[4-(1,3-benzodioxol-5-ylmethyl)piperazino]pentyloxy)(13aS)-1,2,3,13a-tetrahydro-5H-pyrrolo[2,1-c][1,4]naphthodiazepin-5-one (18d)

9-Methoxy-8-(6-[4-(1,3-benzodioxol-5-ylmethyl)piperazino]hexyloxy)(13aS)-1,2,3,13a-tetrahydro-5H-pyrrolo[2,1-c][1,4]naphthodiazepin-5-one (18e)

9-Methoxy-8-(7-[4-(1,3-benzodioxol-5-ylmethyl)piperazino]heptyloxy)(13aS)-1,2,3,13a-tetrahydro-5H-pyrrolo[2,1-c][1,4]naphthodiazepin-5-one (18f)

9-Methoxy-8-(8-[4-(1,3-benzodioxol-5-ylmethyl)piperazino]octyloxy)(13aS)-1,2,3,13a-tetrahydro-5H-pyrrolo[2,1-c][1,4]naphthodiazepin-5-one (18g)

9-Methoxy-8-(9-[4-(1,3-benzodioxol-5-ylmethyl)piperazino]nonyloxy)(13aS)-1,2,3,13a-tetrahydro-5H-pyrrolo[2,1-c][1,4]naphthodiazepin-5-one (18h)

9-Methoxy-8-(10-[4-(1,3-benzodioxol-5-ylmethyl)piperazino]decyloxy)(13aS)-1,2,3,13a-tetrahydro-5H-pyrrolo[2,1-c][1,4]naphthodiazepin-5-one (18i)

9-Methoxy-8-[2-(4-phenylpiperazino)ethoxy]-(13aS)-1,2,3,13a-tetrahydro-5H-pyrrolo[2,1-c][1,4]naphthodiazepin-5-one (19a)

9-Methoxy-8-[3-(4-phenylpiperazino)propoxy]-(13aS)-1,2,3,13a-tetrahydro-5H-pyrrolo[2,1-c][1,4]naphthodiazepin-5-one (19b)

9-Methoxy-8-[4-(4-phenylpiperazino)butoxy]-(13aS)-1,2,3,13a-tetrahydro-5H-pyrrolo[2,1-c][1,4]naphthodiazepin-5-one (19c)

9-Methoxy-8-[5-(4-phenylpiperazino)pentyloxy]-(13aS)-1,2,3,13a-tetrahydro-5H-pyrrolo[2,1-c][1,4]naphthodiazepin-5-one (19d)

9-Methoxy-8-[6-(4-phenylpiperazino)hexyloxy]-(13aS)-1,2,3,13a-tetrahydro-5H-pyrrolo[2,1-c][1,4]naphthodiazepin-5-one (19e)

9-Methoxy-8-[7-(4-phenylpiperazino)heptyloxy]-(13aS)-1,2,3,13a-tetrahydro-5H-pyrrolo[2,1-c][1,4]naphthodiazepin-5-one (19f)

9-Methoxy-8-[8-(4-phenylpiperazino)octyloxy]-(13aS)-1,2,3,13a-tetrahydro-5H-pyrrolo[2,1-c][1,4]naphthodiazepin-5-one (19g)

9-Methoxy-8-[9-(4-phenylpiperazino)nonyloxy]-(13aS)-1,2,3,13a-tetrahydro-5H-pyrrolo[2,1-c][1,4]naphthodiazepin-5-one (19h)

9-Methoxy-8-[10-(4-phenylpiperazino)decyloxy]-(13aS)-1,2,3,13a-tetrahydro-5H-pyrrolo[2,1-c][1,4]naphthodiazepin-5-one (19i)

9-Methoxy-8-(2-[4-(4-fluorophenyl)piperazino]ethoxy)-(13aS)-1,2,3,13a-tetrahydro-5H-pyrrolo[2,1-c][1,4]naphthodiazepin-5-one (20a)

9-Methoxy-8-(3-[4-(4-fluorophenyl)piperazino]propoxy)-(13aS)-1,2,3,13a-tetrahydro-5H-pyrrolo[2,1-c][1,4]naphthodiazepin-5-one (20b)

9-Methoxy-8-(4-[4-(4-fluorophenyl)piperazino]butoxy)-(13aS)-1,2,3,13a-tetrahydro-5H-pyrrolo[2,1-c][1,4]naphthodiazepin-5-one (20c)

9-Methoxy-8-(5-[4-(4-fluorophenyl)piperazino]pentyloxy)-(13aS)-1,2,3,13a-tetrahydro-5H-pyrrolo[2,1-c][1,4]naphthodiazepin-5-one (20d)

9-Methoxy-8-(6-[4-(4-fluorophenyl)piperazino]hexyloxy)-(13aS)-1,2,3,13a-tetrahydro-5H-pyrrolo[2,1-c][1,4]naphthodiazepin-5-one (20e)

9-Methoxy-8-(7-[4-(4-fluorophenyl)piperazino]heptyloxy)-(13aS)-1,2,3,13a-tetrahydro-5H-pyrrolo[2,1-c][1,4]naphthodiazepin-5-one (20f)

9-Methoxy-8-(8-[4-(4-fluorophenyl)piperazino]octyloxy)-(13aS)-1,2,3,13a-tetrahydro-5H-pyrrolo[2,1-c][1,4]naphthodiazepin-5-one (20g)

9-Methoxy-8-(9-[4-(4-fluorophenyl)piperazino]nonyloxy)-(13aS)-1,2,3,13a-tetrahydro-5H-pyrrolo[2,1-c][1,4]naphthodiazepin-5-one (20h)

9-Methoxy-8-(10-[4-(4-fluorophenyl)piperazino]decyloxy)-(13aS)-1,2,3,13a-tetrahydro-5H-pyrrolo[2,1-c][1,4]naphthodiazepin-5-one (20i)

9-Methoxy-8-(2-[4-(4-chlorophenyl)piperazino]ethoxy)-(13aS)-1,2,3,13a-tetrahydro-5H-pyrrolo[2,1-c][1,4]naphthodiazepin-5-one (21a)

9-Methoxy-8-(3-[4-(4-chlorophenyl)piperazino]propoxy)-(13aS)-1,2,3,13a-tetrahydro-5H-pyrrolo[2,1-c][1,4]naphthodiazepin-5-one (21b)

9-Methoxy-8-(4-[4-(4-chlorophenyl)piperazino]butoxy)-(13aS)-1,2,3,13a-tetrahydro-5H-pyrrolo[2,1-c][1,4]naphthodiazepin-5-one (21c)

9-Methoxy-8-(5-[4-(4-chlorophenyl)piperazino]pentyloxy)-(13aS)-1,2,3,13a-tetrahydro-5H-pyrrolo[2,1-c][1,4]naphthodiazepin-5-one (21d)

9-Methoxy-8-(6-[4-(4-chlorophenyl)piperazino]hexyloxy)-(13aS)-1,2,3,13a-tetrahydro-5H-pyrrolo[2,1-c][1,4]naphthodiazepin-5-one (21e)

9-Methoxy-8-(7-[4-(4-chlorophenyl)piperazino]heptyloxy)-(13aS)-1,2,3,13a-tetrahydro-5H-pyrrolo[2,1-c][1,4]naphthodiazepin-5-one (21f)

9-Methoxy-8-(8-[4-(4-chlorophenyl)piperazino]octyloxy)-(13aS)-1,2,3,13a-tetrahydro-5H-pyrrolo[2,1-c][1,4]naphthodiazepin-5-one (21g)

9-Methoxy-8-(9-[4-(4-chlorophenyl)piperazino]nonyloxy)-(13aS)-1,2,3,13a-tetrahydro-5H-pyrrolo[2,1-c][1,4]naphthodiazepin-5-one (21h)

9-Methoxy-8-(10-[4-(4-chlorophenyl)piperazino]decyloxy)-(13aS)-1,2,3,13a-tetrahydro-5H-pyrrolo[2,1-c][1,4]naphthodiazepin-5-one (21i)

9-Methoxy-8-(2-[4-(4-metoxyphenyl)piperazino]ethoxy)-(13aS)-1,2,3,13a-tetrahydro-5H-pyrrolo[2,1-c][1,4]naphthodiazepin-5-one (22a)

9-Methoxy-8-(3-[4-(4-metoxyphenyl)piperazino]propoxy)-(13aS)-1,2,3,13a-tetrahydro-5H-pyrrolo[2,1-c][1,4]naphthodiazepin-5-one (22b)

9-Methoxy-8-(4-[4-(4-metoxyphenyl)piperazino]butoxy)-(13aS)-1,2,3,13a-tetrahydro-5H-pyrrolo[2,1-c][1,4]naphthodiazepin-5-one (22c)

9-Methoxy-8-(5-[4-(4-metoxyphenyl)piperazino]pentyloxy)-(13aS)-1,2,3,13a-tetrahydro-5H-pyrrolo[2,1-c][1,4]naphthodiazepin-5-one (22d)

9-Methoxy-8-(6-[4-(4-metoxyphenyl)piperazino]hexyloxy)-(13aS)-1,2,3,13a-tetrahydro-5H-pyrrolo[2,1-c][1,4]naphthodiazepin-5-one (22e)

9-Methoxy-8-(7-[4-(4-metoxyphenyl)piperazino]heptyloxy)-(13aS)-1,2,3,13a-tetrahydro-5H-pyrrolo[2,1-c][1,4]naphthodiazepin-5-one (22f)

9-Methoxy-8-(8-[4-(4-metoxyphenyl)piperazino]octyloxy)-(13aS)-1,2,3,13a-tetrahydro-5H-pyrrolo[2,1-c][1,4]naphthodiazepin-5-one (22g)

9-Methoxy-8-(9-[4-(4-metoxyphenyl)piperazino]nonyloxy)-(13aS)-1,2,3,13a-tetrahydro-5H-pyrrolo[2,1-c][1,4]naphthodiazepin-5-one (22h)

9-Methoxy-8-(10-[4-(4-metoxyphenyl)piperazino]decyloxy)-(13aS)-1,2,3,13a-tetrahydro-5H-pyrrolo[2,1-c][1,4]naphthodiazepin-5-one (22i)

9-Methoxy-8-(2-[4-(2-pyridyl)piperazino]ethoxy)-(13aS)-1,2,3,13a-tetrahydro-5H-pyrrolo[2,1-c][1,4]naphthodiazepin-5-one (23a)

9-Methoxy-8-(3-[4-(2-pyridyl)piperazino]propoxy)-(13aS)-1,2,3,13a-tetrahydro-5H-pyrrolo[2,1-c][1,4]naphthodiazepin-5-one (23b)

9-Methoxy-8-(4-[4-(2-pyridyl)piperazino]butoxy)-(13aS)-1,2,3,13a-tetrahydro-5H-pyrrolo[2,1-c][1,4]naphthodiazepin-5-one (23c)

9-Methoxy-8-(5-[4-(2-pyridyl)piperazino]pentyloxy)-(13aS)-1,2,3,13a-tetrahydro-5H-pyrrolo[2,1-c][1,4]naphthodiazepin-5-one (23d)

9-Methoxy-8-(6-[4-(2-pyridyl)piperazino]hexyloxy)-(13aS)-1,2,3,13a-tetrahydro-5H-pyrrolo[2,1-c][1,4]naphthodiazepin-5-one (23e)

9-Methoxy-8-(7-[4-(2-pyridyl)piperazino]heptyloxy)-(13aS)-1,2,3,13a-tetrahydro-5H-pyrrolo[2,1-c][1,4]naphthodiazepin-5-one (23f)

9-Methoxy-8-(8-[4-(2-pyridyl)piperazino]octyloxy)-(13aS)-1,2,3,13a-tetrahydro-5H-pyrrolo[2,1-c][1,4]naphthodiazepin-5-one (23g)

9-Methoxy-8-(9-[4-(2-pyridyl)piperazino]nonyloxy)-(13aS)-1,2,3,13a-tetrahydro-5H-pyrrolo[2,1-c][1,4]naphthodiazepin-5-one (23h)

9-Methoxy-8-(1-[4-(2-pyridyl)piperazino]decyloxy)-(13aS)-1,2,3,13a-tetrahydro-5H-pyrrolo[2,1-c][1,4]naphthodiazepin-5-one (23i)

9-Methoxy-8-(2-[4-(2-pyrimidinyl)piperazino]ethoxy)-(13aS)-1,2,3,13a-tetrahydro-5H-pyrrolo[2,1-c][1,4]naphthodiazepin-5-one (24a)

9-Methoxy-8-(3-[4-(2-pyrimidinyl)piperazino]propoxy)-(13aS)-1,2,3,13a-tetrahydro-5H-pyrrolo[2,1-c][1,4]naphthodiazepin-5-one (24b)

9-Methoxy-8-(4-[4-(2-pyrimidinyl)piperazino]butoxy)-(13aS)-1,2,3,13a-tetrahydro-5H-pyrrolo[2,1-c][1,4]naphthodiazepin-5-one (24c)

9-Methoxy-8-(5-[4-(2-pyrimidinyl)piperazino]pentyloxy)-(13aS)-1,2,3,13a-tetrahydro-5H-pyrrolo[2,1-c][1,4]naphthodiazepin-5-one (24d)

9-Methoxy-8-(6-[4-(2-pyrimidinyl)piperazino]hexyloxy)-(13aS)-1,2,3,13a-tetrahydro-5H-pyrrolo[2,1-c][1,4]naphthodiazepin-5-one (24e)

9-Methoxy-8-(7-[4-(2-pyrimidinyl)piperazino]heptyloxy)-(13aS)-1,2,3,13a-tetrahydro-5H-pyrrolo[2,1-c][1,4]naphthodiazepin-5-one (24f)

9-Methoxy-8-(8-[4-(2-pyrimidinyl)piperazino]octyloxy)-(13aS)-1,2,3,13a-tetrahydro-5H-pyrrolo[2,1-c][1,4]naphthodiazepin-5-one (24g)

9-Methoxy-8-(9-[4-(2-pyrimidinyl)piperazino]nonyloxy)-(13aS)-1,2,3,13a-tetrahydro-5H-pyrrolo[2,1-c][1,4]naphthodiazepin-5-one (24h)

9-Methoxy-8-(10-[4-(2-pyrimidinyl)piperazino]decyloxy)-(13aS)-1,2,3,13a-tetrahydro-5H-pyrrolo[2,1-c][1,4]naphthodiazepin-5-one (24i).

3. The compound of claim 2, further defined as 8-Methoxy-9-(2-chloroethoxy)-(13aS)-1,2,3,13a-tetrahydro-5H-pyrrolo[2,1-c][1,4]naphthodiazepine-5-one (1a).

4. The compound of claim 2, further defined as 9-Methoxy-8-(2-chloroethoxy)-(13aS)-1,2,3,13a-tetrahydro-5H-pyrrolo[2,1-c][1,4]naphthodiazepine-5-one (2a).

5. The compound of claim 2, further defined as 8-Methoxy-9-[2-(4-aceylpiperazino)ethoxy]-(13aS)-1,2,3,13a-tetrahydro-5H-pyrrolo[2,1-c][1,4]naphthodiazepin-5-one (5a).

6. The compound of claim 2, further defined as 8-Methoxy-9-(2-[4-(1,3-benzodioxol-5-ylmethyl)piperazino]ethoxy)(13aS)-1,2,3,13a-tetrahydro-5H-pyrrolo[2,1-c][1,4]naphthodiazepin-5-one (7a).

7. The compound of claim 2, further defined as 8-Methoxy-9-[2-(4-phenylpiperazino)ethoxy]-(13aS)-1,2,3,13a-tetrahydro-5H-pyrrolo[2,1-c][1,4]naphthodiazepin-5-one (8a).

8. The compound of claim 2, further defined as 8-Methoxy-9-(2-[4-(2-pyridyl)piperazino]ethoxy)-(13aS)-1,2,3,13a-tetrahydro-5H-pyrrolo[2,1-c][1,4]naphthodiazepin-5-one (12a).

9. The compound of claim 2, further defined as 8-Methoxy-9-(2-[4-(2-pyrimidinyl)piperazino]ethoxy)-(13aS)-1,2,3,13a-tetrahydro-5H-pyrrolo[2,1-c][1,4]naphthodiazepin-5-one (13a).

10. The compound of claim 2, further defined as 9-Methoxy-8-[2-(4-ethylpiperazino)ethoxy]-(13aS)-1,2,3,13a-tetrahydro-5H-pyrrolo[2,1-c][1,4]naphthodiazepin-5-one (15a).

11. The compound of claim 2, further defined as 9-Methoxy-8-[2-(4-phenylpiperazino)ethoxy]-(13aS)-1,2,3,13a-tetrahydro-5H-pyrrolo[2,1-c][1,4]naphthodiazepin-5-one (19a).

12. The compound of claim 2, further defined as 9-Methoxy-8-(2-[4-(4-fluorophenyl)piperazino]ethoxy)-(13aS)-1,2,3,13a-tetrahydro-5H-pyrrolo[2,1-c][1,4]naphthodiazepin-5-one (20a).

13. The compound of claim 2, further defined as 9-Methoxy-8-(2-[4-(2-pyridyl)piperazino]ethoxy)-(13aS)-1,2,3,13a-tetrahydro-5H-pyrrolo[2,1-c][1,4]naphthodiazepin-5-one (23a).

14. The compound of claim 2, further defined as 9-Methoxy-8-(2-[4-(2-pyrimidinyl)piperazino]ethoxy)-(13aS)-1,2,3,13a-tetrahydro-5H-pyrrolo[2,1-c][1,4]naphthodiazepin-5-one (24a).

15. A process for the preparation of the compound according to claim 1, the process comprising the steps of:

(a) reacting compound of formula 27a or 27b with LiOH.H$_2$O in THF:MeOH:H$_2$O (4:1:1) at temperature ranging between 27 to 30° C. for a period ranging between 4 to 6 h to obtain compound of formula 28a or 28b respectively;

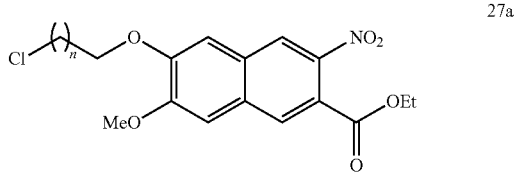

27a

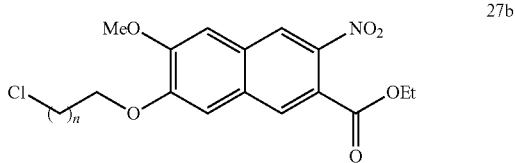

27b

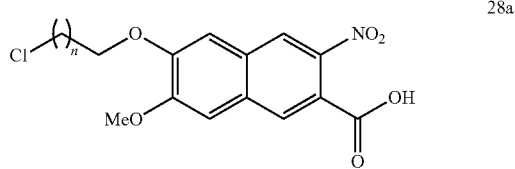

28a

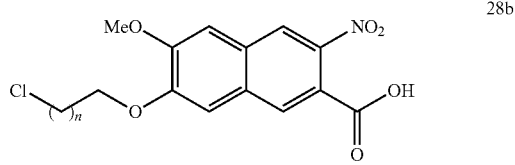

28b n = 1 to 9

(b) reacting compounds of formula 28a or 28b as obtained in step (a) with SOCl$_2$ in benzene at temperature ranging between 27 to 30° C. for a period ranging between 6 to 8 h and followed by coupling with (S)-methylpyrrolidine-2-carboxylate in THF (tetrahydro furan) at temperature ranging between 0 to 5° C. to obtain compound of formula 29a or 29b respectively:

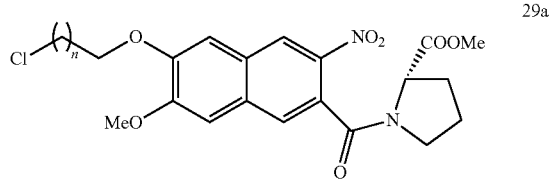

29a

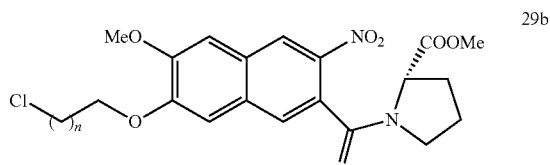

29b n = 1 to 9

(c) reacting the compounds of formula 29a or 29b as obtained in step (b) with DIABAL-H (diisobutylaluminiumhydride) in dichloromethane (DCM) solvent at temperature ranging between −60 to-78° C. for a period ranging between 30 to 40 min and protecting with EtSH (ethanethiol) and TMSCl (trimethylsilylchloride) at temperature ranging between 27 to 30° C. for a period ranging between 8 to 12 h to obtain compounds of formula 30a or 30b respectively:

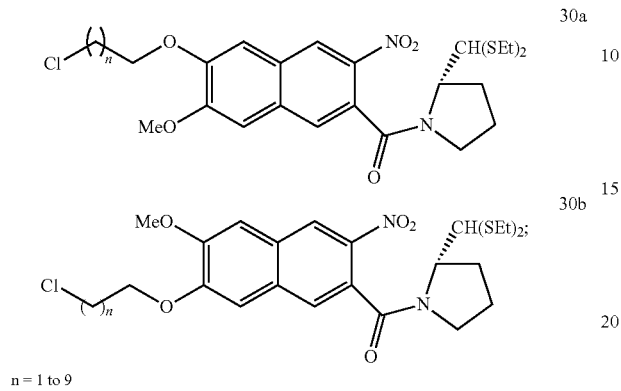

n = 1 to 9

(d) reacting the compounds of formula 30a or 30b as obtained in step (c) with substituted piperazines in mole ratio ranging between 1:5 to 1:10 at temperature ranging between 100 to 120° C. for a period ranging between to obtain nitro compounds of formula 32a or 32b respectively:

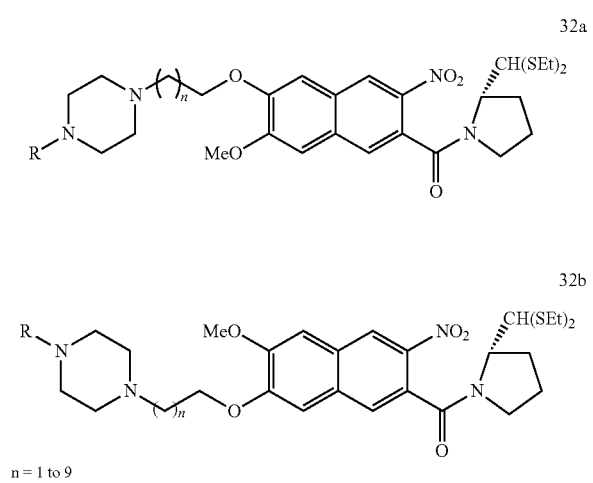

n = 1 to 9

(e) reducing the nitro compound of formula 30a or 30b or 32a or 32b as obtained in step (c) or (d) with SnCl$_2$.2H$_2$O in methanol solvent at temperature range of 65 to 70° C. for a period ranging between 3 to 5 h to obtain amino compound of formula 31a or 31b or 33a or 33b respectively:

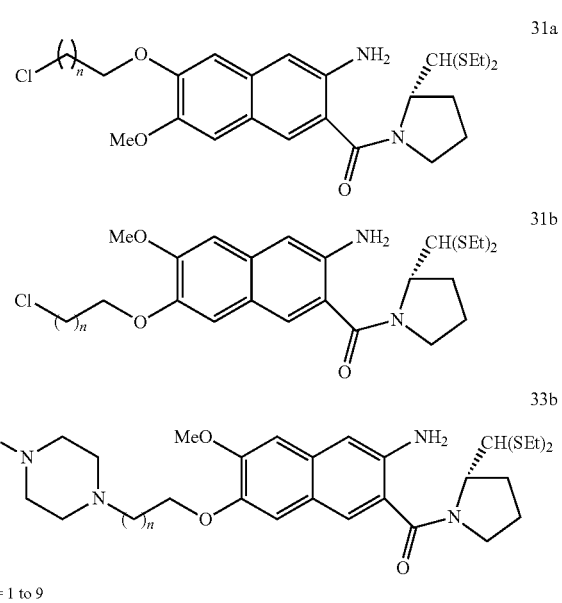

n = 1 to 9

(f) reacting the amino compound of formula 31a or 31b or 33a or 33b as obtained in step (e) with a deprotecting agent HgCl$_2$ and CaCO$_3$ in MeCN:H$_2$O (4:1 ratio) at temperature ranging between 27 to 30° C. for a period ranging between 12 to 24 h to obtain the desired compound of formula 1a-i to 24a-i.

16. The process according to claim 15, wherein the substituted piperazines of step (d) is selected from the group consisting of 1-acetyl piperazine, 1-piperinoyl piperazine, 1-phenyl piperazine, 1-pyridyl piperazine, 1-pyrimidyl piperazine, 1-ethyl piperazine, 1-(4-fluorophenyl)piperazine, 1-benzyl piperazine, 1-(4-chlorophenyl)piperazine and 1-(4-methoxyphenyl)piperazine.

17. The process according to claim 15, wherein yield of compound of claim 1, is in the range of 55-75%.

* * * * *